United States Patent
Hanna et al.

(10) Patent No.: US 10,889,631 B2
(45) Date of Patent: Jan. 12, 2021

(54) THERAPEUTIC VARIANT ALPHA-2-MACROGLOBULIN COMPOSITIONS

(71) Applicant: CYTONICS CORPORATION, Jupiter, FL (US)

(72) Inventors: Lewis Hanna, Naples, FL (US); John David Laughlin, Jupiter, FL (US); Shawn Robert Browning, Jupiter, FL (US)

(73) Assignee: Cytonics Corporation, Jupiter, FL (US)

( * ) Notice: Subject to any disclaimer, the term of this patent is extended or adjusted under 35 U.S.C. 154(b) by 0 days.

(21) Appl. No.: 16/514,591

(22) Filed: Jul. 17, 2019

(65) Prior Publication Data

US 2019/0359690 A1  Nov. 28, 2019
US 2020/0148748 A9  May 14, 2020

Related U.S. Application Data

(62) Division of application No. 15/528,387, filed as application No. PCT/US2015/061852 on Nov. 20, 2015, now Pat. No. 10,400,028.

(60) Provisional application No. 62/082,304, filed on Nov. 20, 2014.

(51) Int. Cl.
| | | |
|---|---|---|
| *C07K 14/81* | (2006.01) |
| *A61K 45/06* | (2006.01) |
| *C12Q 1/37* | (2006.01) |
| *C12P 19/34* | (2006.01) |
| *A61K 38/57* | (2006.01) |
| *A61K 9/00* | (2006.01) |

(52) U.S. Cl.
CPC .......... *C07K 14/811* (2013.01); *A61K 9/0019* (2013.01); *A61K 38/57* (2013.01); *A61K 45/06* (2013.01); *C12P 19/34* (2013.01); *C12Q 1/37* (2013.01); *G01N 2333/811* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | |
|---|---|---|
| 4,518,584 A | 5/1985 | Mark et al. |
| 4,683,195 A | 7/1987 | Mullis et al. |
| 4,683,202 A | 7/1987 | Mullis |
| 4,800,159 A | 1/1989 | Mullis et al. |
| 5,728,554 A | 3/1998 | Bayer et al. |
| 5,876,980 A | 3/1999 | Defrees et al. |
| 5,922,577 A | 7/1999 | Defrees et al. |
| 6,030,815 A | 2/2000 | Defrees et al. |
| 6,472,140 B1 | 10/2002 | Tanzi et al. |
| 7,709,215 B2 | 5/2010 | Scuderi |
| 10,265,388 B2 | 4/2019 | Hanna et al. |
| 10,400,028 B2 | 9/2019 | Hanna et al. |
| 2003/0162202 A1 | 8/2003 | Becker et al. |
| 2003/0180835 A1 | 9/2003 | Bayer |
| 2004/0253228 A1 | 12/2004 | Srivastava |
| 2006/0165710 A1 | 7/2006 | Srivastava |
| 2010/0098684 A1 | 4/2010 | Scuderi et al. |
| 2014/0223588 A1 | 8/2014 | Batxelli et al. |
| 2019/0290741 A1 | 9/2019 | Hanna et al. |

FOREIGN PATENT DOCUMENTS

| | | |
|---|---|---|
| WO | WO-1998031826 A1 | 7/1998 |
| WO | WO-03031464 A2 | 4/2003 |
| WO | WO-2013126587 A1 | 8/2013 |
| WO | WO-2015031654 A2 | 3/2015 |
| WO | WO-2016081834 A2 | 5/2016 |

OTHER PUBLICATIONS

Bhattacharjee, et al. The conformation-dependent interaction of alpha 2-macroglobulin with vascular endothelial growth factor. A novel mechanism of alpha 2-macroglobulin/growth factor binding. J Biol Chem. Sep. 1, 2000;275(35):26806-11.
Borth, W. Alpha 2-macroglobulin. A multifunctional binding and targeting protein with possible roles in immunity and autoimmunity. Ann N Y Acad Sci. Sep. 10, 1994;737:267-72.
Browning, et al. Platelet-rich plasma increases matrix metalloproteinases in cultures of human synovial fibroblasts. J Bone Joint Surg Am. Dec. 5, 2012;94(23):e1721-7. doi: 10.2106/JBJS.K.01501.
Cuellar, et al. Is there a chondroprotective effect of autologous protease inhibitor concentrate on an osteoarthritis rabbit model? A pilot study. 11th Annual Pain Medicine Meeting. Miami, Florida. Nov. 15, 2012.
Final Office Action dated Jul. 17, 2019 for U.S. Appl. No. 15/910,477.
Fosang—ADAMTS-5: the story so far. Eur Cell Mater. Feb. 5, 2008;15:11-26.
Henikoff, et al. Amino acid substitution matrices from protein blocks. Proc Natl Acad Sci U S A. Nov. 15, 1992;89(22):10915-9.
Holtet et al., Receptor-binding domain of human α2-macroglobulin Expression, folding and biochemical characterization of a high-affinity recombinant derivative, FEBS Letters, 344: 242-246 (1994).
International search report and written opinion dated Aug. 7, 2013 for PCT/US2013/027159.
International Search Report and Written Opinion dated Jun. 10, 2016 for International Application No. PCT/US2015/061852.

(Continued)

*Primary Examiner* — Suzanne M Noakes
(74) *Attorney, Agent, or Firm* — Wilson Sonsini Goodrich & Rosati

(57) ABSTRACT

A2M polypeptide compositions containing a non-natural bait region are disclosed. Methods of producing wild-type and variant A2M polypeptides and polynucleotides containing a non-natural bait region are also disclosed. The bait regions of the variant A2M polypeptides demonstrate enhanced protease inhibitory characteristics compared to wild-type A2M. Variant A2M polypeptides that demonstrate longer half-lives upon administration to an organism compared to wild-type A2M are disclosed. The A2M compositions are useful in treating a number of diseases and conditions including inflammation, chronic wounds, and diseases with a pathology associated with proteases.

20 Claims, 23 Drawing Sheets

Specification includes a Sequence Listing.

(56) References Cited

OTHER PUBLICATIONS

Kimmel, et al. Preparation of cDNA and the generation of cDNA libraries: overview. Methods Enzymol. 1987;152:307-16.
Masters, et al. Effects of nitric oxide releasing poly(vinyl alcohol) hydrogel dressings on dermal wound healing in diabetic mice. Wound Repair Regen. Sep.-Oct. 2002;10(5):286-94.
Needleman, et al. A general method applicable to the search for similarities in the amino acid sequence of two proteins. J Mol Biol. Mar. 1970;48(3):443-53.
Non-Final OA dated Aug. 27, 2019 for U.S. Appl. No. 15/910,491.
Non-natural bait region of a variant A2M protein, SEQ ID 47, XP002778335, retrieved from EBI Accession No. GSP:BAS63734.
Notice of Allowance dated Dec. 8, 2018 for U.S. Appl. No. 14/380,234.
Notice of Allowance dated May 29, 2019 for U.S. Appl. No. 15/528,387.
Office Action dated Mar. 5, 2019 for U.S. Appl. No. 15/910,477.
Sottrup-Jensen, et al., The alpha-macroglobulin bait region. Sequence diversity and localization of cleavage sites for proteinases in five mammalian alpha-macroglobulins, J. Biol Chem, vol. 264, No. 27, Sep. 25, 1989, pp. 15781-15789.
Sottrup-Jensen, Lars, et al., Primary Structure of Human a2-Macroglobulin V. the complete Structure, The J Biological Chemistry, vol. 259, No. 13, Jul. 10, 1984, pp. 8318-8327.
Twining, SS. Fluorescein isothiocyanate-labeled casein assay for proteolytic enzymes. Anal Biochem. Nov. 15, 1984;143(1):30-4.
Zhang, Yang et al., Targeted designed variants of alpha-2-macroglobulin (A2M) attenuate cartilage degeneration in a rat model of osteoarthritis induced by anterior cruciate ligament transection, Arthritis Research & Therapy, vol. 19, No. 1, Jul. 25, 2017 XP055452623.

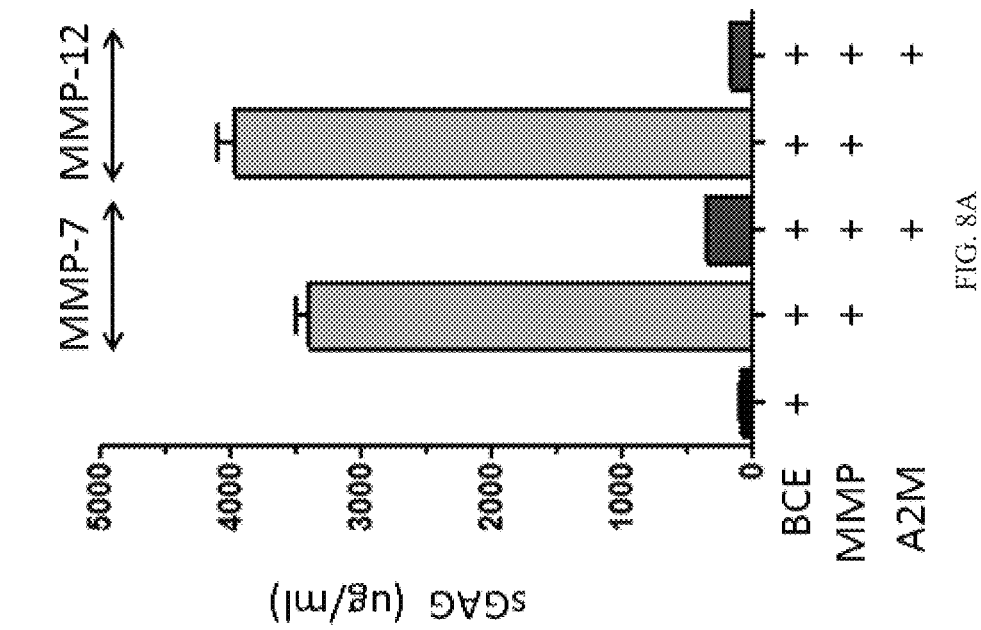
FIG. 8A
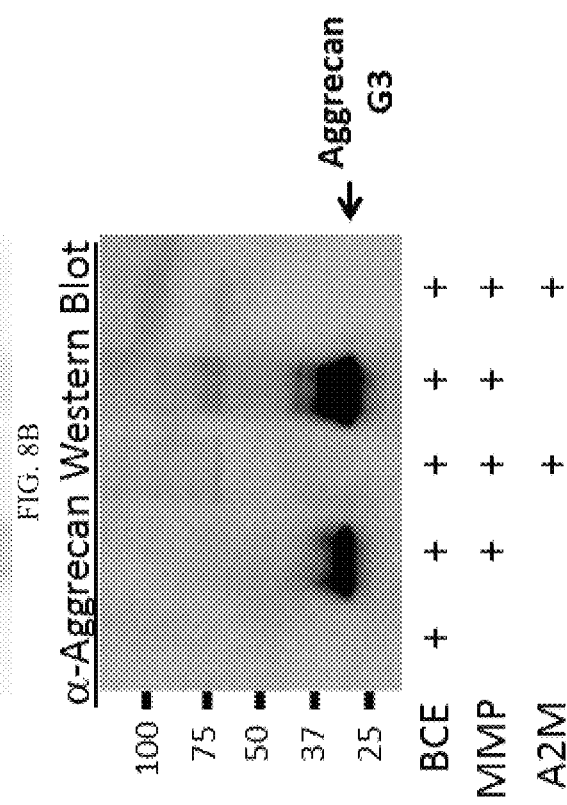
FIG. 8B
FIG. 8C

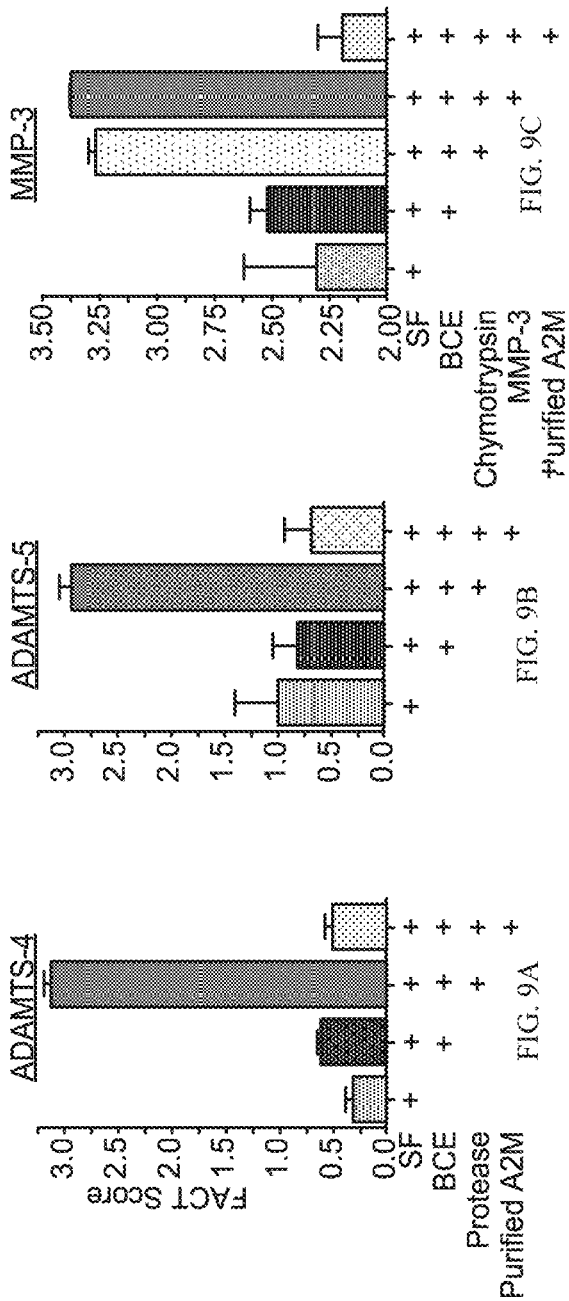
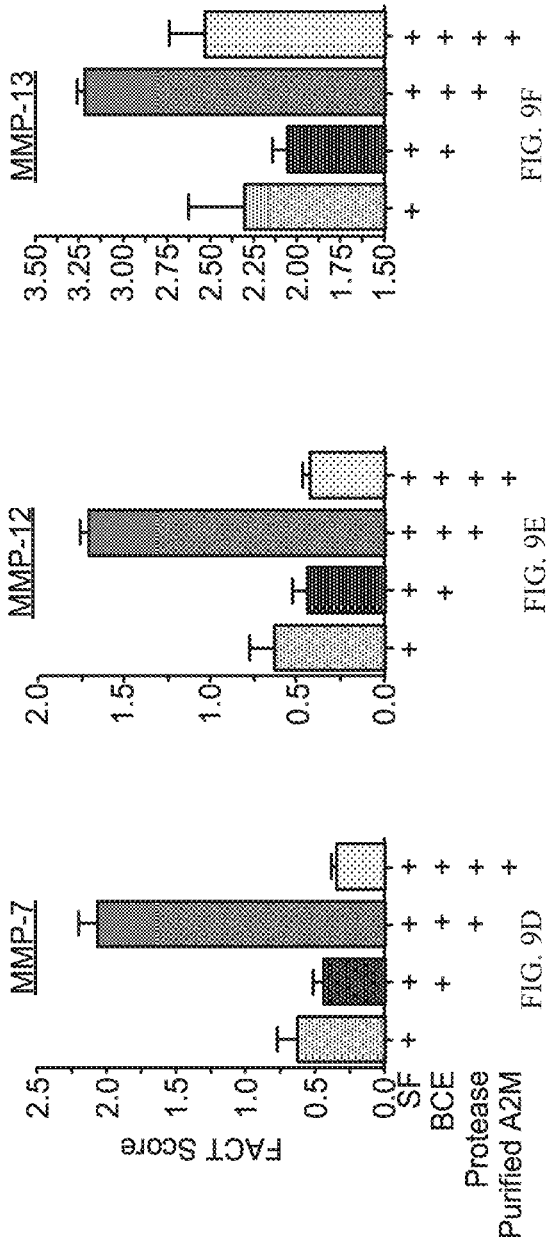

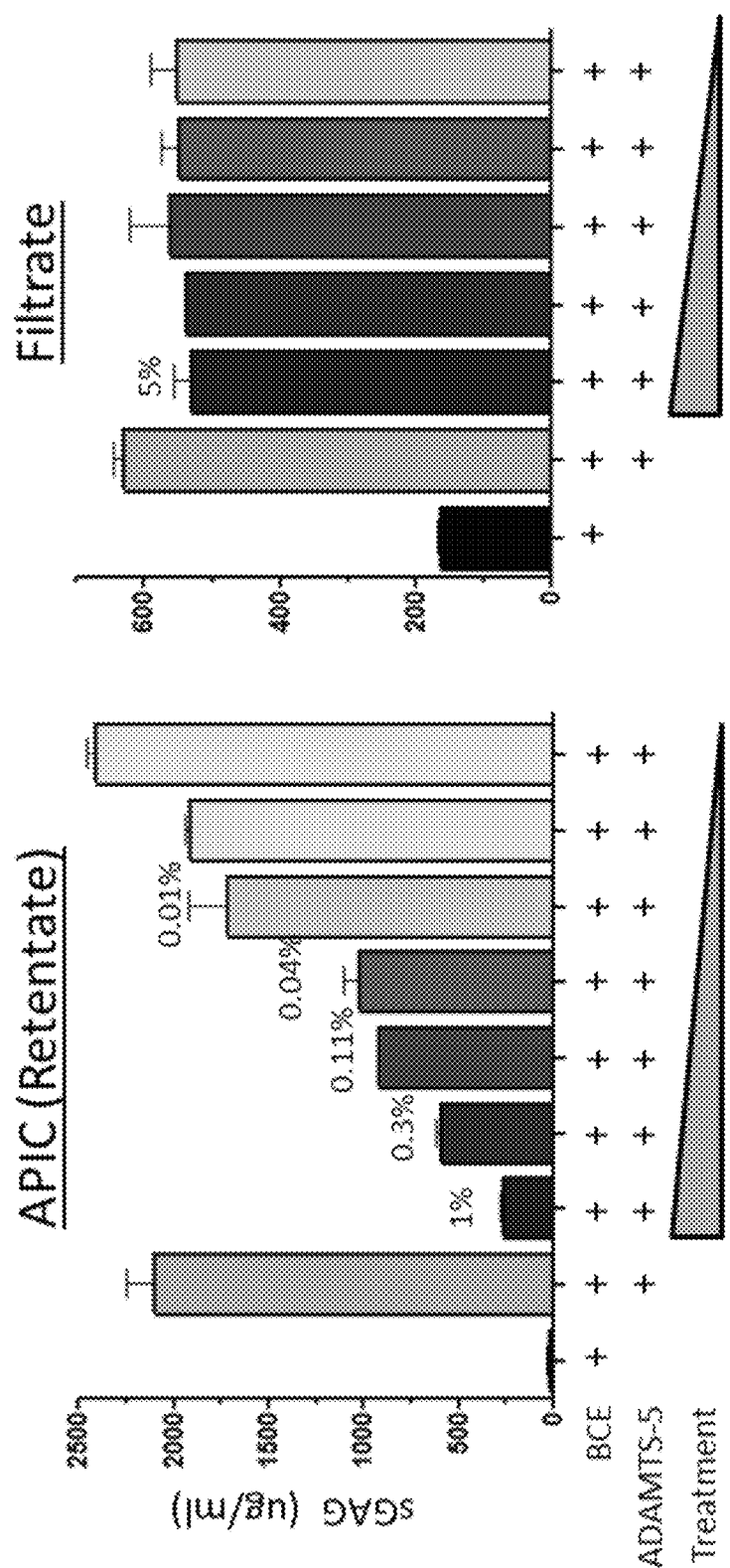

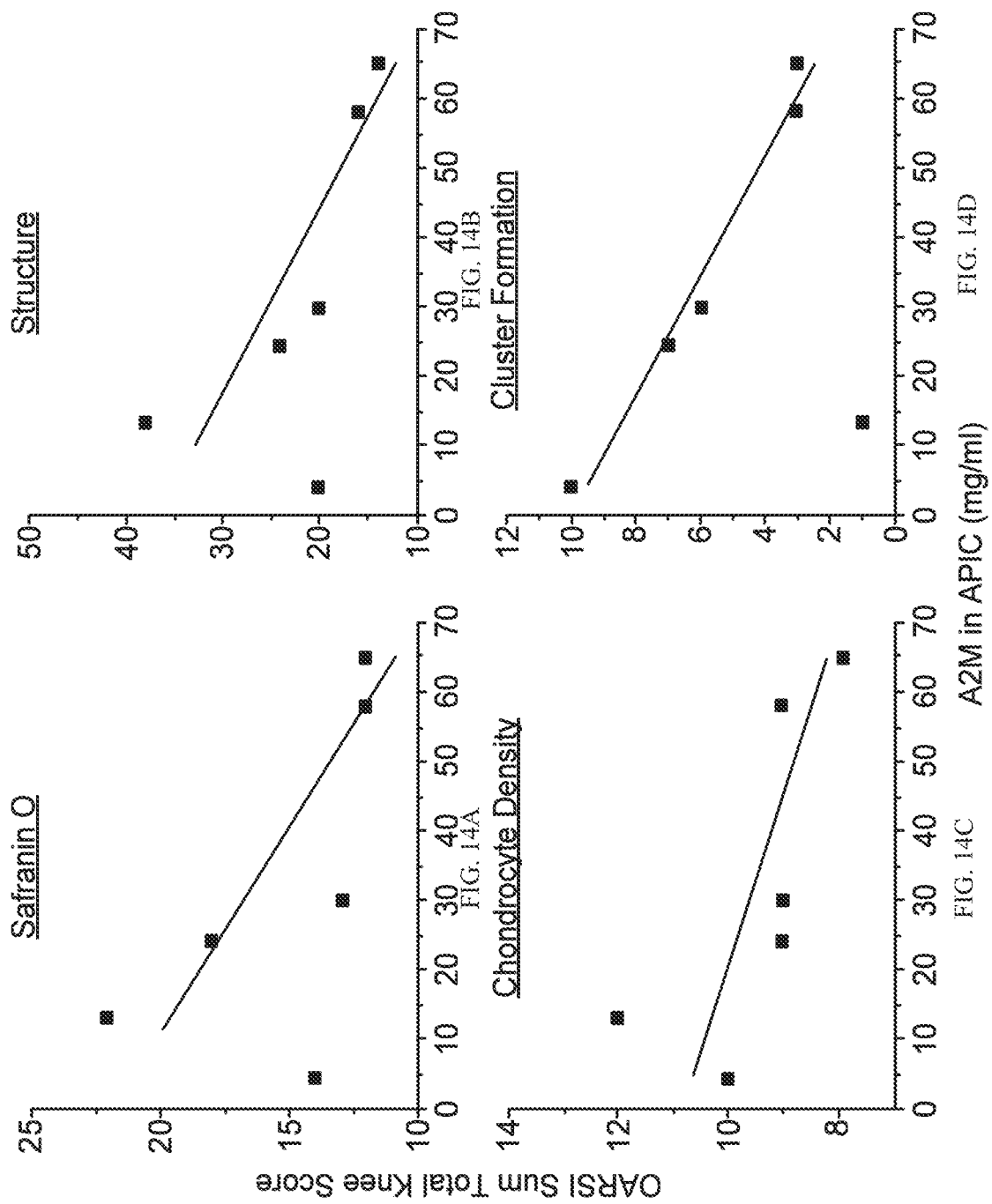

|  | TS4 | TS5 | MMP1 | MMP2* | MMP3 | MMP8 | MMP9* | MMP12** | MMP13 | Cath K | Trypsin | Chymo |
|---|---|---|---|---|---|---|---|---|---|---|---|---|
| APL34 | 202 | 314 | 154 | 109 | 118 | 100 | 121 | 100 | 185 | 100 | 100 | 100 |
| APL43 | 75 | 140 | 344 | 115 | 394 | 100 | 81 | 100 | 350 | 100 | 100 | 100 |
| APL52 | 95 | 355 | 197 | 120 | 394 | 100 | 66 | 100 | 867 | 100 | 100 | 71 |
| APL54 | 100 | 435 | 106 | 116 | 122 | 100 | 113 | 100 | 770 | 100 | 100 | 80 |

\* MMP2 cuts IgG poorly, leading to low differentiation between variants
\*\* MMP8 and MMP12 were completely inhibited by WT and all variants, so no difference could be determined
\*\*\* MMP9 cleaved IgG does not show up an Western, so quantitation was done on remaining intact IgG only, which is less accurate

Bait sequences:

APL34   LEQYEMHGPEGCLRVCEGEGEGFYESDVMGRGHARLVWEEPHTKL

APL43   LEQYEMHGPEGCLRVCEAIPMSIPTSEDIVVQIPENFEGVKL

APL52   LEQYEMHGPEGCLRVCKEKEGLGSIPENFEGVSELEGRGSKL

APL54   LEQYEMHGPEGCLRVCSELEGRGSFYESDVMGRGHARLVWEEPHTKL

FIG. 20

SEQUENCE LISTING

```
<160> NUMBER OF SEQ ID NOS: 155

<210> SEQ ID NO 1
<211> LENGTH: 8993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ctcatgacca aaatccctta acgtgagtta cgcgcgcgtc gttccactga gcgtcagacc       60
ccgtagaaaa gatcaaagga tcttcttgag atccttttt tctgcgcgta atctgctgct      120
tgcaaacaaa aaaaccaccg ctaccagcgg tggtttgttt gccggatcaa gagctaccaa      180 ctcttttcc gaaggtaact ggcttcagca gagcgcagat accaaatact gttcttctag      240
tgtagccgta gttagcccac cacttcaaga actctgtagc accgcctaca tacctcgctc      300
```

```
tgctaatcct gttaccagtg gctgctgcca gtggcgataa gtcgtgtctt accgggttgg    360
actcaagacg atagttaccg gataaggcgc agcggtcggg ctgaacgggg ggttcgtgca    420
cacagcccag cttggagcga acgacctaca ccgaactgag atacctacag cgtgagctat    480
gagaaagcgc cacgcttccc gaagggagaa aggcggacag gtatccggta agcggcaggg    540
tcggaacagg agagcgcacg agggagcttc caggggaaa cgcctggtat ctttatagtc    600
ctgtcgggtt tcgccacctc tgacttgagc gtcgattttt gtgatgctcg tcagggggc    660 ggagcctatg gaaaaacgcc agcaacgcgg ccttttttacg gttcctggcc ttttgctggc    720
cttttgctca catgttcttt cctgcgttat ccctgattc tgtggataac cgtattaccg    780
cctttgagtg agctgatacc gctcgccgca gccgaacgac cgagcgcagc gagtcagtga    840
gcgaggaagc ggaaggcgag gtagggaac tgccaggcat caaactaagc agaaggcccc    900
tgacggatgg cctttttgcg tttctacaaa ctctttctgt gttgtaaaac gacggccagt    960
cttaagctcg ggccccctgg gcggttctga taacgagtaa tcgttaatcc gcaaataacg   1020
taaaaacccg cttcggcggg tttttttatg gggggagttt agggaaagag catttgtcag   1080
aatatttaag ggcgcctgtc actttgcttg atatatgaga attatttaac cttataaatg   1140 agaaaaagc aacgcacttt aaataagata cgttgctttt tcgattgatg aacacctata   1200
attaaactat tcatctatta tttatgattt tttgtatata caatatttct agtttgttaa   1260
agagaattaa gaaataaat ctcgaaaata ataagggaa atcagtttt tgatatcaaa   1320 attatacatg tcaacgataa tacaaaatat aatacaaact ataagatgtt atcagtattt   1380
attatcattt agaataaatt ttgtgtcgcc cttaattgtg agcggataac aattacgagc   1440
ttcatgcaca gtggcgttga cattgattat tgactagtta ttaatagtaa tcaattacgg   1500
ggtcattagt tcatagccca tatatggagt tccgcgttac ataacttacg gtaaatggcc   1560
cgcctggctg accgcccaac gaccccgcc cattgacgtc aataatgacg tatgttccca   1620
tagtaacgcc aatagggact ttccattgac gtcaatgggt ggagtatta cggtaaactg   1680 cccacttggc agtacatcaa gtgtatcata tgccaagtac gccccctatt gacgtcaatg   1740
acggtaaatg gcccgcctgg cattatgccc agtacatgac cttatgggac tttcctactt   1800
ggcagtacat ctacgtatta gtcatcgcta ttaccatggt gatgcggttt tggcagtaca   1860
tcaatgggcg tggatagcgg tttgactcac ggggatttcc aagtctccac cccattgacg   1920
tcaatgggag tttgttttgg caccaaaatc aacgggactt tccaaaatgt cgtaacaact   1980
ccgccccatt gacgcaaatg ggcggtaggc gtgtacggtg gaggtctat ataagcagag   2040 ctctctggct aactagagaa cccactgctt actggcttat cgaaattaat acgactcact   2100
ataggggtac ctgccaccat ggggaaaaac aaactgctgc atccaagcct ggtcctgctg   2160
ctgctggttc tgctgcctac tgacgcctct gtgagcggaa agccccagta tatggttctg   2220
gtcccgtccc tgctgcacac cgagaccaca gaaaaagggt gcgtgctgct gtcttacctg   2280
aatgaaacag tgactgttag tgcctcactg agagtgtgc gcggaaatcg ttcactgttc   2340
accgatctgg aggcggaaaa cgatgtgctg cattgcgtcg catttgctgt gccaaaaagc   2400
tcctctaatg aagaagtgat gttcctgacc gtccaggtga agggccctac acaggaattc   2460
aaaaaacgca ctaccgttat ggtcaaaaac gaggatagcc tggtgtttgt tcagacagac   2520
aaatccatct ataagcctgg tcagactgtg aagttccggg tggttagcat ggatgaaaat   2580
tttcaccccc tgaacgagct gattccactg gtgtacatcc aggaccctaa aggcaaccgc   2640
```

```
atcgcccagt ggcagtcttt ccagctggaa ggcggtctga agcagtttag tttccctctg    2700
agttcagagc cgtttcaggg ttcttataaa gtcgtggttc agaaaaagag tggggggacgt    2760
actgaacatc ctttttaccgt tgaagagttc gtcctgccga aatttgaggt ccaggtgacc    2820
gttcccaaga ttatcacaat tctggaagag gaaatgaacg tgagcgtgtg cggactgtat    2880
acctacggca aaccagtgcc tggtcacgtt acagtcagta tctgccgtaa gtactcagat    2940
gcaagcgact gtcatggcga agattccag gcttttttgcg agaagttcag cggccagctg    3000
aactcccacg gttgcttcta tcagcaggtg aaaaccaagg tttttcagct gaaacggaag    3060
gagtacgaaa tgaaactgca tacagaagcc cagattcagg aagaaggcac cgtcgtggaa    3120
ctgactggtc gtcagagctc cgagattacc cggacaatca ctaaactgag cttcgtgaag    3180
gttgattccc actttcggca ggggattccc ttttttcggac aggtgcgcct ggttgacggg    3240
aaaggagttc cgatccccaa caaagtgatc tttattcgcg gcaatgaagc caactattac    3300
agcaacgcga caactgatga gcatgggctg gtgcagttca gtatcaatac cacaaacgtg    3360
atgggaacct cactgacagt ccgcgtgaat tataaagacc gttcaccgtg ttatggctac    3420
cagtgggtga gcgaggaaca cgaggaagcc caccataccg cgtacctggt tttcagcccc    3480
tccaaatctt ttgtccatct ggaacctatg tctcacgagc tgccgtgcgg ccatacccag    3540
acagtgcagg cacattatat tctgaacggc ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt    3720
gctccggtcg cccgtctgct gatctatgcc gtgctgccaa ccggcgatgt tatcggtgac    3780
tccgccaaat acgatgtgga gaattgtctg gcgaacaagg ttgacctgag cttttccccc    3840
tctcagagtc tgccagcgtc tcatgcacat ctgcgtgtga ccgcagcccc tcagagcgtt    3900
tgcgctctgc gtgcagtgga tcagtccgtg ctgctgatga agccagacgc agaactgtct    3960
gctagcagcg tgtataatct gctgcctgag aaagatctga ccgggttccc aggacctctg    4020
aacgatcagg atgacgaaga ctgtattaat cgccacaacg tgtatattaa tgggatcaca    4080
tacactccgg tttcaagcac caacgaaaaa gatatgtaca gcttcctgga ggacatgggt    4140
ctgaaagcgt ttaccaattc caagatccgg aaacccaaga tgtgcccaca gctgcagcag    4200
tatgaaatgc acggacctga gggtctgcgt gtgggctttt acgaatctga tgtgatggga    4260
cgtggtcatg cacgtctggt tcatgtcgag gaaccacaca ccgaaacagt gcgtaaatac    4320
ttccctgaga cctggatttg ggacctggtt gtggtgaact ccgcgggtgt ggcagaagtg    4380
ggtgttaccg tcccggatac tattaccgaa tggaaagcag gtgccttctg tctgtctgag    4440
gatgcagggc tgggaatctc ctctacagcc tctctgcgcg cgtttcagcc cttttttcgtc    4500
gaactgacta tgccatatag cgtgattcgt ggcgaggcat tcactctgaa agctaccgtg    4560
ctgaattacc tgcccaagtg catccgcgtg agcgtgcagc tggaagctag tcccgccttt    4620
ctggcggtcc cagtggagaa ggaacaggca ccgcactgca tttgtgctaa cggccggcag    4680
actgtttcct gggccgtcac ccccaaatct ctgggtaatg tgaacttcac cgtttcagca    4740
gaggctctgg aaagccagga gctgtgcggc accgaagtcc catccgtgcc tgagcatggt    4800
cgcaaagata cagtcatcaa gcctctgctg gttgaaccgg aaggcctgga aaggaaaact    4860
acctttaatt ctctgctgtg cccaagtggc ggtgaagtgt ccgaggaact gtctctgaaa    4920
ctgccgccca acgtggtcga ggaatctgcc cgtgcgtcag ttagcgtcct gggggatatt    4980
ctgggaagtg ccatgcagaa tacccagaac ctgctgcaga tgccgtatgg ctgtggcgag    5040
```

```
cagaatatgg ttctgtttgc gcccaacatc tatgtcctgg attacctgaa tgaaacacag    5100
cagctgactc ctgaaatcaa aagcaaggca atcgggtatc tgaataccgg ataccagcgg    5160
cagctgaact ataagcacta cgacggctcc tattctacct tcggcgaacg gtacggtcgc    5220
aatcagggga acacttggct gaccgccttt gtgctgaaaa cctttgccca ggctcgcgcc    5280
tatatcttta ttgatgaggc ccatattaca caggcgctga tctggctgtc acagcgccag    5340
aaggacaacg ggtgtttccg tagttcagga agcctgctga acaatgccat caaaggcggc    5400
gtcgaggatg aagtgacact gagcgcatac attactatcg ctctgctgga aatccctctg    5460
acagtgactc acccggtggt tcgcaatgct ctgttttgcc tggaaagtgc atggaaaaca    5520
gctcaggaag gcgatcacgg atcacacgtg tatactaagg cactgctggc gtacgcattc    5580
gctctggccg gcaaccagga taaacgtaaa gaagtgctga atcactgaa tgaggaagca     5640 gttaaaaagg acaacagcgt ccactgggaa cggccgcaga acccaaggc tccagtgggt     5700 cacttttatg agcctcaggc accgagtgct gaggtgaaaa tgacctcata tgttctgctg    5760
gcatacctga ccgcacagcc tgcccccaca tcagaagatc tgacaagcgc cactaatatt    5820
gtgaaatgga tcaccaagca gcagaacgcg cagggcggtt ttagctccac ccaggacaca    5880
gtcgtggcac tgcacgctct gtctaaatat ggggcagcta ccttcacacg cactggaaag    5940
gccgcgcaag tgactattca gtcagtggc accttttcaa gcaagttcca ggtggataac     6000
aataaccgtc tgctgctgca gcaggtgtcc ctgcccgaac tgccaggcga gtactctatg    6060
aaagtcactg gggaaggatg cgtgtatctg cagacctccc tgaaatacaa tattctgccc    6120 gagaagaag aatttccatt cgcactgggc gtgcagaccc tgcctcagac atgcgatgaa     6180
ccgaaggctc atacttcttt tcagatcagt ctgtcagtga gctataccgg gtcccgctct    6240
gccagtaaca tggcgattgt ggatgtgaaa atggtgagtg gattcatccc tctgaaaccg    6300
actgtgaaga tgctggaacg gagtaatcac gtttcacgca ccgaggtctc ctctaaccat    6360
gtgctgatct acctggataa agtgtccaat cagacactgt ctctgttttt cactgtgctg    6420
caggatgtcc ccgtgcgtga cctgaaacca gccattgtta aggtctatga ttattacgaa    6480
accgacgagt tcgcgatcgc agaatacaac gcgccgtgca gcaaagacct ggggaatgct    6540
gactacaagg acgacgacga caagggggca agccaccacc atcaccatca ctaaggatcc    6600
aaaatcagcc tcgactgtgc cttctagttg ccagccatct gttgtttgcc cctccccgt     6660 gccttccttg accctggaag gtgccactcc cactgtcctt tcctaataaa atgaggaaat    6720
tgcatcacaa cactcaaccc tatctcggtc tattcttttg atttataagg gattttgccg    6780
atttcggcct attggttaaa aaatgagctg atttaacaaa aatttaacgc gaattaattc    6840
tgtggaatgt gtgtcagtta gggtgtggaa agtccccagg ctccccagca ggcagaagta    6900
tgcaaagcat gcatctcaat tagtcagcaa ccaggtgtgg aaagtcccca ggctccccag    6960
caggcagaag tatgcaaagc atgcatctca attagtcagc aaccatagtc ccgcccctaa    7020
ctccgcccat cccgccccta actccgccca gttccgccca ttctccgccc catggctgac    7080 taatttttttt tatttatgca gaggccgagg ccgcctctgc ctctgagcta ttccagaagt    7140
agtgaggagg cttttttgga ggcctaggct tttgcaaaaa gctcccggga gcttgtatat    7200 ccatttttcgg atctgatcag cacgtgttga caattaatca tcggcatagt atatcggcat    7260
agtataatac gacaaggtga ggaactaaac catggccaag cctttgtctc aagaagaatc    7320
caccctcatt gaaagagcaa cggctacaat caacagcatc cccatctctg aagactacag    7380
```

| | |
|---|---|
| cgtcgccagc gcagctctct ctagcgacgg ccgcatcttc actggtgtca atgtatatca | 7440 |
| ttttactggg ggaccttgtg cagaactcgt ggtgctgggc actgctgctg ctgcggcagc | 7500 |
| tggcaacctg acttgtatcg tcgcgatcgg aaatgagaac aggggcatct tgagcccctg | 7560 |
| cggacggtgc cgacaggtgc ttctcgatct gcatcctggg atcaaagcca tagtgaagga | 7620 |
| cagtgatgga cagccgacgg cagttgggat tcgtgaattg ctgccctctg gttatgtgtg | 7680 |
| ggagggctaa cacgtgctac gagatttcga ttccaccgcc gccttctatg aaaggttggg | 7740 |
| cttcggaatc gttttccggg acgccggctg gatgatcctc cagcgcgggg atctcatgct | 7800 |
| ggagttcttc gcccacccca acttgtttat tgcagcttat aatggttaca ataaagcaa | 7860 |
| tagcatcaca aatttcacaa ataaagcatt tttttcactg cattctagtt gtggtttgtc | 7920 |
| caaactcatc aatgtatctt atcatgtctg tataccgtcg acctctagct agagcttggc | 7980 |
| gtaatcatgg tcattaccaa tgcttaatca gtgaggcacc tatctcagcg atctgtctat | 8040 |
| ttcgttcatc catagttgcc tgactccccg tcgtgtagat aactacgata cgggagggct | 8100 |
| taccatctgg ccccagcgct gcgatgatac cgcgagaacc acgctcaccg gctccggatt | 8160 |
| tatcagcaat aaaccagcca gccggaaggg ccgagcgcag aagtggtcct gcaactttat | 8220 |
| ccgcctccat ccagtctatt aattgttgcc gggaagctag agtaagtagt tcgccagtta | 8280 |
| atagtttgcg caacgttgtt gccatcgcta caggcatcgt ggtgtcacgc tcgtcgtttg | 8340 |
| gtatggcttc attcagctcc ggttcccaac gatcaaggcg agttacatga tcccccatgt | 8400 |
| tgtgcaaaaa agcggttagc tccttcggtc ctccgatcgt tgtcagaagt aagttggccg | 8460 |
| cagtgttatc actcatggtt atggcagcac tgcataattc tcttactgtc atgccatccg | 8520 |
| taagatgctt ttctgtgact ggtgagtact caaccaagtc attctgagaa tagtgtatgc | 8580 |
| ggcgaccgag ttgctcttgc ccggcgtcaa tacgggataa taccgcgcca catagcagaa | 8640 |
| ctttaaaagt gctcatcatt ggaaaacgtt cttcggggcg aaaactctca aggatcttac | 8700 |
| cgctgttgag atccagttcg atgtaaccca ctcgtgcacc caactgatct tcagcatctt | 8760 |
| ttactttcac cagcgtttct gggtgagcaa aaacaggaag gcaaaatgcc gcaaaaaagg | 8820 |
| gaataagggc gacacggaaa tgttgaatac tcatattctt ccttttttcaa tattattgaa | 8880 |
| gcatttatca gggttattgt ctcatgagcg gatacatatt tgaatgtatt tagaaaaata | 8940 |
| aacaaatagg ggtcagtgtt acaaccaatt aaccaattct gaacattatc gcg | 8993 |

<210> SEQ ID NO 2
<211> LENGTH: 8994
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

| | |
|---|---|
| ctcatgacca aaatccctta acgtgagtta cgcgcgcgtc gttccactga gcgtcagacc | 60 |
| ccgtagaaaa gatcaaagga tcttcttgag atcctttttt tctgcgcgta atctgctgct | 120 |
| tgcaaacaaa aaaaccaccg ctaccagcgg tggtttgttt gccggatcaa gagctaccaa | 180 |
| ctcttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg ctgctgccag tggcgataa gtcgtgtctt accgggttgg | 360 |
| actcaagacg atagttaccg gataaggcgc agcggtcggg ctgaacgggg ggttcgtgca | 420 |

```
cacagcccag cttggagcga acgacctaca ccgaactgag atacctacag cgtgagctat    480
gagaaagcgc cacgcttccc gaagggagaa aggcggacag gtatccggta agcggcaggg    540
tcggaacagg agagcgcacg agggagcttc caggggggaaa cgcctggtat ctttatagtc   600
ctgtcgggtt tcgccacctc tgacttgagc gtcgattttt gtgatgctcg tcaggggggc   660
ggagcctatg gaaaaacgcc agcaacgcgg ccttttttacg gttcctggcc ttttgctggc   720
cttttgctca catgttcttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg cctttttgcg tttctacaaa ctctttctgt gttgtaaaac gacggccagt    960
cttaagctcg gcccccctgg gcggttctga taacgagtaa tcgttaatcc gcaaataacg   1020
taaaaacccg cttcggcggg ttttttttatg gggggagttt agggaaagag catttgtcag   1080
aatatttaag ggcgcctgtc actttgcttg atatatgaga attatttaac cttataaatg   1140 agaaaaagc aacgcacttt aaataagata cgttgctttt tcgattgatg aacacctata   1200
attaaactat tcatctatta tttatgattt tttgtatata caatatttct agtttgttaa    1260
agagaattaa gaaaataaat ctcgaaaata ataaagggaa aatcagtttt tgatatcaaa    1320
attatacatg tcaacgataa tacaaaatat aatacaaact ataagatgtt atcagtattt    1380
attatcattt agaataaatt ttgtgtcgcc cttaattgtg agcggataac aattacgagc    1440
ttcatgcaca gtggcgttga cattgattat tgactagtta ttaatagtaa tcaattacgg    1500
ggtcattagt tcatagccca tatatggagt tccgcgttac ataacttacg gtaaatggcc    1560
cgcctggctg accgcccaac gacccccgcc cattgacgtc aataatgacg tatgttccca    1620
tagtaacgcc aatagggact ttccattgac gtcaatgggt ggagtattta cggtaaactg    1680
cccacttggc agtacatcaa gtgtatcata tgccaagtac gccccctatt gacgtcaatg    1740
acggtaaatg gcccgcctgg cattatgccc agtacatgac cttatgggac tttcctactt    1800
ggcagtacat ctacgtatta gtcatcgcta ttaccatggt gatgcggttt tggcagtaca    1860
tcaatgggcg tggatagcgg tttgactcac ggggatttcc aagtctccac cccattgacg    1920
tcaatgggag tttgttttgg caccaaaatc aacgggactt tccaaaatgt cgtaacaact    1980
ccgccccatt gacgcaaatg ggcggtaggc gtgtacggtg ggaggtctat ataagcagag    2040
ctctctggct aactagagaa cccactgctt actggcttat cgaaattaat acgactcact    2100
ataggggtac ctgccaccat ggggaaaaac aaactgctgc atccaagcct ggtcctgctg    2160
ctgctggttc tgctgcctac tgacgcctct gtgagcggaa agccccagta tatggttctg    2220
gtcccgtccc tgctgcacac cgagaccaca gaaaaagggt gcgtgctgct gtcttacctg    2280
aatgaaacag tgactgttag tgcctcactg gagagtgtgc gcggaaatcg ttcactgttc    2340
accgatctgg aggcggaaaa cgatgtgctg cattgcgtcg catttgctgt gccaaaaagc    2400
tcctctaatg aagaagtgat gttcctgacc gtccaggtga agggccctac acaggaattc    2460
aaaaaacgca ctaccgttat ggtcaaaaac gaggatagcc tggtgtttgt tcagacagac    2520
aaatccatct ataagcctgg tcagactgtg aagttccggg tggttagcat ggatgaaaat    2580
tttcaccccc tgaacgagct gattccactg gtgtacatcc aggaccctaa aggcaaccgc    2640
atcgcccagt ggcagtcttt ccagctggaa ggcggtctga agcagtttag tttccctctg    2700
agttcagagc cgtttcaggg ttcttataaa gtcgtggttc agaaaaagag tggggggacgt    2760 actgaacatc cttttaccgt tgaagagttc gtcctgccga aatttgaggt ccaggtgacc    2820
```

```
gttcccaaga ttatacaat tctggaagag gaaatgaacg tgagcgtgtg cggactgtat    2880
acctacggca aaccagtgcc tggtcacgtt acagtcagta tctgccgtaa gtactcagat    2940
gcaagcgact gtcatggcga agattcacag gcttttttgcg agaagttcag cggccagctg   3000
aactcccacg gttgcttcta tcagcaggtg aaaaccaagg tttttcagct gaaacgaag    3060 gagtacgaaa tgaaactgca tacagaagcc cagattcagg aagaaggcac cgtcgtggaa   3120
ctgactggtc gtcagagctc cgagattacc cggacaatca ctaaactgag cttcgtgaag   3180
gttgattccc actttcggca ggggattccc tttttcggac aggtgcgcct ggttgacggg   3240
aaaggagttc cgatccccaa caaagtgatc tttattcgcg gcaatgaagc caactattac   3300
agcaacgcga caactgatga gcatgggctg gtgcagttca gtatcaatac cacaaacgtg   3360
atgggaacct cactgacagt ccgcgtgaat tataaagacc gttcaccgtg ttatggctac   3420
cagtgggtga gcgaggaaca cgaggaagcc caccataccg cgtacctggt tttcagcccc   3480
tccaaatctt ttgtccatct ggaacctatg tctcacgagc tgccgtgcgg ccataccag    3540 acagtgcagg cacattatat tctgaacggc ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt   3720
gctccggtcg cccgtctgct gatctatgcc gtgctgccaa ccggcgatgt tatcggtgac   3780
tccgccaaat acgatgtgga gaattgtctg gcgaacaagg ttgacctgag cttttccccc   3840
tctcagagtc tgccagcgtc tcatgcacat ctgcgtgtga ccgcagcccc tcagagcgtt    3900
tgcgctctgc gtgcagtgga tcagtccgtg ctgctgatga gccagacgc agaactgtct    3960 gctagcagcg tgtataatct gctgcctgag aaagatctga ccgggttccc aggacctctg   4020
aacgatcagg atgacgaaga ctgtattaat cgccacaacg tgtatattaa tgggatcaca   4080
tacactccgg tttcaagcac caacgaaaaa gatatgtaca gcttcctgga ggacatgggt   4140
ctgaaagcgt ttaccaattc caagatccgg aaacccaag atgtgcccac agctcgagca   4200
gtatgaaatg cacggacctg agggtctgcg tgtgggcttt tacgaatctg atgtgatggg   4260
acgtggtcat gcacgtctgg ttcatgtcga ggaaccacac accgaaaagc ttcgtaaata   4320
cttccctgag acctggattt gggacctggt tgtggtgaac tccgcgggtg tggcagaagt   4380
gggtgttacc gtcccggata ctattaccga atggaaagca ggtgccttct gtctgtctga   4440
ggatgcaggg ctgggaatct cctctacagc ctctctgcgc gcgtttcagc ccttttttcgt    4500 cgaactgact atgccatata gcgtgattcg tggcgaggca ttcactctga aagctaccgt    4560
gctgaattac ctgcccaagt gcatccgcgt gagcgtgcag ctggaagcta gtcccgcctt   4620
tctggcggtc ccagtggaga aggaacaggc accgcactgc atttgtgcta acggccggca   4680 gactgttttcc tgggccgtca ccccaaatc tctgggtaat gtgaacttca ccgtttcagc   4740
agaggctctg gaaagccagg agctgtgcgg caccgaagtc ccatccgtgc ctgagcatgg   4800
tcgcaaagat acagtcatca agcctctgct ggttgaaccg gaaggcctgg agaaggaaac   4860
tacctttaat tctctgctgt gcccaagtgg cggtgaagtg tccgaggaac tgtctctgaa    4920
actgccgccc aacgtggtcg aggaatctgc ccgtgcgtca gttagcgtcc tggggatat    4980 tctgggaagt gccatgcaga atacccagaa cctgctgcag atgccgtatg ctgtggcga    5040 gcagaatatg gttctgtttg cgcccaacat ctatgtcctg gattacctga atgaaacaca   5100
gcagctgact cctgaaatca aaagcaaggc aatcgggtat ctgaataccg gataccagcg   5160
```

```
gcagctgaac tataagcact acgacggctc ctattctacc ttcggcgaac ggtacggtcg    5220
caatcagggg aacacttggc tgaccgcctt tgtgctgaaa acctttgccc aggctcgcgc    5280
ctatatcttt attgatgagg cccatattac acaggcgctg atctggctgt cacagcgcca    5340
gaaggacaac gggtgtttcc gtagttcagg aagcctgctg aacaatgcca tcaaaggcgg    5400
cgtcgaggat gaagtgacac tgagcgcata cattactatc gctctgctgg aaatccctct    5460
gacagtgact cacccggtgg ttcgcaatgc tctgttttgc ctggaaagtg catgaaaaac    5520
agctcaggaa ggcgatcacg gatcacacgt gtatactaag gcactgctgg cgtacgcatt    5580
cgctctggcc ggcaaccagg ataaacgtaa agaagtgctg aaatcactga atgaggaagc    5640
agttaaaaag gacaacagcg tccactggga acggccgcag aaacccaagg ctccagtggg    5700
tcacttttat gagcctcagg caccgagtgc tgaggtggaa atgacctcat atgttctgct    5760
ggcatacctg accgcacagc ctgccccac atcagaagat ctgacaagcg ccactaatat    5820
tgtgaaatgg atcaccaagc agcagaacgc gcagggcggt tttagctcca cccaggacac    5880
agtcgtggca ctgcacgctc tgtctaaata tggggcagct accttcacac gcactggaaa    5940
ggccgcgcaa gtgactattc agtctagtgg caccttttca gcaagttcc aggtggataa    6000 caataaccgt ctgctgctgc agcaggtgtc cctgcccgaa ctgccaggcg agtactctat    6060
gaaagtcact ggggaaggat gcgtgtatct gcagacctcc ctgaaataca atattctgcc    6120
cgagaaagaa gaatttccat tcgcactggg cgtgcagacc ctgcctcaga catgcgatga    6180
accgaaggct catacttctt ttcagatcag tctgtcagtg agctataccg gtcccgctc    6240 tgccagtaac atggcgattg tggatgtgaa aatggtgagt ggattcatcc ctctgaaacc    6300
gactgtgaag atgctggaac ggagtaatca cgtttcacgc accgaggtct cctctaacca    6360
tgtgctgatc tacctggata agtgtccaa tcagacactg tctctgtttt tcactgtgct    6420
gcaggatgtc cccgtgcgtg acctgaaacc agccattgtt aaggtctatg attattacga    6480
aaccgacgag ttcgcgatcg cagaatacaa cgcgccgtgc agcaaagacc tggggaatgc    6540
tgactacaag gacgacgacg acaaggggc aagccaccac catcaccatc actaaggatc    6600
caaaatcagc ctcgactgtg ccttctagtt gccagccatc tgttgtttgc ccctcccccg    6660
tgccttcctt gaccctggaa ggtgccactc ccactgtcct ttcctaataa atgaggaaa    6720 ttgcatcaca acactcaacc ctatctcggt ctattctttt gatttataag ggattttgcc    6780
gatttcggcc tattggttaa aaatgagct gatttaacaa aaatttaacg cgaattaatt    6840
ctgtggaatg tgtgtcagtt agggtgtgga aagtccccag gctccccagc aggcagaagt    6900
atgcaaagca tgcatctcaa ttagtcagca accaggtgtg gaaagtcccc aggctcccca    6960
gcaggcagaa gtatgcaaag catgcatctc aattagtcag caaccatagt cccgccccta    7020
actccgccca tcccgcccct aactccgccc agttccgccc attctccgcc ccatggctga    7080
ctaatttttt ttatttatgc agaggccgag gccgcctctg cctctgagct attccagaag    7140
tagtgaggag gcttttttgg aggcctaggc ttttgcaaaa agctcccggg agcttgtata    7200
tccattttcg gatctgatca gcacgtgttg acaattaatc atcggcatag tatatcggca    7260
tagtataata cgacaaggtg aggaactaaa ccatggccaa gcctttgtct caagaagaat    7320
ccaccctcat tgaaagagca acggctacaa tcaacagcat cccatctct gaagactaca    7380 gcgtcgccag cgcagctctc tctagcgacg gccgcatctt cactggtgtc aatgtatatc    7440
attttactgg gggaccttgt gcagaactcg tggtgctggg cactgctgct gctgcggcag    7500
ctggcaacct gacttgtatc gtcgcgatcg gaaatgagaa caggggcatc ttgagcccct    7560
```

```
gcggacggtg ccgacaggtg cttctcgatc tgcatcctgg gatcaaagcc atagtgaagg    7620
acagtgatgg acagccgacg gcagttggga ttcgtgaatt gctgccctct ggttatgtgt    7680
gggagggcta acacgtgcta cgagatttcg attccaccgc cgccttctat gaaaggttgg    7740
gcttcggaat cgttttccgg gacgccggct ggatgatcct ccagcgcggg gatctcatgc    7800
tggagttctt cgcccacccc aacttgttta ttgcagctta taatggttac aaataaagca    7860
atagcatcac aaatttcaca aataaagcat ttttttcact gcattctagt tgtggtttgt    7920
ccaaactcat caatgtatct tatcatgtct gtataccgtc gacctctagc tagagcttgg    7980
cgtaatcatg gtcattacca atgcttaatc agtgaggcac ctatctcagc gatctgtcta    8040
tttcgttcat ccatagttgc ctgactcccc gtcgtgtaga taactacgat acgggagggc    8100
ttaccatctg gccccagcgc tgcgatgata ccgcgagaac cacgctcacc ggctccggat    8160
ttatcagcaa taaaccagcc agccggaagg gccgagcgca gaagtggtcc tgcaacttta    8220
tccgcctcca tccagtctat taattgttgc cgggaagcta gagtaagtag ttcgccagtt    8280
aatagtttgc gcaacgttgt tgccatcgct acaggcatcg tggtgtcacg ctcgtcgttt    8340
ggtatggctt cattcagctc cggttcccaa cgatcaaggc gagttacatg atcccccatg    8400
ttgtgcaaaa aagcggttag ctccttcggt cctccgatcg ttgtcagaag taagttggcc    8460
gcagtgttat cactcatggt tatggcagca ctgcataatt ctcttactgt catgccatcc    8520
gtaagatgct tttctgtgac tggtgagtac tcaaccaagt cattctgaga atagtgtatg    8580
cggcgaccga gttgctcttg cccggcgtca atacgggata ataccgcgcc acatagcaga    8640
actttaaaag tgctcatcat tggaaaacgt tcttcgggc gaaaactctc aaggatctta    8700
ccgctgttga gatccagttc gatgtaaccc actcgtgcac ccaactgatc ttcagcatct    8760
tttactttca ccagcgtttc tgggtgagca aaaacaggaa ggcaaaatgc cgcaaaaaag    8820
ggaataaggg cgacacggaa atgttgaata ctcatattct cctttttca atattattga    8880 agcatttatc agggttattg tctcatgagc ggatacatat ttgaatgtat ttagaaaaat    8940
aaacaaatag ggtcagtgt tacaaccaat taaccaattc tgaacattat cgcg           8994
```

<210> SEQ ID NO 3  
<211> LENGTH: 1491  
<212> TYPE: PRT  
<213> ORGANISM: Homo sapiens

<400> SEQUENCE: 3

```
Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
```

```
            115                 120                 125
Val Phe Val Gln Thr Asp Lys Ser Ile Tyr Lys Pro Gly Gln Thr Val
            130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
            165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
            195                 200                 205

Lys Lys Ser Gly Gly Arg Thr Glu His Pro Phe Thr Val Glu Glu Phe
            210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
            245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
            275                 280                 285

Lys Phe Ser Gly Gln Leu Asn Ser His Gly Cys Phe Tyr Gln Gln Val
            290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
            325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
            355                 360                 365

Val Arg Leu Val Asp Gly Lys Gly Val Pro Ile Pro Asn Lys Val Ile
            370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
            405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
            435                 440                 445

Tyr Leu Val Phe Ser Pro Ser Lys Ser Phe Val His Leu Glu Pro Met
            450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
            485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
            530                 535                 540
```

```
Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
            565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
        610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
        690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
        930                 935                 940

Arg Ala Ser Val Ser Val Leu Gly Asp Ile Leu Gly Ser Ala Met Gln
945                 950                 955                 960
```

```
Asn Thr Gln Asn Leu Leu Gln Met Pro Tyr Gly Cys Gly Glu Gln Asn
            965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
            995                 1000                1005

Asn Thr Gly Tyr Gln Arg Gln Leu Asn Tyr Lys His Tyr Asp Gly
        1010                1015                1020

Ser Tyr Ser Thr Phe Gly Glu Arg Tyr Gly Arg Asn Gln Gly Asn
        1025                1030                1035

Thr Trp Leu Thr Ala Phe Val Leu Lys Thr Phe Ala Gln Ala Arg
        1040                1045                1050

Ala Tyr Ile Phe Ile Asp Glu Ala His Ile Thr Gln Ala Leu Ile
        1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Gly Val Glu Asp Glu
        1085                1090                1095

Val Thr Leu Ser Ala Tyr Ile Thr Ile Ala Leu Leu Glu Ile Pro
        1100                1105                1110

Leu Thr Val Thr His Pro Val Val Arg Asn Ala Leu Phe Cys Leu
        1115                1120                1125

Glu Ser Ala Trp Lys Thr Ala Gln Glu Gly Asp His Gly Ser His
        1130                1135                1140

Val Tyr Thr Lys Ala Leu Leu Ala Tyr Ala Phe Ala Leu Ala Gly
        1145                1150                1155

Asn Gln Asp Lys Arg Lys Glu Val Leu Lys Ser Leu Asn Glu Glu
        1160                1165                1170

Ala Val Lys Lys Asp Asn Ser Val His Trp Glu Arg Pro Gln Lys
        1175                1180                1185

Pro Lys Ala Pro Val Gly His Phe Tyr Glu Pro Gln Ala Pro Ser
        1190                1195                1200

Ala Glu Val Glu Met Thr Ser Tyr Val Leu Leu Ala Tyr Leu Thr
        1205                1210                1215

Ala Gln Pro Ala Pro Thr Ser Glu Asp Leu Thr Ser Ala Thr Asn
        1220                1225                1230

Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys
        1250                1255                1260

Tyr Gly Ala Ala Thr Phe Thr Arg Thr Gly Lys Ala Ala Gln Val
        1265                1270                1275

Thr Ile Gln Ser Ser Gly Thr Phe Ser Ser Lys Phe Gln Val Asp
        1280                1285                1290

Asn Asn Asn Arg Leu Leu Leu Gln Gln Val Ser Leu Pro Glu Leu
        1295                1300                1305

Pro Gly Glu Tyr Ser Met Lys Val Thr Gly Glu Gly Cys Val Tyr
        1310                1315                1320

Leu Gln Thr Ser Leu Lys Tyr Asn Ile Leu Pro Glu Lys Glu Glu
        1325                1330                1335

Phe Pro Phe Ala Leu Gly Val Gln Thr Leu Pro Gln Thr Cys Asp
        1340                1345                1350

Glu Pro Lys Ala His Thr Ser Phe Gln Ile Ser Leu Ser Val Ser
```

```
                1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala Asp Tyr Lys Asp Asp Asp Lys Gly Ala Ser His His His
    1475                1480                1485

His His His
    1490

<210> SEQ ID NO 4
<211> LENGTH: 1491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
                20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
        50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205
```

-continued

```
Lys Lys Ser Gly Gly Arg Thr Glu His Pro Phe Thr Val Glu Glu Phe
    210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                    245                 250                 255
Gly Lys Pro Val Pro Gly His Val Thr Val Ser Ile Cys Arg Lys Tyr
                260                 265                 270
Ser Asp Ala Ser Asp Cys His Gly Glu Asp Ser Gln Ala Phe Cys Glu
            275                 280                 285
Lys Phe Ser Gly Gln Leu Asn Ser His Gly Cys Phe Tyr Gln Gln Val
290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Gly Thr Val Val Glu Leu Thr
                    325                 330                 335
Gly Arg Gln Ser Ser Glu Ile Thr Arg Thr Ile Thr Lys Leu Ser Phe
                340                 345                 350
Val Lys Val Asp Ser His Phe Arg Gln Gly Ile Pro Phe Phe Gly Gln
                355                 360                 365
Val Arg Leu Val Asp Gly Lys Gly Val Pro Ile Pro Asn Lys Val Ile
370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                    405                 410                 415
Thr Ser Leu Thr Val Arg Val Asn Tyr Lys Asp Arg Ser Pro Cys Tyr
                420                 425                 430
Gly Tyr Gln Trp Val Ser Glu Glu His Glu Glu Ala His His Thr Ala
                435                 440                 445
Tyr Leu Val Phe Ser Pro Ser Lys Ser Phe Val His Leu Glu Pro Met
    450                 455                 460
Ser His Glu Leu Pro Cys Gly His Thr Gln Thr Val Gln Ala His Tyr
465                 470                 475                 480
Ile Leu Asn Gly Gly Thr Leu Gly Leu Lys Lys Leu Ser Phe Tyr
                485                 490                 495
Tyr Leu Ile Met Ala Lys Gly Gly Ile Val Arg Thr Gly Thr His Gly
                500                 505                 510
Leu Leu Val Lys Gln Glu Asp Met Lys Gly His Phe Ser Ile Ser Ile
                515                 520                 525
Pro Val Lys Ser Asp Ile Ala Pro Val Ala Arg Leu Leu Ile Tyr Ala
    530                 535                 540
Val Leu Pro Thr Gly Asp Val Ile Gly Asp Ser Ala Lys Tyr Asp Val
545                 550                 555                 560
Glu Asn Cys Leu Ala Asn Lys Val Asp Leu Ser Phe Ser Pro Ser Gln
                565                 570                 575
Ser Leu Pro Ala Ser His Ala His Leu Arg Val Thr Ala Ala Pro Gln
                580                 585                 590
Ser Val Cys Ala Leu Arg Ala Val Asp Gln Ser Val Leu Leu Met Lys
                595                 600                 605
Pro Asp Ala Glu Leu Ser Ala Ser Ser Val Tyr Asn Leu Leu Pro Glu
    610                 615                 620
Lys Asp Leu Thr Gly Phe Pro Gly Pro Leu Asn Asp Gln Asp Asp Glu
```

-continued

```
            625                 630                 635                 640
        Asp Cys Ile Asn Arg His Asn Val Tyr Ile Asn Gly Ile Thr Tyr Thr
                        645                 650                 655
        Pro Val Ser Ser Thr Asn Glu Lys Asp Met Tyr Ser Phe Leu Glu Asp
                        660                 665                 670
        Met Gly Leu Lys Ala Phe Thr Asn Ser Lys Ile Arg Lys Pro Lys Met
                        675                 680                 685
        Cys Pro Gln Leu Glu Gln Tyr Glu Met His Gly Pro Glu Gly Leu Arg
                        690                 695                 700
        Val Gly Phe Tyr Glu Ser Asp Val Met Gly Arg Gly His Ala Arg Leu
        705                 710                 715                 720
        Val His Val Glu Glu Pro His Thr Glu Lys Leu Arg Lys Tyr Phe Pro
                        725                 730                 735
        Glu Thr Trp Ile Trp Asp Leu Val Val Asn Ser Ala Gly Val Ala
                        740                 745                 750
        Glu Val Gly Val Thr Val Pro Asp Thr Ile Thr Glu Trp Lys Ala Gly
                        755                 760                 765
        Ala Phe Cys Leu Ser Glu Asp Ala Gly Leu Gly Ile Ser Ser Thr Ala
                        770                 775                 780
        Ser Leu Arg Ala Phe Gln Pro Phe Phe Val Glu Leu Thr Met Pro Tyr
        785                 790                 795                 800
        Ser Val Ile Arg Gly Glu Ala Phe Thr Leu Lys Ala Thr Val Leu Asn
                        805                 810                 815
        Tyr Leu Pro Lys Cys Ile Arg Val Ser Val Gln Leu Glu Ala Ser Pro
                        820                 825                 830
        Ala Phe Leu Ala Val Pro Val Glu Lys Glu Gln Ala Pro His Cys Ile
                        835                 840                 845
        Cys Ala Asn Gly Arg Gln Thr Val Ser Trp Ala Val Thr Pro Lys Ser
                        850                 855                 860
        Leu Gly Asn Val Asn Phe Thr Val Ser Ala Glu Ala Leu Glu Ser Gln
        865                 870                 875                 880
        Glu Leu Cys Gly Thr Glu Val Pro Ser Val Pro Glu His Gly Arg Lys
                        885                 890                 895
        Asp Thr Val Ile Lys Pro Leu Leu Val Glu Pro Glu Gly Leu Glu Lys
                        900                 905                 910
        Glu Thr Thr Phe Asn Ser Leu Leu Cys Pro Ser Gly Gly Glu Val Ser
                        915                 920                 925
        Glu Glu Leu Ser Leu Lys Leu Pro Pro Asn Val Val Glu Glu Ser Ala
        930                 935                 940
        Arg Ala Ser Val Ser Val Leu Gly Asp Ile Leu Gly Ser Ala Met Gln
        945                 950                 955                 960
        Asn Thr Gln Asn Leu Leu Gln Met Pro Tyr Gly Cys Gly Glu Gln Asn
                        965                 970                 975
        Met Val Leu Phe Ala Pro Asn Ile Tyr Val Leu Asp Tyr Leu Asn Glu
                        980                 985                 990
        Thr Gln Gln Leu Thr Pro Glu Ile Lys Ser Lys Ala Ile Gly Tyr Leu
                        995                 1000                1005
        Asn Thr Gly Tyr Gln Arg Gln Leu Asn Tyr Lys His Tyr Asp Gly
                1010                1015                1020
        Ser Tyr Ser Thr Phe Gly Glu Arg Tyr Gly Arg Asn Gln Gly Asn
                1025                1030                1035
        Thr Trp Leu Thr Ala Phe Val Leu Lys Thr Phe Ala Gln Ala Arg
                1040                1045                1050
```

-continued

```
Ala Tyr Ile Phe Ile Asp Glu Ala His Ile Thr Gln Ala Leu Ile
1055                1060                1065

Trp Leu Ser Gln Arg Gln Lys Asp Asn Gly Cys Phe Arg Ser Ser
1070                1075                1080

Gly Ser Leu Leu Asn Asn Ala Ile Lys Gly Gly Val Glu Asp Glu
1085                1090                1095

Val Thr Leu Ser Ala Tyr Ile Thr Ile Ala Leu Leu Glu Ile Pro
1100                1105                1110

Leu Thr Val Thr His Pro Val Val Arg Asn Ala Leu Phe Cys Leu
1115                1120                1125

Glu Ser Ala Trp Lys Thr Ala Gln Glu Gly Asp His Gly Ser His
1130                1135                1140

Val Tyr Thr Lys Ala Leu Leu Ala Tyr Ala Phe Ala Leu Ala Gly
1145                1150                1155

Asn Gln Asp Lys Arg Lys Glu Val Leu Lys Ser Leu Asn Glu Glu
1160                1165                1170

Ala Val Lys Lys Asp Asn Ser Val His Trp Glu Arg Pro Gln Lys
1175                1180                1185

Pro Lys Ala Pro Val Gly His Phe Tyr Glu Pro Gln Ala Pro Ser
1190                1195                1200

Ala Glu Val Glu Met Thr Ser Tyr Val Leu Leu Ala Tyr Leu Thr
1205                1210                1215

Ala Gln Pro Ala Pro Thr Ser Glu Asp Leu Thr Ser Ala Thr Asn
1220                1225                1230

Ile Val Lys Trp Ile Thr Lys Gln Gln Asn Ala Gln Gly Gly Phe
1235                1240                1245

Ser Ser Thr Gln Asp Thr Val Val Ala Leu His Ala Leu Ser Lys
1250                1255                1260

Tyr Gly Ala Ala Thr Phe Thr Arg Thr Gly Lys Ala Ala Gln Val
1265                1270                1275

Thr Ile Gln Ser Ser Gly Thr Phe Ser Ser Lys Phe Gln Val Asp
1280                1285                1290

Asn Asn Asn Arg Leu Leu Leu Gln Gln Val Ser Leu Pro Glu Leu
1295                1300                1305

Pro Gly Glu Tyr Ser Met Lys Val Thr Gly Glu Gly Cys Val Tyr
1310                1315                1320

Leu Gln Thr Ser Leu Lys Tyr Asn Ile Leu Pro Glu Lys Glu Glu
1325                1330                1335

Phe Pro Phe Ala Leu Gly Val Gln Thr Leu Pro Gln Thr Cys Asp
1340                1345                1350

Glu Pro Lys Ala His Thr Ser Phe Gln Ile Ser Leu Ser Val Ser
1355                1360                1365

Tyr Thr Gly Ser Arg Ser Ala Ser Asn Met Ala Ile Val Asp Val
1370                1375                1380

Lys Met Val Ser Gly Phe Ile Pro Leu Lys Pro Thr Val Lys Met
1385                1390                1395

Leu Glu Arg Ser Asn His Val Ser Arg Thr Glu Val Ser Ser Asn
1400                1405                1410

His Val Leu Ile Tyr Leu Asp Lys Val Ser Asn Gln Thr Leu Ser
1415                1420                1425

Leu Phe Phe Thr Val Leu Gln Asp Val Pro Val Arg Asp Leu Lys
1430                1435                1440
```

```
Pro Ala  Ile Val Lys Val Tyr Asp Tyr Tyr Glu Thr  Asp Glu Phe
    1445                 1450                 1455

Ala Ile  Ala Glu Tyr Asn Ala Pro Cys Ser Lys Asp  Leu Gly Asn
    1460                 1465                 1470

Ala Asp  Tyr Lys Asp Asp Asp Lys Gly Ala Ser  His His His
    1475                 1480                 1485

His His  His
    1490

<210> SEQ ID NO 5
<211> LENGTH: 41
<212> TYPE: PRT
<213> ORGANISM: Homo sapiens

<400> SEQUENCE: 5

Pro Gln Leu Gln Gln Tyr Glu Met His Gly Pro Glu Gly Leu Arg Val
1               5                   10                  15

Gly Phe Tyr Glu Ser Asp Val Met Gly Arg Gly His Ala Arg Leu Val
            20                  25                  30

His Val Glu Glu Pro His Thr Glu Thr
        35                  40

<210> SEQ ID NO 6
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Glu His Gly Pro Glu Gly Glu Gly Glu Gly Ile Pro Glu
1               5                   10                  15

Asn Phe Tyr Gly Val Ser Glu Asp Leu Val Val Gln Ile Ser Glu Leu
            20                  25                  30

Glu Gly Arg Gly Ser Val Glu Glu Pro His Thr Lys Leu
        35                  40                  45

<210> SEQ ID NO 7
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Glu His Gly Pro Glu Gly Glu Gly Glu Gly Ile Pro Glu
1               5                   10                  15

Asn Phe Phe Gly Val Arg Tyr Ser Glu Asp Leu Val Val Gln Ile Ser
            20                  25                  30

Glu Leu Glu Gly Arg Gly Ser Val Glu Glu Pro His Thr Lys Leu
        35                  40                  45

<210> SEQ ID NO 8
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

```
Leu Glu His Gly Pro Glu Gly Glu Gly Glu Gly Gly Ile Pro Glu
1               5                   10                  15

Asn Phe Phe Gly Val Leu Tyr Ser Glu Asp Leu Val Val Gln Ile Ser
            20                  25                  30

Glu Leu Glu Gly Arg Gly Ser Val Glu Pro His Thr Lys Leu
        35                  40                  45
```

<210> SEQ ID NO 9
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Leu Glu His Gly Pro Glu Gly Glu Gly Glu Gly Gly Ile Pro Glu
1               5                   10                  15

Asn Phe Phe Gly Val Pro Arg Tyr Leu Ser Glu Asp Leu Val Val Gln
            20                  25                  30

Ile Ser Glu Leu Glu Gly Arg Gly Ser Val Glu Glu Pro His Thr Lys
        35                  40                  45

Leu
```

<210> SEQ ID NO 10
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Leu Glu His Gly Pro Glu Gly Glu Gly Leu Gly Glu Gly Ile Pro Glu
1               5                   10                  15

Asn Phe Tyr Gly Val Ser Glu Asp Leu Val Val Gln Ile Ser Glu Leu
            20                  25                  30

Glu Gly Arg Gly Ser Val Glu Glu Pro His Thr Lys Leu
        35                  40                  45
```

<210> SEQ ID NO 11
<211> LENGTH: 49
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Leu Glu His Gly Pro Glu Gly Glu Gly Glu Gly Pro Arg Tyr Leu Thr
1               5                   10                  15

Ala Ile Pro Glu Asn Phe Phe Gly Val Ser Glu Asp Leu Val Val Gln
            20                  25                  30

Ile Ser Glu Leu Glu Gly Arg Gly Ser Val Glu Glu Pro His Thr Lys
        35                  40                  45

Leu
```

<210> SEQ ID NO 12
<211> LENGTH: 46
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 12

Leu Glu His Gly Pro Glu Gly Glu Gly Glu Gly Ile Pro Glu Asn
1               5                   10                  15

Phe Glu Phe Arg Gly Val Ser Glu Asp Leu Val Val Gln Ile Ser Glu
                20                  25                  30

Leu Glu Gly Arg Gly Ser Val Glu Pro His Thr Lys Leu
            35                  40                  45

<210> SEQ ID NO 13
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Glu His Gly Pro Arg Tyr Leu Thr Ala Glu Gly Glu Gly Glu Gly
1               5                   10                  15

Ile Pro Glu Asn Phe Phe Gly Val Ser Glu Asp Leu Val Val Gln Ile
                20                  25                  30

Ser Glu Leu Glu Gly Arg Gly Ser Val Glu Pro His Thr Lys Leu
            35                  40                  45

<210> SEQ ID NO 14
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Glu His Gly Pro Glu Gly Glu Gly Glu Gly Gly Ile Pro Arg
1               5                   10                  15

Tyr Leu Thr Ala Glu Asn Phe Phe Gly Val Ser Glu Asp Leu Val Val
                20                  25                  30

Gln Ile Ser Glu Leu Glu Gly Arg Gly Ser Val Glu Glu Pro His Thr
            35                  40                  45

Lys Leu
    50

<210> SEQ ID NO 15
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Glu His Gly Pro Glu Gly Glu Gly Glu Gly Glu Gly Ile Pro Glu
1               5                   10                  15

Asn Phe Phe Gly Val Ser Glu Asp Leu Val Val Gln Ile Ser Glu Leu
                20                  25                  30

Glu Gly Arg Gly Ser Arg Tyr Leu Thr Ala Val Glu Glu Pro His Thr
            35                  40                  45

Lys Leu
```

<210> SEQ ID NO 16
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Glu His Gly Pro Glu Phe Arg Gly Val Thr Arg Tyr Leu Thr Ala
1               5                   10                  15

Ile Pro Glu Asn Phe Tyr Gly Val Ser Glu Leu Glu Gly Arg Gly Ser
            20                  25                  30

Ser Glu Asp Leu Val Val Gln Ile Val Glu Glu Pro His Thr Lys Leu
        35                  40                  45

<210> SEQ ID NO 17
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Glu His Gly Pro Thr Glu Gly Glu Ala Arg Gly Ser Ile Pro Glu
1               5                   10                  15

Asn Phe Tyr Gly Val Ser Glu Asp Leu Val Val Gln Ile Ser Glu Leu
            20                  25                  30

Glu Gly Arg Gly Ser Val Glu Glu Pro His Thr Lys Leu
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Glu His Gly Pro Ile Pro Glu Asn Phe Tyr Gly Leu Glu Gly Glu
1               5                   10                  15

Gly Glu Gly Glu Gly Glu Ala Ile Pro Met Ser Ile Pro Arg Tyr Leu
            20                  25                  30

Thr Ala Glu Phe Arg Gly Val Thr Val Glu Glu Pro His Thr Lys Leu
        35                  40                  45

<210> SEQ ID NO 19
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Glu His Gly Pro Glu Gly Glu Gly Glu Gly Glu Phe Arg Gly Val
1               5                   10                  15

Thr Ile Pro Glu Asn Phe Tyr Gly Val Ser Glu Asp Leu Val Val Gln
            20                  25                  30

Ile Ser Glu Leu Glu Gly Arg Gly Ser Val Glu Pro His Thr Lys
        35                  40                  45

Leu

<210> SEQ ID NO 20
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Glu His Gly Pro Glu Phe Arg Gly Val Thr Glu Gly Glu Gly Glu
1               5                   10                  15

Gly Ile Pro Glu Asn Phe Tyr Gly Val Ser Glu Asp Leu Val Val Gln
            20                  25                  30

Ile Ser Glu Leu Glu Gly Arg Gly Ser Val Glu Pro His Thr Lys
        35                  40                  45

Leu

<210> SEQ ID NO 21
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Glu His Gly Pro Thr Glu Gly Glu Ala Arg Gly Ser Pro Arg Tyr
1               5                   10                  15

Leu Thr Ala Ile Pro Glu Asn Phe Tyr Gly Val Ser Glu Asp Leu Val
            20                  25                  30

Val Gln Ile Ser Glu Leu Glu Gly Arg Gly Ser Pro His Thr Lys Leu
        35                  40                  45

<210> SEQ ID NO 22
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Glu His Gly Pro Glu Gly Glu Gly Glu Gly Glu Phe Arg Gly Val
1               5                   10                  15

Thr Ile Pro Glu Asn Phe Phe Gly Val Pro Arg Tyr Leu Thr Ala Ser
            20                  25                  30

Glu Asp Leu Val Val Gln Ile Ser Glu Leu Glu Gly Arg Gly Ser Pro
        35                  40                  45

His Thr Lys Leu
    50

<210> SEQ ID NO 23
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 23

Leu Glu His Gly Pro Ile Pro Glu Asn Phe Tyr Gly Val Glu Gly Glu
1               5                   10                  15

Gly Leu Gly Ile Gly Ser Glu Asp Leu Val Val Gln Ile Ser Glu Leu
                20                  25                  30

Glu Gly Arg Gly Ser Val Glu Glu Pro His Thr Lys Leu
            35                  40                  45

<210> SEQ ID NO 24
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Leu Glu His Gly Pro Ile Pro Glu Asn Phe Tyr Gly Val Glu Gly Glu
1               5                   10                  15

Gly Glu Gly Glu Gly Ser Glu Asp Leu Val Val Gln Ile Ser Glu Leu
                20                  25                  30

Glu Gly Arg Gly Ser Val Glu Glu Pro His Thr Lys Leu
            35                  40                  45

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Glu His Gly Pro Glu Gly Glu Gly Glu Gly Ile Pro Glu
1               5                   10                  15

Asn Phe Tyr Gly Val Ser Glu Asp Leu Tyr Thr Ala Ser Glu Leu Glu
                20                  25                  30

Gly Arg Gly Ser Val Glu Glu Pro His Thr Lys Leu
            35                  40

<210> SEQ ID NO 26
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Glu His Gly Pro Glu Gly Glu Gly Glu Gly Phe Arg Ala Ala
1               5                   10                  15

Pro Phe Leu Thr Ala Ile Pro Glu Asn Phe Phe Gly Val Ser Glu Asp
                20                  25                  30

Leu Val Val Gln Ile Ser Glu Leu Glu Gly Arg Gly Ser Pro His Thr
            35                  40                  45

Lys Leu
    50

<210> SEQ ID NO 27
<211> LENGTH: 48
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 27

Leu Glu Gln Tyr Glu Met His Gly Pro Glu Gly Glu Gly Gly Glu
1               5                   10                  15

Gly Ile Pro Glu Asn Phe Tyr Gly Val Ser Glu Asp Leu Tyr Thr Ala
            20                  25                  30

Ser Glu Leu Glu Gly Arg Gly Ser Val Glu Glu Pro His Thr Lys Leu
        35                  40                  45

<210> SEQ ID NO 28
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Glu Gln Tyr Glu Met His Gly Pro Glu Gly Glu Gly Gly Glu
1               5                   10                  15

Phe Arg Ala Ala Pro Phe Leu Thr Ala Ile Pro Glu Asn Phe Phe Gly
            20                  25                  30

Val Ser Glu Asp Leu Val Val Gln Ile Ser Glu Leu Glu Gly Arg Gly
        35                  40                  45

Ser Pro His Thr Lys Leu
    50

<210> SEQ ID NO 29
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Leu Glu Gln Pro Glu Gly Glu Gly Glu Gly Pro Arg Tyr Leu Thr Ala
1               5                   10                  15

Ile Pro Glu Asn Phe Phe Gly Val Ser Glu Asp Leu Val Val Gln Ile
            20                  25                  30

Ser Glu Leu Glu Gly Arg Gly Ser Val Glu Glu Pro His Thr Lys Leu
        35                  40                  45

<210> SEQ ID NO 30
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Glu Gln Tyr Glu Met His Gly Pro Glu Gly Glu Gly Gly Pro
1               5                   10                  15

Arg Tyr Leu Thr Ala Ile Pro Glu Asn Phe Phe Gly Val Ser Glu Asp
            20                  25                  30

Leu Val Val Gln Ile Ser Glu Leu Glu Gly Arg Gly Ser Pro His Thr
        35                  40                  45

Lys Leu
```

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ala Gln Glu Ala Gly Glu Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Ser Gln Glu Leu Gly Gln Arg
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Pro Glu Asn Phe Phe Gly Val
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Glu Asp Leu Val Val Gln Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Ala Ile Pro Met Ser Ile Pro Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Glu Leu Glu Gly Arg Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Glu Glu Gly Leu Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Glu Glu Gly Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ser Glu Ser Glu Gly
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Phe Glu Val Glu Gly
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ile Glu Glu Gly Gly
1               5

<210> SEQ ID NO 42

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Arg Glu Ser Thr Gly
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Arg Glu Ala Gln Gly
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Lys Glu Thr Gly Gly
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Arg Glu Ala Gln Gly
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Thr Glu Gly Arg Gly
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Glu Asn Glu Ala Gly Gly
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Pro Glu Ser Ser Gly
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Pro Glu Ser Ser Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Ser Glu Ser Glu Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Gly Glu Gln Glu Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Pro Glu Pro Glu Gly
1               5

<210> SEQ ID NO 53
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 53

Glu Arg Glu Ala Gln Gly
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Ala Glu Gly Thr Gly
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Phe Pro Glu Val Glu Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Glu Glu Gly Val Glu Glu Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ala Arg Gly Leu Glu Gly
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Pro Pro Gly Leu Ala Pro Gly
1               5
```

```
<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Tyr Pro Gly Ser Ser Arg Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Phe Ala Gly Leu Pro Asn Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Gly Ser Leu Leu Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Pro Ala Gly Ala Ala Arg Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Leu Glu Gly Gly Gly Gly Gly
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

```
Gly Gly Gly Gly Ser Leu Leu Gly
1               5
```

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Phe Phe Gly Phe Pro Ile Gly
1               5
```

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Glu Pro Ala Gly Ala Ala Arg Gly
1               5
```

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gly Asp Arg Gly Leu Pro Ile Gly
1               5
```

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Gly Glu Pro Glu Gly Ala Lys Gly
1               5
```

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gly Phe Lys Glu Gly Val Glu Gly
1               5
```

<210> SEQ ID NO 70
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 70

Gly Val Glu Gly Val Glu Leu Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Lys Glu Gly Val Glu Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Glu Arg Gly Val Leu Gly
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Gly Ser Leu Leu Gly
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Glu Gly Val Glu Glu Gly
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Lys Glu Gly Val Glu Gly
1               5
```

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Phe Lys Glu Gly Val Glu Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Glu Pro Glu Gly Ala Lys Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Glu Gly Glu Ala Arg Gly Ser
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Gly Glu Gly Glu Gly Glu Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Phe Arg Gly Val Thr
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 81

Pro Arg Tyr Leu Thr Ala
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Pro or Glu
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Gly or Glu
<220> FEATURE:
<221> NAME/KEY: MOD_RES
<222> LOCATION: (5)..(5)
<223> OTHER INFORMATION: Gly, Val, Leu, Ser, Ala, Phe or Thr
<220> FEATURE:
<221> NAME/KEY: MOD_RES
<222> LOCATION: (6)..(7)
<223> OTHER INFORMATION: Any amino acid

<400> SEQUENCE: 82

Xaa Xaa Xaa Xaa Xaa Xaa Xaa Gly
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Gly, Val, Glu, Ala, Thr, Ser, Gln, Pro, Asn or
      Asp
<220> FEATURE:
<221> NAME/KEY: MOD_RES
<222> LOCATION: (5)..(5)
<223> OTHER INFORMATION: Any amino acid

<400> SEQUENCE: 83

Glu Xaa Glu Xaa Xaa Gly
1               5

<210> SEQ ID NO 84
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Leu Glu Gln Tyr Glu Met His Gly Pro Glu Gly Leu Arg Val Gly Lys
1               5                   10                  15
```

Glu Glu Glu Gly Leu Gly Ser Ile Pro Glu Asn Phe Phe Gly Val Ser
            20                  25                  30

Glu Leu Glu Gly Arg Gly Ser Lys Leu
            35                  40

<210> SEQ ID NO 85
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Leu Glu Gln Tyr Glu Met His Gly Pro Glu Gly Leu Arg Val Gly Ile
1               5                   10                  15

Pro Glu Asn Phe Phe Gly Val Ser Glu Leu Gly Arg Gly Ser Lys
            20                  25                  30

Glu Glu Glu Gly Leu Gly Ser Lys Leu
            35                  40

<210> SEQ ID NO 86
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Leu Glu Gln Tyr Glu Met His Gly Pro Glu Gly Leu Arg Val Gly Ser
1               5                   10                  15

Glu Leu Glu Gly Arg Gly Ser Lys Glu Glu Glu Gly Leu Gly Ser Ile
            20                  25                  30

Pro Glu Asn Phe Phe Gly Val Lys Leu
            35                  40

<210> SEQ ID NO 87
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Leu Glu Gln Tyr Glu Met His Gly Pro Glu Gly Leu Arg Val Gly Lys
1               5                   10                  15

Glu Glu Glu Gly Leu Gly Ser Ser Glu Leu Glu Gly Arg Gly Ser Thr
            20                  25                  30

Ala Gln Glu Ala Gly Glu Gly Lys Leu
            35                  40

<210> SEQ ID NO 88
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Glu Gln Tyr Glu Met His Gly Pro Glu Gly Leu Arg Val Gly Ile

```
                1               5                   10                  15
Pro Glu Asn Phe Phe Gly Val Phe Tyr Glu Ser Asp Val Met Gly Arg
                20                  25                  30

Gly His Ala Arg Leu Val His Val Glu Glu Pro His Thr Lys Leu Leu
            35                  40                  45
```

<210> SEQ ID NO 89
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Leu Glu Gln Tyr Glu Met His Gly Pro Glu Gly Leu Arg Val Gly Lys
1               5                   10                  15

Glu Glu Glu Gly Leu Gly Ser Phe Tyr Glu Ser Asp Val Met Gly Arg
                20                  25                  30

Gly His Ala Arg Leu Val His Val Glu Glu Pro His Thr Lys Leu Leu
            35                  40                  45
```

<210> SEQ ID NO 90
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Leu Glu Gln Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
                20                  25                  30

Gly His Ala Arg Leu Val His Val Glu Glu Pro His Thr Lys Leu Leu
            35                  40                  45
```

<210> SEQ ID NO 91
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Leu Glu Gln Tyr Glu Met His Gly Pro Glu Gly Leu Arg Val Gly Glu
1               5                   10                  15

Ala Ile Pro Met Ser Ile Pro Phe Tyr Glu Ser Asp Val Met Gly Arg
                20                  25                  30

Gly His Ala Arg Leu Val His Val Glu Glu Pro His Thr Lys Leu Leu
            35                  40                  45
```

<210> SEQ ID NO 92
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Leu Glu Gln Tyr Glu Met His Gly Pro Glu Gly Leu Arg Val Gly Thr
1               5                   10                  15

Ala Gln Glu Ala Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 93
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Leu Glu Gln Tyr Glu Met His Gly Pro Glu Gly Leu Arg Val Gly Val
1               5                   10                  15

Ser Gln Glu Leu Gly Gln Arg Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 94
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Leu Glu Gln Tyr Glu Met His Gly Pro Glu Gly Leu Arg Val Gly Thr
1               5                   10                  15

Glu Gly Glu Ala Arg Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 95
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Leu Glu Gln Tyr Glu Met His Gly Pro Glu Gly Leu Arg Val Gly Thr
1               5                   10                  15

Ser Glu Asp Leu Val Val Gln Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 96
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 97
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Leu Glu Gln Tyr Glu Met His Gly Pro Glu Gly Leu Arg Val Gly Gly
1               5                   10                  15

Glu Glu Gly Val Glu Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 98
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Leu Glu Gln Tyr Glu Met His Gly Pro Glu Gly Leu Arg Val Gly Gly
1               5                   10                  15

Ala Arg Gly Leu Glu Gly Phe Tyr Glu Ser Asp Val Met Gly Arg Gly
            20                  25                  30

His Ala Arg Leu Val His Val Glu Glu Pro His Thr Lys Leu
        35                  40                  45

<210> SEQ ID NO 99
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Leu Glu Gln Tyr Glu Met His Gly Pro Glu Gly Leu Arg Val Gly Gly
1               5                   10                  15

Pro Pro Gly Leu Ala Pro Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 100
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 100

Leu Glu Gln Tyr Glu Met His Gly Pro Glu Gly Leu Arg Val Gly Gly
1               5                   10                  15

Glu Pro Glu Gly Ala Lys Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 101
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Glu Gln Tyr Glu Met His Gly Pro Glu Gly Leu Arg Val Gly Glu
1               5                   10                  15

Glu Glu Gly Gly Gly Phe Tyr Glu Ser Asp Val Met Gly Arg Gly His
            20                  25                  30

Ala Arg Leu Val His Val Glu Glu Pro His Thr Lys Leu
        35                  40                  45

<210> SEQ ID NO 102
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Leu Glu Gln Tyr Glu Met His Gly Pro Glu Gly Leu Arg Val Gly Gly
1               5                   10                  15

Tyr Pro Gly Ser Ser Arg Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 103
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Leu Glu Gln Tyr Glu Met His Gly Pro Glu Gly Leu Arg Val Gly Gly
1               5                   10                  15

Ala Arg Gly Leu Glu Gly Gly Phe Ala Gly Leu Pro Asn Gly Gly Glu
            20                  25                  30

Glu Gly Val Glu Glu Gly Lys Leu
        35                  40

<210> SEQ ID NO 104
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 104

Leu Glu Gln Tyr Glu Met His Gly Pro Glu Gly Leu Arg Val Gly Glu
1               5                   10                  15

Ser Glu Ser Glu Gly Gly Gly Gly Ser Leu Leu Gly Glu Phe Glu
            20                  25                  30

Val Glu Gly Gly Phe Ala Gly Leu Pro Asn Gly Lys Leu
        35                  40                  45

<210> SEQ ID NO 105
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Glu Gln Tyr Glu Met His Gly Pro Glu Gly Leu Arg Val Gly Gly
1               5                   10                  15

Phe Lys Glu Gly Val Glu Gly Glu Ile Glu Gly Gly Gly Phe Lys
            20                  25                  30

Glu Gly Val Glu Gly Lys Leu
        35

<210> SEQ ID NO 106
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Leu Glu Gln Tyr Glu Met His Gly Pro Glu Gly Leu Arg Val Gly Glu
1               5                   10                  15

Ser Glu Ser Glu Gly Gly Phe Ala Gly Leu Pro Asn Gly Lys Glu Glu
            20                  25                  30

Glu Gly Leu Gly Ser Ile Pro Glu Asn Phe Phe Gly Val Lys Leu
        35                  40                  45

<210> SEQ ID NO 107
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Leu Glu Gln Tyr Glu Met His Gly Pro Glu Gly Leu Arg Val Gly Ile
1               5                   10                  15

Pro Glu Asn Phe Phe Gly Val Thr Ser Glu Asp Leu Val Val Gln Glu
            20                  25                  30

Ala Ile Pro Met Ser Ile Pro Lys Leu
        35                  40

<210> SEQ ID NO 108
<211> LENGTH: 41
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 108

Leu Glu Gln Tyr Glu Met His Gly Pro Glu Gly Leu Arg Val Gly Glu
1               5                   10                  15

Ala Ile Pro Met Ser Ile Pro Thr Ser Glu Asp Leu Val Val Gln Ile
            20                  25                  30

Pro Glu Asn Phe Phe Gly Val Lys Leu
        35                  40

<210> SEQ ID NO 109
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Leu Glu Pro Ala Gly Ala Ala Arg Gly Glu Ser Glu Ser Glu Gly Gly
1               5                   10                  15

Phe Phe Gly Phe Pro Ile Gly Glu Arg Glu Ser Thr Gly Gly Asp Arg
            20                  25                  30

Gly Leu Pro Ile Gly Glu Asn Glu Ala Gly Gly Lys Leu
        35                  40                  45

<210> SEQ ID NO 110
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Leu Glu Thr Glu Gly Arg Gly Glu Arg Glu Ala Gln Gly Glu Phe Pro
1               5                   10                  15

Glu Val Glu Gly Glu Glu Gly Gly Gly Pro Glu Lys Glu Thr Gly
            20                  25                  30

Gly Glu Arg Glu Ala Gln Gly Lys Leu
        35                  40

<210> SEQ ID NO 111
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Leu Glu Ala Arg Gly Leu Glu Gly Gly Gly Gly Gly Ser Leu Leu Gly
1               5                   10                  15

Gly Tyr Pro Gly Ser Ser Arg Gly Gly Phe Lys Gly Val Glu Gly
            20                  25                  30

Gly Pro Ala Gly Ala Ala Arg Gly Lys Leu
        35                  40

<210> SEQ ID NO 112
<211> LENGTH: 41
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 112

Leu Glu Pro Gly Leu Ala Pro Gly Gly Glu Glu Gly Val Glu Glu Gly
1               5                   10                  15

Gly Pro Glu Glu Gly Val Glu Glu Gly Phe Lys Glu Gly Val Glu
            20                  25                  30

Gly Glu Pro Glu Ser Ser Gly Lys Leu
        35                  40

<210> SEQ ID NO 113
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Leu Glu Glu Gly Glu Ala Arg Gly Ser Thr Ala Gln Glu Ala Gly Glu
1               5                   10                  15

Gly Pro Lys Glu Glu Glu Gly Leu Gly Ser Ser Glu Leu Glu Gly Arg
            20                  25                  30

Gly Ser Pro Val Ser Gln Glu Leu Gly Gln Arg Lys Leu
        35                  40                  45

<210> SEQ ID NO 114
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Leu Glu Ala Gln Glu Ala Gly Glu Gly Lys Glu Glu Glu Gly Leu Gly
1               5                   10                  15

Ser Pro Val Ser Gln Glu Leu Gly Gln Arg Ser Glu Leu Glu Gly Arg
            20                  25                  30

Gly Ser Pro Thr Glu Gly Glu Ala Arg Gly Ser Lys Leu
        35                  40                  45

<210> SEQ ID NO 115
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Leu Glu Glu Glu Glu Gly Leu Gly Ser Lys Glu Glu Glu Gly Leu Gly
1               5                   10                  15

Ser Pro Lys Glu Glu Glu Gly Leu Gly Ser Lys Glu Glu Glu Gly Leu
            20                  25                  30

Gly Ser Pro Lys Glu Glu Glu Gly Leu Gly Ser Lys Leu
        35                  40                  45

<210> SEQ ID NO 116
<211> LENGTH: 49
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 116

Leu Glu Glu Leu Glu Gly Arg Gly Ser Lys Glu Glu Glu Gly Leu Gly
1               5                   10                  15

Ser Ile Pro Glu Asn Phe Phe Gly Val Phe Tyr Glu Ser Asp Val Met
                20                  25                  30

Gly Arg Gly His Ala Arg Leu Val His Val Glu Pro His Thr Lys
                35                  40                  45

Leu

<210> SEQ ID NO 117
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Leu Glu Glu Asn Phe Phe Gly Val Thr Glu Gly Glu Ala Arg Gly Ser
1               5                   10                  15

Pro Thr Ser Glu Asp Leu Val Val Gln Lys Glu Glu Gly Leu Gly
                20                  25                  30

Ser Glu Ala Ile Pro Met Ser Ile Pro Lys Leu
        35                  40

<210> SEQ ID NO 118
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Leu Glu Ile Pro Met Ser Ile Pro Lys Glu Glu Glu Gly Leu Gly Ser
1               5                   10                  15

Ile Pro Glu Asn Phe Phe Gly Val Thr Glu Gly Glu Ala Arg Gly Ser
                20                  25                  30

Pro Thr Ser Glu Asp Leu Val Val Gln Lys Leu
        35                  40

<210> SEQ ID NO 119
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Leu Glu Leu Gln Gln Tyr Glu Met His Gly Pro Glu Gly Leu Arg Val
1               5                   10                  15

Gly Glu Ala Ile Pro Met Ser Ile Pro Ile Pro Glu Asn Phe Phe Gly
                20                  25                  30

Val Lys Glu Glu Glu Gly Leu Gly Ser Lys Leu
        35                  40

<210> SEQ ID NO 120
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Leu Glu Glu Glu Gly Val Glu Gly Lys Glu Glu Glu Gly Leu Gly
1               5                   10                  15

Ser Gly Pro Ala Gly Ala Ala Arg Gly Ser Glu Leu Glu Gly Arg Gly
            20                  25                  30

Ser Pro Thr Glu Gly Glu Ala Arg Gly Ser Lys Leu
        35                  40

<210> SEQ ID NO 121
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Leu Glu Pro Glu Ser Ser Gly Glu Ala Ile Pro Met Ser Ile Pro Thr
1               5                   10                  15

Ser Glu Asp Leu Val Val Gln Ile Pro Glu Asn Phe Phe Gly Val Glu
            20                  25                  30

Ala Glu Gly Thr Gly Gly Glu Arg Gly Val Leu Gly Lys Leu
        35                  40                  45

<210> SEQ ID NO 122
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Leu Glu Gly Gly Gly Ser Leu Leu Gly Glu Pro Glu Pro Glu Gly Glu
1               5                   10                  15

Arg Glu Ala Gln Gly Gly Val Glu Gly Val Glu Leu Gly Gly Phe Lys
            20                  25                  30

Glu Gly Val Glu Gly Glu Gln Glu Gly Arg Gly Lys Leu
        35                  40                  45

<210> SEQ ID NO 123
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Leu Glu Ser Gln Glu Leu Gly Gln Arg Glu Ser Glu Ser Glu Gly Ser
1               5                   10                  15

Glu Leu Glu Gly Arg Gly Ser Gly Phe Lys Glu Gly Val Glu Gly Lys
            20                  25                  30

Glu Glu Glu Gly Leu Gly Ser Gly Phe Phe Gly Phe Pro Ile Gly Lys
        35                  40                  45

Leu
```

<210> SEQ ID NO 124
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Glu Gln Tyr Glu Met His Gly Pro Lys Glu Glu Glu Gly Leu Gly
1               5                   10                  15

Ser Ser Glu Leu Glu Gly Arg Gly Ser Glu Ala Ile Pro Met Ser Ile
            20                  25                  30

Pro Thr Ile Pro Glu Asn Phe Phe Gly Val Val Glu Glu Pro His Thr
        35                  40                  45

Lys Leu
    50

<210> SEQ ID NO 125
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Leu Glu Gln Tyr Glu Met His Gly Pro Ser Glu Leu Glu Gly Arg Gly
1               5                   10                  15

Ser Ile Pro Glu Asn Phe Phe Gly Val Glu Ala Ile Pro Met Ser Ile
            20                  25                  30

Pro Thr Ser Glu Asp Leu Val Val Gln Ile Val Glu Gly Pro His Thr
        35                  40                  45

Lys Leu
    50

<210> SEQ ID NO 126
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Asp Leu Val Val Gln
            20                  25                  30

Ile Ser Glu Leu Glu Gly Arg Gly Ser Val Glu Glu Pro His Thr Lys
        35                  40                  45

Leu

<210> SEQ ID NO 127
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Leu Glu Gln Tyr Glu Met His Gly Pro Ile Pro Glu Asn Phe Phe Gly
1               5                   10                  15

Val Ser Glu Leu Glu Gly Arg Gly Ser Glu Ala Ile Pro Met Ser Ile
            20                  25                  30

Pro Thr Glu Gly Glu Gly Glu Gly Glu Gly Val Glu Glu Pro His Thr
        35                  40                  45

Lys Leu
    50

<210> SEQ ID NO 128
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Glu Gln Tyr Glu Met His Gly Pro Ser Glu Leu Glu Gly Arg Gly
1               5                   10                  15

Ser Glu Ala Ile Pro Met Ser Ile Pro Thr Lys Glu Glu Gly Leu
            20                  25                  30

Gly Ser Ile Pro Glu Asn Phe Phe Gly Val Val Glu Glu Pro His Thr
        35                  40                  45

Lys Leu
    50

<210> SEQ ID NO 129
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Glu Gln Tyr Glu Met His Gly Pro Glu Ala Ile Pro Met Ser Ile
1               5                   10                  15

Pro Thr Glu Gly Glu Gly Glu Gly Glu Gly Ile Pro Glu Asn Phe Phe
            20                  25                  30

Gly Val Ser Glu Asp Leu Val Val Gln Ile Val Glu Glu Pro His Thr
        35                  40                  45

Lys Leu
    50

<210> SEQ ID NO 130
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Glu Ala Ile Pro Met Ser Ile Pro Thr Val Glu Glu Pro His Thr
        35                  40                  45
```

```
Lys Leu
    50

<210> SEQ ID NO 131
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Leu Glu Gln Tyr Glu Met His Gly Pro Glu Gly Glu Gly Glu Gly Glu
1               5                   10                  15

Gly Ile Ser Glu Asp Leu Val Val Gln Ile Pro Glu Asn Phe Phe Gly
            20                  25                  30

Val Lys Glu Glu Glu Gly Leu Gly Ser Val Glu Pro His Thr Lys
        35                  40                  45

Leu

<210> SEQ ID NO 132
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Leu Glu Gly Arg Gly
            20                  25                  30

Ser Ser Glu Asp Leu Val Val Gln Ile Val Glu Glu Pro His Thr Lys
        35                  40                  45

Leu

<210> SEQ ID NO 133
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Leu Glu Gln Tyr Glu Met His Gly Pro Ile Pro Glu Asn Phe Phe Gly
1               5                   10                  15

Val Glu Gly Glu Gly Glu Gly Glu Ser Glu Leu Glu Gly Arg Gly Ser
            20                  25                  30

Ser Glu Asp Leu Val Val Gln Ile Val Glu Glu Pro His Thr Lys Leu
        35                  40                  45

<210> SEQ ID NO 134
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Leu Glu Gln Tyr Glu Met His Gly Pro Ser Glu Leu Glu Gly Arg Gly
```

```
                1               5                   10                  15
Ser Ile Pro Glu Asn Phe Phe Gly Val Lys Glu Glu Glu Gly Leu Gly
                20                  25                  30

Ser Ser Glu Asp Leu Val Val Gln Ile Val Glu Glu Pro His Thr Lys
        35                  40                  45

Leu

<210> SEQ ID NO 135
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Leu Glu Gln Tyr Glu Met His Gly Pro Ile Pro Glu Asn Phe Phe Gly
1               5                   10                  15

Val Ser Glu Leu Glu Gly Arg Gly Ser Ser Glu Asp Leu Val Val Gln
                20                  25                  30

Ile Lys Glu Glu Glu Gly Leu Gly Ser Val Glu Glu Pro His Thr Lys
        35                  40                  45

Leu

<210> SEQ ID NO 136
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Leu Glu Gln Tyr Glu Met His Gly Pro Lys Glu Glu Glu Gly Leu Gly
1               5                   10                  15

Ser Ile Pro Glu Asn Phe Phe Gly Val Ser Glu Leu Glu Gly Arg Gly
                20                  25                  30

Ser Glu Gly Glu Gly Glu Gly Glu Gly Val Glu Glu Pro His Thr Lys
        35                  40                  45

Leu

<210> SEQ ID NO 137
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Leu Glu Gln Tyr Glu Met His Gly Pro Ser Glu Asp Leu Val Val Gln
1               5                   10                  15

Ile Lys Glu Glu Glu Gly Leu Gly Ser Ile Pro Glu Asn Phe Phe Gly
                20                  25                  30

Val Ser Glu Leu Glu Gly Arg Gly Ser Val Glu Glu Pro His Thr Lys
        35                  40                  45

Leu

<210> SEQ ID NO 138
<211> LENGTH: 49
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
                20                  25                  30

Val Lys Glu Glu Glu Gly Leu Gly Ser Val Glu Glu Pro His Thr Lys
        35                  40                  45

Leu

<210> SEQ ID NO 139
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
                20                  25                  30

Val Glu Ala Ile Pro Met Ser Ile Pro Thr Glu Pro His Thr Lys Leu
        35                  40                  45

<210> SEQ ID NO 140
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Glu Gln Tyr Glu Met His Gly Pro Glu Gly Glu Gly Glu Gly Glu
1               5                   10                  15

Gly Ile Pro Glu Asn Phe Phe Gly Val Glu Ala Ile Pro Met Ser Ile
                20                  25                  30

Pro Thr Ser Glu Leu Glu Gly Arg Gly Ser Glu Pro His Thr Lys Leu
        35                  40                  45

<210> SEQ ID NO 141
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Glu Gln Tyr Glu Met His Gly Pro Glu Ala Ile Pro Met Ser Ile
1               5                   10                  15

Pro Thr Ser Glu Leu Glu Gly Arg Gly Ser Ile Pro Glu Asn Phe Phe
                20                  25                  30

Gly Val Glu Gly Glu Gly Glu Gly Glu Gly Pro His Thr Lys Leu
        35                  40                  45

<210> SEQ ID NO 142
<211> LENGTH: 49
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

Leu Glu Gln Tyr Glu Met His Gly Pro Ser Glu Leu Glu Gly Arg Gly
1               5                   10                  15

Ser Ile Pro Glu Asn Phe Phe Gly Val Glu Gly Glu Gly Glu Gly Glu
            20                  25                  30

Gly Lys Glu Glu Glu Gly Leu Gly Ser Val Glu Glu Pro His Thr Lys
        35                  40                  45

Leu

<210> SEQ ID NO 143
<211> LENGTH: 48
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 143

Leu Glu Gln Tyr Glu Met His Gly Pro Ile Pro Glu Asn Phe Phe Gly
1               5                   10                  15

Val Ser Glu Asp Leu Val Val Gln Ile Glu Gly Glu Gly Glu Gly Glu
            20                  25                  30

Gly Glu Ala Ile Pro Met Ser Ile Pro Thr Glu Pro His Thr Lys Leu
        35                  40                  45

<210> SEQ ID NO 144
<211> LENGTH: 10
<212> TYPE: PRT
<213> ORGANISM: Unknown
<220> FEATURE:
<223> OTHER INFORMATION: Description of Unknown:
Aggrecan cleavage site sequence

<400> SEQUENCE: 144

Asn Ile Thr Glu Gly Glu Ala Arg Gly Ser
1               5                   10

<210> SEQ ID NO 145
<211> LENGTH: 11
<212> TYPE: PRT
<213> ORGANISM: Unknown
<220> FEATURE:
<223> OTHER INFORMATION: Description of Unknown:
Aggrecan cleavage site sequence

<400> SEQUENCE: 145

Thr Ala Ser Glu Leu Glu Gly Arg Gly Thr Ile
1               5                   10

<210> SEQ ID NO 146
<211> LENGTH: 11
<212> TYPE: PRT
<213> ORGANISM: Unknown
<220> FEATURE:
<223> OTHER INFORMATION: Description of Unknown:
Aggrecan cleavage site sequence

```
<400> SEQUENCE: 146

Thr Phe Lys Glu Glu Glu Gly Leu Gly Ser Val
1               5                   10

<210> SEQ ID NO 147
<211> LENGTH: 9
<212> TYPE: PRT
<213> ORGANISM: Unknown
<220> FEATURE:
<223> OTHER INFORMATION: Description of Unknown:
      Aggrecan cleavage site sequence

<400> SEQUENCE: 147

Val Asp Ile Pro Glu Asn Phe Phe Gly
1               5

<210> SEQ ID NO 148
<211> LENGTH: 5
<212> TYPE: PRT
<213> ORGANISM: Unknown
<220> FEATURE:
<223> OTHER INFORMATION: Description of Unknown:
      Aggrecan cleavage site sequence

<400> SEQUENCE: 148

Ala Arg Gly Ser Val
1               5

<210> SEQ ID NO 149
<211> LENGTH: 10
<212> TYPE: PRT
<213> ORGANISM: Unknown
<220> FEATURE:
<223> OTHER INFORMATION: Description of Unknown:
      Aggrecan cleavage site sequence

<400> SEQUENCE: 149

Ile Leu Thr Val Lys Pro Ile Phe Glu Val
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Tyr Lys Asp Asp Asp Lys Gly Ala Ser His His His His His
1               5                   10                  15

His

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 151

His His His His His His
1               5
```

```
<210> SEQ ID NO 152
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
                20                  25                  30

Gly His Ala Arg Leu Val His Val Glu Glu Pro His Thr Lys Leu
            35                  40                  45

<210> SEQ ID NO 153
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Leu Glu Gln Tyr Glu Met His Gly Pro Glu Gly Leu Arg Val Gly Glu
1               5                   10                  15

Ala Ile Pro Met Ser Ile Pro Thr Ser Glu Asp Leu Val Val Gln Ile
                20                  25                  30

Pro Glu Asn Phe Phe Gly Val Lys Leu
            35                  40

<210> SEQ ID NO 154
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Leu Glu Gly Tyr Glu Met His Gly Pro Glu Gly Leu Arg Val Gly Lys
1               5                   10                  15

Glu Glu Glu Gly Leu Gly Ser Ile Pro Glu Asn Phe Phe Gly Val Ser
                20                  25                  30

Glu Leu Glu Gly Arg Gly Ser Lys Leu
            35                  40

<210> SEQ ID NO 155
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Leu Glu Gly Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
                20                  25                  30

Gly His Ala Arg Leu Val His Val Glu Glu Pro His Thr Lys Leu
            35                  40                  45
```

THERAPEUTIC VARIANT ALPHA-2-MACROGLOBULIN COMPOSITIONS

CROSS-REFERENCE

This application is a divisional of U.S. application Ser. No. 15/528,387, filed on May 19, 2017, now issued as U.S. Pat. No. 10,400,028 on Sep. 3, 2019, which claims the benefit of International Application PCT/2015/061852, filed on Nov. 20, 2015, which claims the benefit of U.S. Provisional Application No. 62/082,304, filed on Nov. 20, 2014, which applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 11, 2015, is named 37151-706.401_SL.txt and is 113,105 bytes in size.

BACKGROUND OF THE INVENTION

Inflammation causing spinal and joint pain can be difficult to treat. Increasing degrees of inflammation and force applied to joints result in joint injury. Abnormal joint anatomy can be a hallmark of aging, but joint injury can be also a result of trauma, such as chondral lesions often seen in athletes. While joint injury resulting from trauma can be typically associated with acute inflammation, aberrant joint anatomy resulting from aging (e.g., osteoarthritis) can be a chronic condition. Physicians currently do not have a system or method available to differentiate between acute injury due to trauma and age related joint deteriorations.

Presently, it can be difficult to determine the appropriate course of treatment for a given patient since it can be frequently unclear whether the particular condition the patient suffers from may be acute or chronic or if pathology in the joint is the cause of the pain.

Spinal-related pain can be typically classified as discogenic, facetogenic or radiculopathic pain. The manifestation of radiculopathic pain has traditionally been attributed to various physical and/or mechanical abnormalities, such as compression or mechanical irritation of the nerve root related to conditions such as disc herniation, stenosis, spondylolisthesis, sciatica, piriformis syndrome, obturator syndrome, cystic lesions (e.g., ganglion and synovial), tumors, and other pathology, such as chemically mediated causes.

Numerous studies have attempted to elucidate the pathophysiology of spinal-related pain, and several molecular pathways have been implicated tentatively. However, no clear causal pathway leading from injury or degeneration to the painful state has been confirmed. Molecular markers can be linked to clinical symptoms, and serve as potential targets for the development of diagnostics and therapeutic tools. Although some studies have provided evidence that the epidural space can be affected by an intervertebral disc herniation, none has measured concentrations of biomolecules in the epidural space in an attempt to detect the differences between affected and non-affected persons.

Tendons, which connect muscle to bone, and ligaments, which connect bones to other bones, are both composed of bands of fibrous connective tissue. The cells of the fibrous connective tissue are mostly made up of fibroblasts the irregular, branching cells that secrete strong fibrous proteins (such as collagens, reticular and elastic fibers, and glycoproteins) as an extracellular matrix. The extracellular matrix can be defined in part as any material part of a tissue that is not part of any cell. So defined, the extracellular matrix (ECM) can be the significant feature of the fibrous connective tissue.

The ECM's main component can be various glycoproteins. In most animals, the most abundant glycoprotein in the ECM can be collagen. Collagen can be tough and flexible and gives strength to the connective tissue. Indeed, the main element of the fibrous connective tissue is collagen (or collagenous) fiber. The ECM also contains many other components: proteins such as fibrin and elastin, minerals such as hydroxyapatite, or fluids such as blood plasma or serum with secreted free flowing antigens. Given this diversity, it can serve any number of functions, such as providing support and anchorage for cells (which attach via focal adhesions), providing a way of separating the tissues, and regulating intercellular communication. Therefore, the ECM can function in a cell's dynamic behavior.

Injury to tendons and ligaments causes damage not only to the connective tissue, but to the extracellular matrix as well. Damage to the ECM can interrupt cell behavior in the connective tissue and decrease and/or limit healing. After injury, continuing damage can be caused by production of matrix metalloproteinases (MMPs) by the body. MMPs are enzymes that degrade all components of the ECM. This can lead to an imbalance between the synthesis and degradation of the ECM, as the body tries to heal itself while the enzymes remodel the ECM. An overabundance of remodeling by MMPs cause damage to previously connected tissue which results in the formation of scar tissue. In addition, scar tissue adhesion to surrounding tissue can cause further pulling and/or stretching of the tendons or ligaments and resultant pain.

Currently, treatment of injury to tendons and ligaments includes some simple measures such as: avoiding activities that aggravate the problem; resting the injured area; icing the area the day of the injury; and taking over-the-counter anti-inflammatory medicines. However, these simple remedies do not always cure the injury and often more advanced treatments are needed. These treatments include: corticosteroid injections, platelet-rich plasma (PRP), hyaluronic acid (HA) injection, physical therapy and even surgery. Corticosteroids are often used because they can work quickly to decrease the inflammation and pain. Physical therapy can include range of motion exercises and splinting (such as for the fingers, hands, and forearm). Surgery can be only rarely needed for severe problems not responding to the other treatments. It can be appreciated that additional treatment measures are needed to treat and prevent extracellular matrix degradation for quicker and improved healing of tendons and ligaments.

Alpha-2-macroglobulin (A2M) is a highly conserved protease inhibitor present in plasma at relatively high concentrations (0.1-6 mg/ml). It is unique in its ability to inhibit all the major classes of proteases (Bhattacharjee et al (2000) J. Biol. Chem. 275, 26806-26811). A2M can be produced by several cell types, such as hepatocytes, lung fibroblasts, macrophages, astrocytes and tumor cells (Borth W, "Alpha 2-macroglobulin, A multifunctional binding and targeting protein with possible roles in immunity and autoimmunity," Ann. N.Y. Acad. Sci. 737:267-272 (1994)). A2M often exists as a tetramer of four identical 180 kDa subunits that forms a hollow cylinder-like structure. It can present multiple target peptide bonds to attacking proteases in its central "bait" domain. A2M can be the major protease inhibitor acting on foreign proteases, such as snake venoms. However, there are many other protease inhibitors in the circulation and it has been proposed that A2M can have other functions including binding to and regulation of cytokine and growth factor activity, promotion of tumoricidal capabilities of macrophages, and enhancement of antigen presentation. A2M can also be a targeting carrier for cytokines or growth factors.

SUMMARY OF THE INVENTION

Therefore, it is an object of the invention to provide compositions, systems, methods, and kits for the detection, diagnosis, and treatment of inflammation, pain in the spine or joint, degradation of extracellular matrix, and inhibiting fibronectin aggrecan complex (FAC) (FIG. 1). It is another object of the invention to provide biomarkers and methods for identifying sites in the spine or joint for treating pain. It is another object of the invention to provide biomarkers that can be used to diagnose or assist in the diagnosis be of the presence of pathologies that are causative of spinal- or joint-related pain. It is another object of the invention to provide methods for diagnosing or assisting in the diagnosis of the presence of pathologies that are causative of spinal- or joint related pain. Yet another object of the invention is to provide biomarkers and methods to determine an appropriate therapy for a subject experiencing spinal- or joint-related pain. Another object of the invention is to provide biomarkers and methods to monitor and assess the efficacy of a treatment for spinal- or joint-related pain. Another object of the invention is to provide compositions and methods for treating spinal or joint pain and for selecting treatment sites in the spine or joint for treatment to inhibit or reduce pain.

Another object of the invention is to provide compositions, systems, methods, and kits for the detection, diagnosis, and treatment of inflammation, degradation of extracellular matrix, and wounds. It is another object of the invention to provide systems and methods to produce compositions for the treatment of inflammation, degradation of extracellular matrix, and chronic wounds. It is another object of the invention to provide biomarkers and methods for identifying sites of chronic wounds. It is another object of the invention to provide methods for diagnosing or assisting in the diagnosis of the presence of pathologies that are causative of chronic wounds. Yet another object of the invention is to provide biomarkers and methods to determine an appropriate therapy for a subject experiencing chronic wounds. Another object of the invention is to provide biomarkers and methods to monitor and assess the efficacy of a treatment for chronic wounds. Another object of the invention is to provide compositions and methods for treating chronic wounds and for selecting treatment sites and methods for treatment of chronic wounds.

Another object of the invention provides variant polypeptides for treating chronic wounds. It is another object of the invention to provide variant A2M polypeptides with a higher protease inhibitory activity than a wild-type A2M polypeptide. It is another object of the invention to provide methods of making variant polypeptides for the treatment of chronic wounds.

Another object of the invention provides variant polypeptides for treating inflammation and pain. It is another object of the invention to provide variant A2M polypeptides that inhibit the formation of fibronectin aggrecan complex (FAC). Another object of the invention provides variant A2M polypeptides with a higher protease inhibitory activity than a wild-type A2M polypeptide. It is another object of the invention to provide methods of making variant polypeptides for the treatment of inflammation and pain.

In some aspects, compositions are provided that comprise a variant A2M polypeptide, comprising a bait region, wherein the bait region of the variant A2M polypeptide comprises a plurality of protease recognition sites arranged in series. In some embodiments, the variant A2M polypeptide is a recombinant protein. In some embodiments, the variant A2M polypeptide is produced in a host comprising bacteria, yeast, fungi, insect, or mammalian cells, or a cell free system. In some embodiments, the variant A2M polypeptide is characterized by an enhanced nonspecific inhibition of serine proteases, threonine proteases, cysteine proteases, aspartate proteases, metalloproteases, glutamic acid proteases, or any combination thereof. In some embodiments, the variant A2M polypeptide further comprises PEG with abnormal glycosylation sites. In some embodiments, the variant A2M polypeptide has a longer half-life than the half-life of a wild type A2M protein when disposed within a joint or spine disc of a subject. In some embodiments, the plurality of protease recognition sites comprise one or more protease substrate bait regions from one or more proteins other than A2M, one or more additional protease bait regions from A2M, one or more non-natural protein sequences, or any combination thereof, wherein the modified A2M protein is characterized by at least a 5%, 10%, 15%, 20%, 25%, or 30% increase in protease inhibitory effectiveness compared to the protease inhibitory effectiveness of a wild type A2M protein. In some embodiments, the non-natural protein sequences comprise one or more protease recognition sites that can function as bait for proteases. In some embodiments, the one or more protease substrate bait regions comprise consensus sequences for serine proteases, threonine proteases, cysteine proteases, aspartate proteases, metalloproteinases, glutamic acid proteases, or any combination thereof. In some embodiments, the protease substrate bait regions comprise one or more consensus sequences for one or more proteases from one or more organisms. In some embodiments, the one or more organisms comprise animals, plants, bacteria, yeast, fish, reptiles, amphibians, or fungi. In some embodiments, one or more of the one or more protease substrate bait regions from the one or more proteins other than A2M are the same. In some embodiments, one or more of the one or more protease substrate bait regions from A2M are the same. In some embodiments, one or more of the one or more protease substrate bait regions from the one or more non-natural protein sequences are the same. In some embodiments, one or more of the one or more protease substrate bait regions from the one or more proteins other than A2M or from the one or more non-natural protein sequences comprise a suicide inhibitor; wherein the suicide inhibitor is operable to covalently attach a protease to A2M. In some embodiments, one or more of the one or more protease substrate bait regions are from different species.

In some aspects, provided herein is a composition comprising an isolated variant A2M polypeptide, wherein the variant A2M polypeptide comprises one or more non-natural bait regions, wherein the one or more non-natural bait regions comprise one or more protease recognition sites not present in a wild-type A2M polypeptide. In some embodiments, the modified A2M polypeptide is characterized by at least a 5%, 10%, 15%, 20%, 25%, or 30% enhanced inhibition of one or more proteases compared to a wild-type A2M inhibition of the one or more proteases. In some embodiments, the enhanced inhibition comprises enhanced nonspecific inhibition. In some embodiments, the enhanced inhibition comprises enhanced specific inhibition. In some embodiments, the protease comprises a serine protease, threonine protease, cysteine protease, aspartate protease, metalloprotease, glutamic acid protease, or any combination thereof. In some embodiments, the protease comprises MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11 (Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xco14, Xenopus collagenase), MMP19 (RASI-1, stromelysin-4), MMP20 (Enamelysin), MMP21 (X-MMP), MMP23A (CA-MMP), MMP23B, MMP24 (MT5-MMP), MMP25 (MT6-MMP), MMP26 (Matrilysin-2, endometase), MMP27 (MMP-22, C-MMP), MMP28 (Epilysin); A Disintegrin and Metalloproteinase with Thrombospondin Motifs protease (ADAMTS), such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMPSTE2; ZMPSTE4; ZMPSTE24; acetylcholinesterase; or a combination thereof. In some embodiments, the protease comprises ADAMTS4, ADAMTS 5, MMP13, or a combination thereof. In some embodiments, the modified A2M polypeptide is characterized by at least a 10% enhanced inhibition of FAC formation compared to a wild-type A2M inhibition of FAC formation. In some embodiments, the one or more non-natural bait regions are derived from one or more proteins other than A2M. In some embodiments, the one or more proteins other than A2M are from a non-human organism. In some embodiments, the non-human organism comprises an animal, plant, bacterium, yeast, fish, reptile, amphibian, or fungi. In some embodiments, the one or more non-natural bait regions comprise one or more sequences of SEQ ID NOs 6-83, or fragments thereof. In some embodiments, the variant A2M polypeptide comprises SEQ ID NO 4, or a fragment thereof. In some embodiments, the one or more non-natural bait regions comprise SEQ ID NOs 6-30. In some embodiments, the one or more protease recognition sequences comprise SEQ ID NOs 31-83, or fragments thereof. In some embodiments, the wild-type A2M polypeptide comprises SEQ ID NO 3, or a fragment thereof. The wild-type A2M bait region consists of SEQ ID NO 5. In some embodiments, one or more of the one or more non-natural bait regions comprise a suicide inhibitor; wherein the suicide inhibitor is operable to covalently attach a protease to the variant A2M polypeptide. In some embodiments, the one or more protease recognition sites comprise 2 or more copies of the one or more protease recognition sequences. In some embodiments, the one or more non-natural bait regions comprise 2 or more copies of the one or more non-natural bait regions. In some embodiments, the variant A2M polypeptide comprises a wild-type A2M bait region sequence. In some embodiments, the variant A2M polypeptide is a recombinant polypeptide. In some embodiments, the one or more protease recognition sites comprise a consensus sequence for a protease. In some embodiments, the variant A2M polypeptide comprises one or more modified glycosylation sites. In some embodiments, the one or more modified glycosylation sites are functionalized with PEG. In some embodiments, the variant A2M polypeptide has at least a 10% longer half-life than the half-life of a wild type A2M polypeptide when disposed within a subject.

In some aspects, provided herein is a method of treating a subject with one or more conditions, comprising administering to the subject an effective amount of any composition provided herein comprising an A2M variant. In some embodiments, nonspecific inhibition of one or more proteases in the subject, inhibition Aggrecan G3 fragment formation, inhibition FAC formation, or a combination thereof, is increased. In some embodiments, the rate of degeneration of tissue, cartilage and discs, synovial inflammation, or a combination thereof, is decreased in the subject. In some embodiments, treating results in a reduction in severity, occurrence, rate of progression, or a combination thereof, of the one or more conditions. In some embodiments, any of the methods provided herein further comprise administering one or more additional carriers or drugs. In some embodiments, the one or more additional carriers or drugs comprise hydrogels, hyaluronic acid preparations, polymer microspheres, corticosteroids, microparticles, chitosan, local anesthetics, growth factors, cytokines, protease inhibitors, steroids, hyaluronic Acid (HA), or other biologically active autogenous or endogenous mediators. In some embodiments, the one or more conditions are treatable with any composition provided herein. In some embodiments, the one or more conditions comprise cancer, degenerative diseases, traumatic diseases, and/or inflammatory diseases, whose pathogenesis includes the activity of proteases. In some embodiments, the cancer, degenerative diseases, traumatic diseases, and/or inflammatory diseases whose pathogenesis includes the activity of proteases comprises osteoarthritis, inflammatory arthritides, chondrosis, chondral injuries, enthesopathies, tendinopathies, ligamentous injuries, degenerative diseases of the bone, cartilage, tendons, and ligaments, post-operative conditions and wound healing, and other musculoskeletal diseases. In some embodiments, the one or more conditions comprise cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof. In some embodiments, inflammation comprises joint or disc inflammation caused by surgery, joint or disc inflammation caused by a joint or disc replacement, or a combination thereof. In some embodiments, the subject is a human, pig, mouse, rat, rabbit, cat, dog, monkey, frog, horse or goat. In some embodiments, the subject has been previously diagnosed with the one or more conditions. In some embodiments, the composition is administered into an anatomic site relevant to the host pathology. In some embodiments, the administration comprises injection with a hollow-lumen device or flexible catheter combinations. In some embodiments, the hollow-lumen device comprises a needle, syringe, or combination thereof. In some embodiments, the administration occurs during a surgical procedure.

In some aspects, provided herein is a composition comprising an isolated variant A2M polynucleotide, wherein the variant A2M polynucleotide encodes for one or more non-natural bait regions, wherein the one or more non-natural bait regions comprise one or more protease recognition sites not present in a wild-type A2M polypeptide. In some embodiments, the non-natural bait regions comprise a sequence with at least 60%, 70%, 80%, 90%, 95%, 97%, 98%, 99%, 99.5%, or 99.9% identity to any one of SEQ ID NOs 6-83, or fragments thereof. In some embodiments, the non-natural bait regions comprise one or more protease recognition sequences with at least 60%, 70%, 80%, 90%, 95%, 97%, 98%, 99%, 99.5%, or 99.9% identity to any one of SEQ ID NOs 31-83. In some embodiments, the variant A2M polynucleotide comprises at least 90% identity to SEQ ID NO 2, or a fragment thereof. In some embodiments, the wild-type A2M polynucleotide comprises SEQ ID NO 1, or a fragment thereof. In some embodiments, the variant A2M polynucleotide is within an expression vector.

In one aspect, provided herein is a method for determining the enhanced inhibition of a protease by a variant A2M polypeptide comprising: (a) providing a variant A2M polypeptide comprising a sequence of one or more of SEQ ID NOs 6-83; (b) contacting the variant A2M polypeptide with the protease and a substrate cleaved by the protease; (c) contacting a wild-type A2M polypeptide with the protease and the substrate cleaved by the protease; and (d) comparing the amount of cleavage of the substrate from step (b) to the amount of cleavage of the substrate from step (c), thereby determining the enhanced inhibition of the protease by the variant A2M polypeptide.

In some aspects, provided herein is a method for making a variant A2M polynucleotide comprising: (a) providing a vector containing a variant A2M polynucleotide comprising a sequence of SEQ ID NO 2; (b) digesting the vector containing a variant A2M polynucleotide with restriction endonucleases to form a linear vector; (c) ligating one end of the one or more polynucleotides encoding one or more of the non-natural bait regions of SEQ ID NOs 6-83 to one end of the linear vector; and (d) ligating the other end of the one or more polynucleotides encoding one or more of the non-natural bait regions of SEQ ID NOs 6-83 to the other end of the linear vector, thereby forming a vector containing a variant A2M polynucleotide comprising the non-natural bait regions of SEQ ID NOs 6-83.

In some aspects, provided herein is a method for making a variant A2M polynucleotide comprising: (a) providing a vector containing a variant A2M polynucleotide comprising a sequence of SEQ ID NO 2; (b) digesting the vector containing a variant A2M polynucleotide with restriction endonucleases to form a linear vector; (c) ligating one end of the one or more polynucleotides encoding one or more of the non-natural bait regions of SEQ ID NOs 6-30 or one or more protease recognition sites of SEQ ID NOs 31-83 to one end of the linear vector; and (d) ligating the other end of the one or more polynucleotides encoding one or more of the non-natural bait regions of SEQ ID NOs 6-30 or one or more protease recognition sites of SEQ ID NOs 31-83 to the other end of the linear vector, thereby forming a vector containing a variant A2M polynucleotide comprising the non-natural bait regions of SEQ ID NOs 6-30 or one or more protease recognition sites of SEQ ID NOs 31-83.

In some aspects, a composition is provided that comprises a variant A2M polypeptide or polynucleotide, wherein the composition is obtainable by any method provided herein.

In one aspect, provided herein is a composition comprising A2M for use in therapy wherein the composition is a composition obtainable by any method provided herein, or any variant A2M composition provided herein In some embodiments, the composition is for use in the treatment of cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof; wherein inflammation comprises joint or disc inflammation caused by surgery, joint or disc inflammation caused by a joint or disc replacement, or a combination thereof.

In one aspect, provided herein is a use of a composition obtainable by any method provided herein, or any variant A2M composition provided herein, for the manufacture of a medicament for use in therapy. In some embodiments, the medicament is for use in the treatment of cancer, arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof; wherein inflammation comprises joint or disc inflammation caused by surgery, joint or disc inflammation caused by a joint or disc replacement, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the event of a conflict between a term herein and a term incorporated by reference, the term herein controls.

BRIEF DESCRIPTION OF THE DRAWINGS

The novel features are set forth with particularity in the appended claims. A better understanding of the features and advantages will be obtained by reference to the following detailed description that sets forth illustrative embodiments, in which the principles of devices, methods, and compositions are utilized, and the accompanying drawings of which:

FIG. 8A depicts a graph demonstrating the sulfated glycosaminoglycan (sGAG) released upon cartilage catabolism in a BCE model with and without treatment of MMP-7 and MMP-12. Treatment with purified A2M inhibited the MMP-induced cartilage catabolism.

FIG. 8B depicts a stained SDS-PAGE gel of samples produced in FIG. 9A. The MMP-7- or MMP-12-induced degradation of cartilage, and the production of cartilage protein fragments visible in the gel, was inhibited with addition of purified A2M.

FIG. 8C depicts a Western Blot with α-Aggrecan G3 antibody using the gel from FIG. 8B and the samples from FIG. 8A. The degradation of cartilage by MMP-7 or MMP-12 produces an Aggrecan G3 fragment at ~30 kDa which can be inhibited with addition of purified A2M.

FIG. 9A, FIG. 9B, FIG. 9C, FIG. 9D, FIG. 9E, and FIG. 9F are exemplary graphs depicting the results of an ELISA test that recognizes complexes of Fibronectin and Aggrecan G3 (FACT, Fibronectin Aggrecan Complex Test). Culture media from BCE treated with or without the listed proteases in the presence or absence of A2M were incubated with Synovial Fluid (SF) spiked with free Fibronectin and tested on the FACT assay. In each case where degradation of cartilage led to Aggrecan fragments the result was formation of additional Fibronectin Aggrecan Complexes above the SF background control. Treatment with A2M, however, which prevented cartilage catabolism, subsequently preventing FAC formation.

FIG. 10A and FIG. 10B are exemplary graphs depicting two bar graphs demonstrating the ability of APIC (Retentate from the 500 kDa filter) and the Filtrate to prevent cartilage degradation. Cartilage catabolism was induced in the BCE model with ADAMTS-5, which could be inhibited with serial dilution of APIC (left, Retentate), but not the Filtrate which is devoid of A2M (right, Filtrate). The numbers above the columns represent the percentage of APIC (v/v) or filtrate in the culture media. The inhibitory potential in 5% of Filtrate is equivalent to 0.01% of APIC; thus the process of producing APIC concentrates >99% of the chondroprotective effects of blood.

FIG. 14A, FIG. 14B, FIG. 14C, and FIG. 14D are exemplary graphs of histopathology evaluation of the rabbit knees from experiments depicted in FIGS. 12 and 13 including structure, chondrocyte density, Safarin-O staining, and cluster formation evaluations; and shows an inverse correlation between A2M concentration in each rabbit's APIC and the scoring criteria. One outlying rabbit is excluded from calculations in the line but is included in the figures.

are prepared with a 1:1 molar ratio of A2M:protease. Those with the "–D" are prepared at a 0.5:1 ratio of A2M:protease.

Figure 18B:
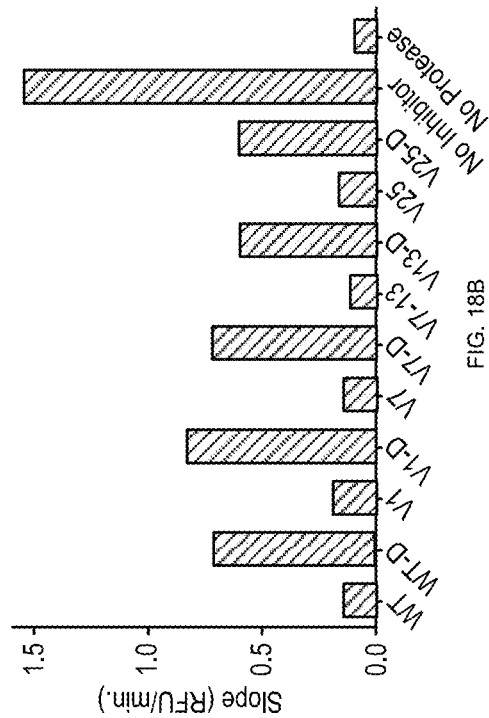
FIG. 18A depicts the raw data and FIG. 18B depicts the calculated slope of digestion of FTC-casein by bovine trypsin in the presence of tagged wild-type A2M (WT) or the four chosen A2M variants. The samples without the "–D"
Figure 18D:
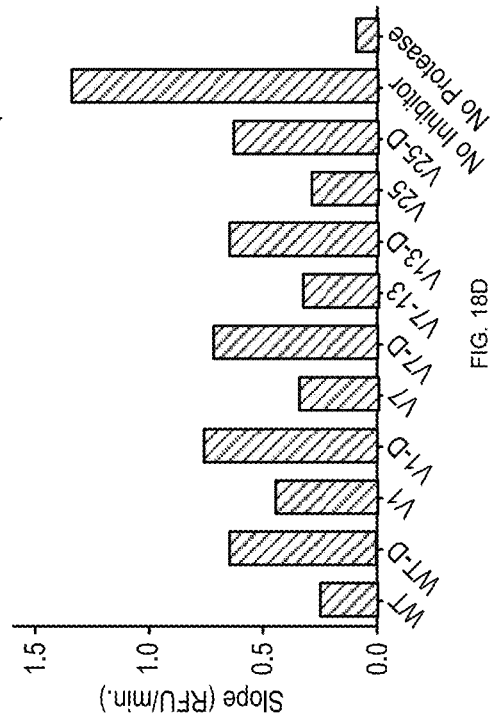
Figure 18A:
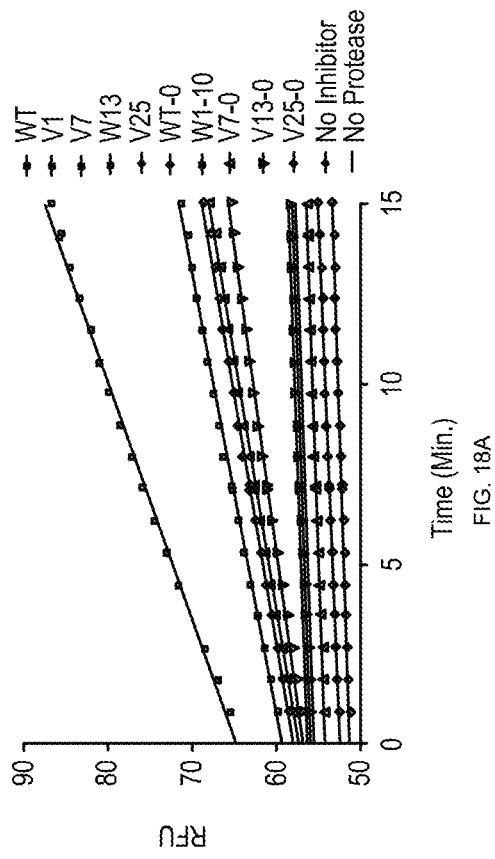
Figure 18C:
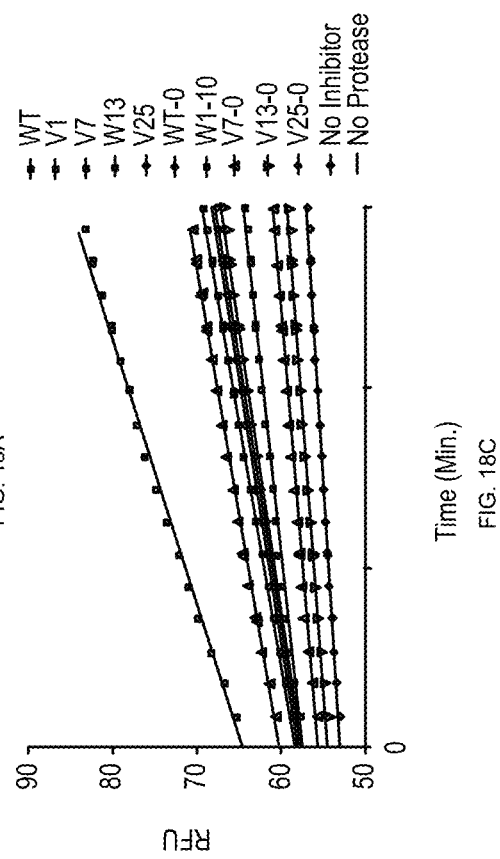

FIG. 18C depicts the raw data and FIG. 18D depicts the calculated slope of digestion of FTC-casein by chymotrypsin in the presence of tagged wild-type A2M (WT) or the four chosen A2M variants. The samples without the "–D" are prepared with a 1:1 molar ratio of A2M:protease. Those with the "–D" are prepared at a 0.5:1 ratio of A2M:protease.

Figure 19:
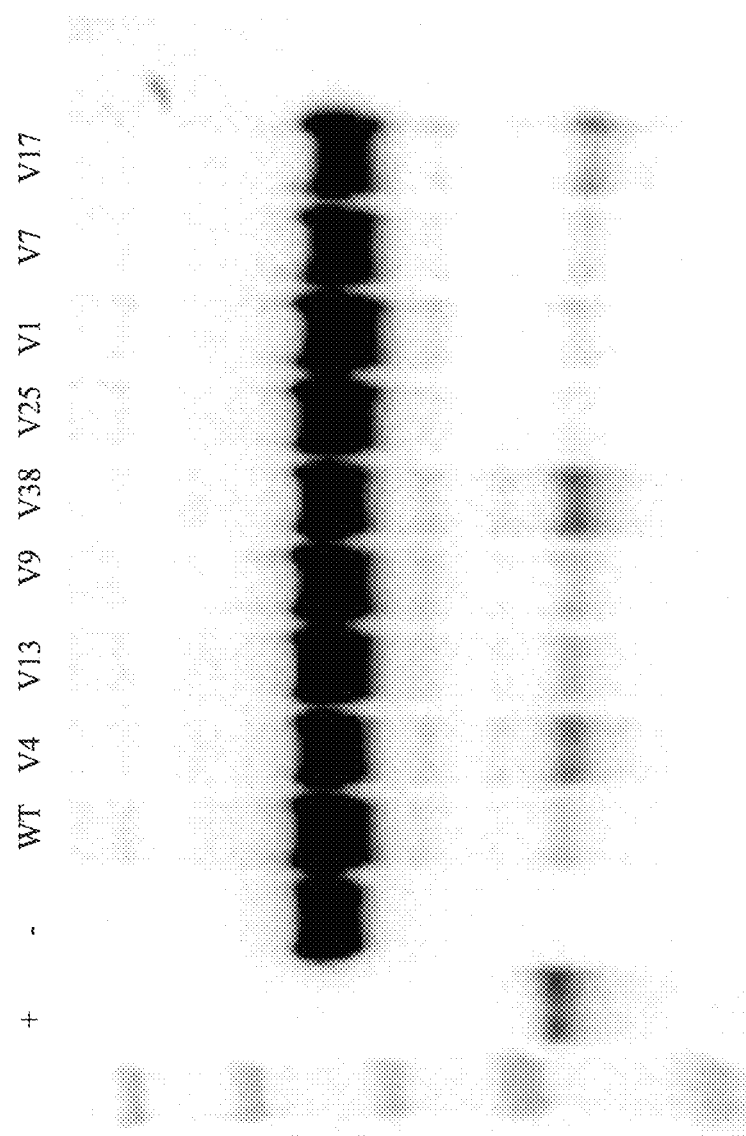

FIG. 19 depicts a western blot analysis of a cleavage assay using IGD fragment as a substrate in the presence of the MMP3.

FIG. 20 depicts a chart of the inhibition of IGD fragment proteolysis by the indicated variants as a percentage of wild-type A2M (top) and the sequences of the bait sequences corresponding to the indicated A2M variants (bottom).

Figure 21:
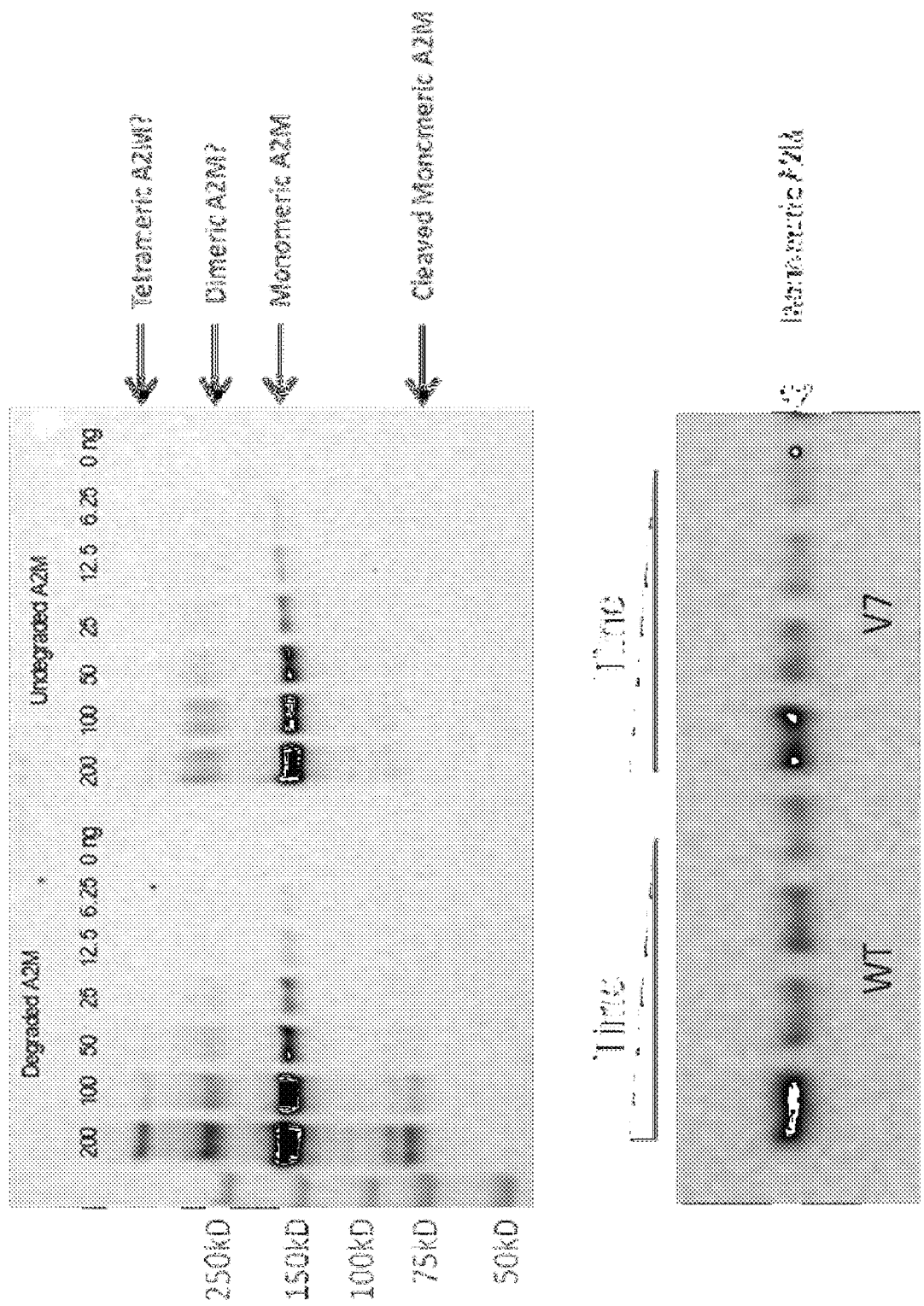

FIG. 21 depicts Western blots showing the control blot of degraded and non-degraded forms of A2M as a function of the known amount of protein indicated (top) and the cleavage of various A2M polypeptides over time in the presence of a protease (bottom). The control blot can be used to quantify the amount of cleaved A2M, which is directly proportional to the rate of protease inhibition.

Figure 22:
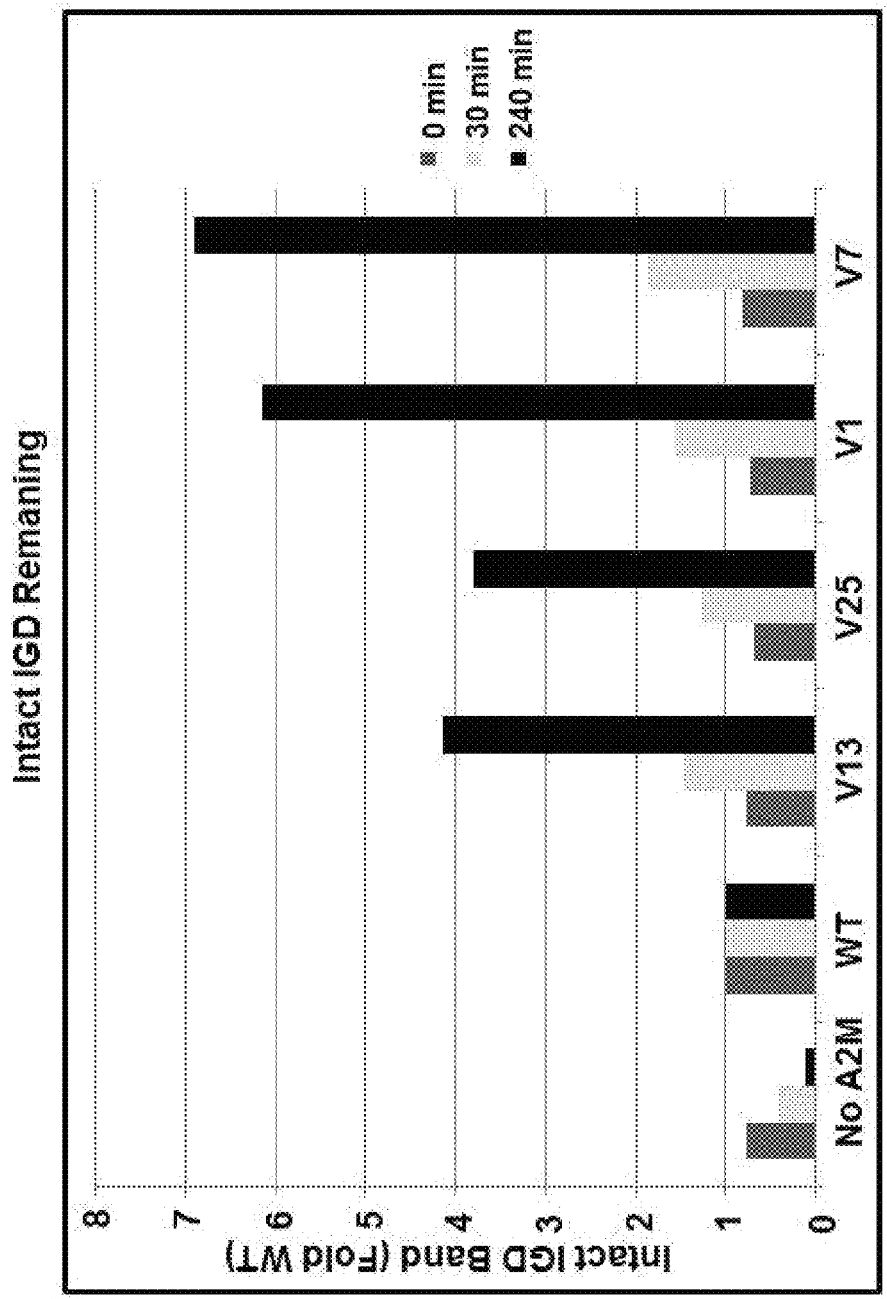

FIG. 22 depicts the protective effect of the A2M wild type vs. some of the variants of the digestion of IGD domain from a mixture of proteases. 10 nM of each MMP1, MMP3, MMP7, MMP13, ADAMTS4 and ADAMTS5 were mixed and used to digest IGD in the presence or absence of A2M wild type and A2M variants.

Figure 23:
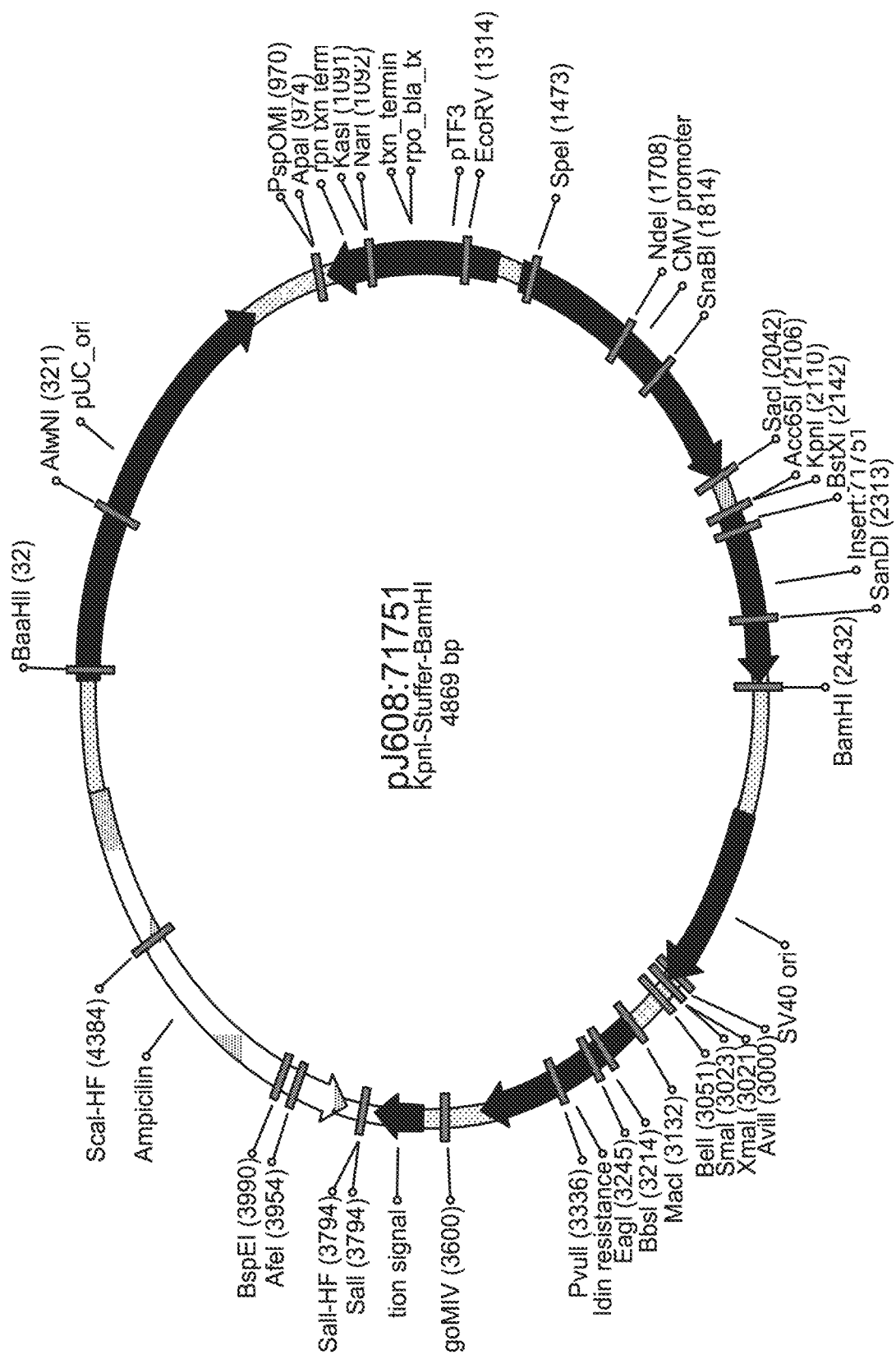

FIG. 23 depicts a Vector Map of pJ608 mammalian expression vector. The ORF sequence coding for wild-type and variant A2M is cloned in between the Kpn1 and BamH1 restriction sites.

DETAILED DESCRIPTION OF THE DISCLOSURE

Provided herein are compositions, methods, kits and systems for the detection, diagnosis, and treatment of inflammation, pain in the spine or joint, and degradation of extracellular matrix.

The details of one or more inventive embodiments are set forth in the accompanying drawings, the claims, and in the description herein. Other features, objects, and advantages of inventive embodiments disclosed and contemplated herein will be apparent from the description and drawings, and from the claims. As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment. As used herein, unless otherwise indicated, some inventive embodiments herein contemplate numerical ranges. When ranges are present, the ranges include the range endpoints. Additionally, every subrange and value within the range is present as if explicitly written out.

Definitions

The term "non-immunogenic" or "non-antigenic" means that the composition being administered to a subject does not elicit an immune response.

A "subject" refers to a donor, recipient or host of the composition of the present invention. In some embodiments, the donor and the recipient are the same. In some embodiments the subject is a human subject.

A "proteoglycan" refers to a special class of proteins that are heavily glycosylated. A proteoglycan is made up of a core protein with numerous covalently attached high sulphated glycosaminoglycan chain(s). Non-limiting example of extracellular matrix proteoglycans include aggrecan and certain collagens, such as collagen IX.

A "glycosaminoglycan" or "GAG" as used herein refers to a long unbranched polysaccharide molecules found on the cell surface or within the extracellular matrix. Non-limiting examples of glycosaminoglycan include heparin, chondroitin sulfate, dextran sulfate, dermatan sulfate, heparin sulfate, keratin sulfate, hyaluronic acid, hexuronyl hexosaminoglycan sulfate, and inositol hexasulfate.

The term "non-autologous" refers to tissue or cells which originate from a donor other than the recipient. Non-autologous can refer to, for example, allogeneic or xenogeneic. The term "autologous" as in an autologous composition, refers to a composition in which the donor and recipient is the same individual. Likewise, "allogeneic" refers to a donor and a recipient of the same species; "syngeneic" refers to a donor and recipient with identical genetic make-up (e.g. identical twins or autogeneic) and "xenogeneic" refers to donor and recipient of different species.

"Variant" (or "analog") refers to a molecule differing from the wild-type molecule.

The term "variant polynucleotide" (or "analog") refers to any polynucleotide differing from the naturally occurring polynucleotide. For example, "variant A2M polynucleotide" refers to any A2M polynucleotide differing from naturally occurring A2M polynucleotides. A variant A2M polynucleotide includes a polynucleotide sequence different from the wild-type A2M polynucleotide sequence (SEQ ID NO: 1). Variant polynucleotides can be characterized by nucleic acid insertions, deletions, and substitutions, created using, for example, recombinant DNA techniques. A variant A2M polynucleotide preferably includes a mutation, insertion, deletion, or a combination thereof, in the bait region of a wild-type A2M polynucleotide sequence. As used herein, when referring to polypeptides, the "bait region" includes the region of an A2M polynucleotide that encodes the region of the A2M polypeptide that binds to proteases, for example, regions that contain protease recognition sites. A variant A2M polynucleotide includes an "A2M acceptor sequence" (SEQ ID NO: 2) which includes a polynucleotide sequence of A2M with point mutations that can aid in creating variant A2M polynucleotides by recombinant DNA techniques, for example, by creating restriction enzyme cloning sites to aid in inserting various polynucleotide sequences encoding the variant bait regions. Variant bait regions can include one or more sequences of SEQ ID NOs: 6-83 and sequences substantially similar to SEQ ID NOs: 6-83. For example, variant bait regions can include one or more nonnatural bait regions of SEQ ID NOs 6-30, one or more protease recognition sites of SEQ ID NOs 31-83, or any combination thereof.

The term "variant polypeptide" refers to any polypeptide differing from the naturally occurring polypeptide. For example, "variant A2M polypeptide" refers to any A2M polypeptide differing from naturally occurring A2M polypeptides. Variant polypeptides can be characterized by amino acid insertions, deletions, and substitutions, created using, for example, recombinant DNA techniques. A variant A2M polypeptide includes a polypeptide sequence different from the wild-type A2M polypeptide sequence. A variant A2M polypeptide preferably includes a mutation, insertion, deletion, or a combination thereof, in the bait region of a wild-type A2M protein. When referring to polypeptides, the "bait region" includes the region of an A2M polypeptide that binds to proteases, for example, a stretch of amino acids that contains one or more protease recognition sites. A variant A2M polypeptide includes a polypeptide (SEQ ID NO: 3) encoded by an A2M acceptor sequence (SEQ ID NO: 2). A "variant A2M polypeptide" can have at least one amino acid sequence alteration in the bait region as compared to the amino acid sequence of the corresponding wild-type polypeptide. An amino acid sequence alteration can be a substitution, a deletion, or an insertion of one or more amino acids. A variant A2M polypeptide can have any combination of amino acid substitutions, deletions or insertions.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence. Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as inhibition of proteases, ligand-binding affinities, interchain affinities, or degradation/turnover rate. Variant nucleotides can also be used to generate polypeptides that are better suited for expression, scale up and the like in the host cells chosen for expression. For example, cysteine residues can be deleted or substituted with another amino acid residue in order to eliminate disulfide bridges.

An amino acid "substitution" includes replacing one amino acid with another amino acid having similar structural and/or chemical properties, for example, conservative amino acid replacements. "Conservative" amino acid substitutions can be made on the basis of similarity in polarity, charge, solubility, hydrophobicity, hydrophilicity, the amphipathic nature of the residues involved, or a combination thereof. Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine. Positively charged (basic) amino acids include arginine, lysine, and histidine. Negatively charged (acidic) amino acids include aspartic acid and glutamic acid. "Insertions" or "deletions" are preferably in the range of about 1 to 50 amino acids, more preferably 1 to 30 amino acids. The variation allowed can be experimentally determined by inserting, deleting, or substituting amino acids in a polypeptide using recombinant DNA techniques and assaying the resulting recombinant variants for activity, for example, protease inhibition activity.

The terms "purified" or "substantially purified" as used herein denotes that the indicated nucleic acid or polypeptide is present in the substantial absence of other biological macromolecules, for example, polynucleotides, proteins, and the like. The polynucleotide or polypeptide can be purified such that it constitutes at least 95% by weight, for example, at least 99% by weight, of the indicated biological macromolecules present. Water, buffers, and other small molecules with a molecular weight of less than 1000 Daltons, can be present in any amount. The term "isolated" as used herein refers to a polynucleotide or polypeptide separated from at least one other component present with the polynucleotide or polypeptide in its natural source. In some embodiments, the polynucleotide or polypeptide can be found in the presence of only a solvent, buffer, ion, or other components normally present in a solution of the same. The terms "isolated" and "purified" do not encompass polynucleotides or polypeptides present in their natural source.

As used herein, "recombinant polypeptides" include polypeptides or proteins derived from recombinant expression systems, for example, microbial, insect, or mammalian expression systems. Polypeptides or proteins expressed in most bacterial cultures will be free of glycosylation modifications; polypeptides or proteins expressed in yeast can have a glycosylation pattern in general different from those expressed in mammalian cells.

The term "expression vector" refers to a plasmid or phage or virus or vector, for expressing a polypeptide from a DNA or RNA sequence. An expression vector can include a transcriptional unit comprising an assembly of a genetic element or elements having a regulatory role in gene expression, for example, promoters or enhancers, a structural or coding sequence which is transcribed into mRNA and translated into protein, and appropriate transcription initiation and termination sequences. Structural units intended for use in yeast or eukaryotic expression systems can include a leader sequence enabling extracellular secretion of translated protein by a host cell. Alternatively, where recombinant protein is expressed without a leader or transport sequence, it can include an amino terminal methionine residue. This residue may be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems can be used to express heterologous polypeptides or proteins upon induction of the regulatory elements linked to the DNA segment or synthetic gene to be expressed. This term includes host cells which have stably integrated a recombinant genetic element or elements having a regulatory role in gene expression, for example, promoters or enhancers. Recombinant expression systems can be used to express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly, for example soluble proteins, or partially, for example receptors, from the cell in which they are expressed. "Secreted" proteins also include proteins transported across the membrane of the endoplasmic reticulum. "Secreted" proteins also include those non-typical signal sequences.

Where desired, an expression vector may be designed to contain a "signal sequence" which will direct the polypeptide through the membrane of a cell. A signal sequence can be naturally present on the polypeptides or provided from heterologous protein sources.

As used herein, "substantially equivalent" or "substantially similar" can refer both to nucleotide and amino acid sequences, for example a variant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35%. For example, the number of individual residue substitutions, additions, and/or deletions in a substantially equivalent sequence, as compared to the corresponding reference sequence, divided by the total number of residues in the substantially equivalent sequence is about 0.35 or less. A substantially equivalent sequence includes sequences with 65% sequence identity to the reference sequence. A substantially equivalent sequence of the invention can vary from a reference sequence by no more than 30% (70% sequence identity), no more than 25% (75% sequence identity), no more than 20% (80% sequence identity), no more than 10% (90% sequence identity), or no more that 5% (95% sequence identity). Substantially equivalent amino acid sequences according to the invention preferably have at least 80% sequence identity with a reference amino acid sequence, at least 85% sequence identity, at least 90% sequence identity, at least 95% sequence identity, at least 98% sequence identity, or at least 99% sequence identity. Substantially equivalent polynucleotide sequences of the invention can have lower percent sequence identities, taking into account, for example, the redundancy or degeneracy of the genetic code. Preferably, the polynucleotide sequence has at least about 65%, at least about 75%, at least about 80%, at least 85%, at least 90%, at least 95%, at least 98%, or at least 99% sequence identity. Sequences having substantially equivalent biological activity and substantially equivalent expression characteristics are considered substantially equivalent. Identity between sequences can be determined by methods known in the art, such as by alignment of the sequences or varying hybridization conditions.

As used herein the term "effective amount" or "therapeutically effective amount" means a dosage sufficient to treat, inhibit, or alleviate spinal pain in a subject in need thereof.

By "degenerate variant" can be intended nucleotide fragments which differ from a nucleic acid fragment of the present invention (e.g., an ORF) by nucleotide sequence but, due to the degeneracy of the genetic code, encode an identical polypeptide sequence.

The terms "polypeptide", "peptide", and "protein" can be used interchangeably and can refer to a polymer of amino acid residues or a variant thereof. Amino acid polymers can have one or more amino acid residues and can be an artificial chemical mimetic of a corresponding naturally occurring amino acid, as well as to naturally occurring amino acid polymers, those containing modified residues, and non-naturally occurring amino acid polymers. A variant polypeptide can have at least one amino acid sequence alteration as compared to the amino acid sequence of the corresponding wild-type polypeptide. An amino acid sequence alteration can be, for example, a substitution, a deletion, or an insertion of one or more amino acids. A variant polypeptide can have any combination of amino acid substitutions, deletions or insertions. An amino acid sequence alteration can be formed by altering the nucleotide sequence from which it is derived, such as a mutation, for example, a frameshift mutation, nonsense mutation, missense mutation, neutral mutation, or silent mutation. For example, sequence differences, when compared to a wild-type nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid, for example, if the change in the nucleic acid sequence causes a frame shift, the frame shift can result in a change in the encoded amino acids, and/or can result in the generation of a premature stop codon, causing generation of a truncated polypeptide.

The term "fragment" can refer to any subset of the polypeptide that can be a shorter polypeptide of the full length protein. Fragments of A2M can include 20, 30, 40, 50 or more amino acids from A2M that can be detected with anti-A2M antibodies. Other fragments of A2M include various domains of A2M and combinations thereof.

"Platelet-rich plasma" ("PRP") refers to blood plasma enriched with platelets.

Variant A2M Polypeptides Compositions for Therapy

A2M is a general inhibitor of metalloproteases and other proteases such as ADAMTS 4 and ADAMTS 5. These proteases and others produced as a result of or prior of degeneration and inflammation can be responsible for cartilage and disc degeneration and pain in synovial joints, the spine, tendons and ligaments, and other joints, entheses and general tissues. Any of the recombinant compositions described herein can be used for treatment of a subject with a condition, disease, pain or inflammation according to any of the methods described herein.

A2M is able to inactivate an enormous variety of proteases (including serine-, cysteine-, and aspartic-metalloproteases). A2M can function as an inhibitor of fibrinolysis by inhibiting plasmin and kallikrein. A2M can function as an inhibitor of coagulation by inhibiting thrombin. Human A2M has in its structure a 38 amino acid "bait" region. The bait region varies widely in the amino acid number (27-52 amino acids) and sequence between animal species. Proteases binding and cleaving of the bait region can become bound to A2M. The protease-A2M complex can be recognized by macrophage receptors and cleared from the organism's system. A2M is able to inhibit all four classes of proteases by a unique 'trapping' mechanism. When a protease cleaves the bait region, a conformational change can be induced in the protein which can trap the protease. The entrapped enzyme can remain active against low molecular weight substrates (activity against high molecular weight substrates can be greatly reduced). Following cleavage in the bait region a thioester bond can be hydrolyzed and can mediate the covalent binding of the protein to the protease.

In one aspect, provided herein is a composition that can be a variant A2M polypeptide. A variant A2M polypeptide can be a recombinant protein, or fragments thereof, and can be produced in a host cell and purified for use in treatment of pain and inflammation conditions and diseases. A variant A2M composition can be more efficient in inhibiting proteases, have longer half-life, have a slower clearance factor, or any combination thereof compared to a wild-type A2M. A variant A2M can be a recombinant protein, or a fragment thereof, and can be produced in a host cell and purified. For example, a variant A2M recombinant protein can be produced in a host comprising bacteria, yeast, fungi, insect, or mammalian cells, or a cell free system.

Variant A2M polypeptides or fragments thereof, can also be variants or posttranslationally modified variants of A2M. A2M variant polypeptides can have an integer number of amino acid alterations such that their amino acid sequence shares at least about 60%, 70%, 80%, 85%, 90%, 95%, 97%, 98%, 99%, 99.5% or 100% identity with an amino acid sequence of a wild type A2M polypeptide. In some embodiments, A2M variant polypeptides can have an amino acid sequence sharing at least about 60%, 70%, 80%, 85%, 90%, 95%, 97%, 98%, 99%, 99.5% or 100% identity with the amino acid sequence of a wild type A2M polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The Smith Waterman algorithm can also be used to determine percent identity. Exemplary parameters for amino acid sequence comparison include the following: 1) algorithm from Needleman and Wunsch (J. Mol. Biol., 48:443-453 (1970)); 2) BLOSSUM62 comparison matrix from Hentikoff and Hentikoff (Proc. Nat. Acad. Sci. USA., 89:10915-10919 (1992)) 3) gap penalty=12; and 4) gap length penalty=4. A program useful with these parameters can be publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity—(the number of identical residues)/(alignment length in amino acid residues)*100. For this calculation, alignment length includes internal gaps but does not include terminal gaps Variant A2M polypeptides, or fragments thereof, include but are not limited to, those containing as a primary amino acid sequence all or part of one or more of the amino acid sequence encoded by SEQ ID NOs: 6-83, and fragments of these proteins, including altered sequences in which functionally equivalent amino acid residues are substituted for residues within the sequence resulting in a silent change. The variant A2M polypeptides can include all or part of the amino acid sequence encoded by SEQ ID NO: 3. The variant A2M polypeptides can be, for example, any number of between 4-20, 20-50, 50-100, 100-300, 300-600, 600-1000, 1000-1450 consecutive amino acids containing one or more amino acids sequences of SEQ ID NOs: 6-83. The variant A2M polypeptide can be less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, and 1450 amino acids in length and contain, as part of the sequence one or more sequences of SEQ ID NOs: 6-83. Variant A2M polypeptides includes polypeptide sequences having at least 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% sequence identity or similarity to any variant A2M polypeptide containing one or more sequences of SEQ ID NOs: 6-83.

The variant A2M polypeptides provided herein also include proteins characterized by amino acid sequences similar to those of purified proteins but into which modification are naturally provided or deliberately engineered. For example, modifications, in the variant A2M peptide or variant A2M DNA sequence, can be made by those skilled in the art using known techniques. Modifications of interest in the protein sequences can include the alteration, substitution, replacement, insertion or deletion of a selected amino acid residue in the coding sequence. For example, one or more of the cysteine residues can be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involves systematic substitution of single or multiple amino acids with alanine, followed by testing the resulting alanine-containing variant for biological activity. This type of analysis can be used to determine the importance of the substituted amino acid(s) in biological activity.

The bait region of A2M is a segment that is susceptible to proteolytic cleavage, and which, upon cleavage, initiates a conformational change in the A2M molecule resulting in the collapse of the structure around the protease. For the exemplary A2M sequences set forth in SEQ ID NO: 3, the bait region corresponds to amino acids 690-728. For the exemplary A2M sequences set forth in SEQ ID NO: 1 and 2, the bait region corresponds to the nucleotides encoding amino acids 690-728 (SEQ ID NO: 5).

A variant A2M polypeptide can comprise a bait region that is a variant of the bait region of wild-type A2M. For example, a bait region of a variant A2M polypeptide can be a mutant bait region, fragment of a bait region, a bait region from another species, an isoform of a bait region, or a bait region containing multiple copies of one or more protease recognition sites and/or bait regions described herein, or any combination thereof. A bait region of a variant A2M polypeptide can include a plurality of protease recognition sites arranged in series and can be arranged in any order.

In some instances, a variant A2M polypeptide can comprise a sequence that is substantially the same as wild type-A2M with respect to non-bait regions. For example, a variant A2M polypeptide can comprise a non-bait region sequence that least about 60%, 70%, 80%, 85%, 90%, 95%, 96%, 97%, 98%, 99%, 99.5%, 99.8%, 99.9%, or 100% identity to the corresponding non-bait region sequence of wild-type A2M.

A bait region of a variant A2M polypeptide can have one or more variant bait regions comprising a sequence of at least about 60%, 70%, 80%, 85%, 90%, 95%, 96%, 97%, 98%, 99%, 99.5%, 99.8%, 99.9%, or 100% identity to any one of SEQ ID NOs: 6-30. A bait region of a variant A2M polypeptide can have one or more consensus protease recognition sites. For example, a bait region of a variant A2M polypeptide can have 2 or more, or 3, 4, 5, 6, 7, 8, 9, or 10 or more protease recognition sites. A bait region of a variant A2M polypeptide can have one or more protease recognition sites. A bait region of a variant A2M polypeptide can have one or more protease recognition sites comprising a sequence of at least about 60%, 70%, 80%, 85%, 90%, 95%, 96%, 97%, 98%, 99%, 99.5%, 99.8%, 99.9%, or 100% identity to any one of SEQ ID NOs: 31-81. A bait region of a variant A2M polypeptide can have one or more protease recognition sites comprising a sequence of SEQ ID NO: 82 or SEQ ID NO: 83. A bait region of a variant A2M polypeptide can have one or more consensus protease recognition sites. For example, a bait region of a variant A2M polypeptide can have 2 or more, or 3, 4, 5, 6, 7, 8, 9, or 10 or more protease recognition sites. Exemplary protease recognition sites are set forth in Table 2.

Protease recognition sites or substrate bait regions can be consensus sequences for serine proteases, threonine proteases, cysteine proteases, aspartate proteases, metalloproteases, glutamic acid proteases, or any combination thereof compared to a wild type A2M protein. A variant A2M polypeptide can be characterized by at least a 10% increased inhibition of or more proteases (e.g., types of proteases). For example, a variant A2M can be characterized by at least a 15%, 20%, 30%, 40%, 50%, 60%, 70, 80%, 90%, 1090%, 120%, 140%, 150%, 160%, 180%, 200%, 220%, 240%, 260%, 280%, 300%, 350%, 400%, 450%, or 500%, or higher enhanced inhibition of one or more serine proteases, threonine proteases, cysteine proteases, aspartate proteases, metalloproteases, glutamic acid proteases, or any combination thereof compared to a wild type A2M protein. A variant A2M polypeptide can be characterized by an enhanced specific inhibition of serine proteases, threonine proteases, cysteine proteases, aspartate proteases, metalloproteases, glutamic acid proteases, or any combination thereof. For example, a variant A2M can be characterized by at least a 15%, 20%, 30%, 40%, 50%, 60%, 70, 80%, 90%, 1090%, 120%, 140%, 150%, 160%, 180%, 200%, 220%, 240%, 260%, 280%, 300%, 350%, 400%, 450%, or 500%, or higher enhanced specific inhibition of serine proteases, threonine proteases, cysteine proteases, aspartate proteases, metalloproteases, glutamic acid proteases, or any combination thereof compared to a wild type A2M protein. A variant A2M polypeptide can be characterized by an enhanced nonspecific inhibition of serine proteases, threonine proteases, cysteine proteases, aspartate proteases, metalloproteases, glutamic acid proteases, or any combination thereof compared to a wild type A2M protein. For example, a variant A2M can be characterized by at least a 15%, 20%, 30%, 40%, 50%, 60%, 70, 80%, 90%, 1090%, 120%, 140%, 150%, 160%, 180%, 200%, 220%, 240%, 260%, 280%, 300%, 350%, 400%, 450%, or 500%, or higher enhanced nonspecific inhibition of serine proteases, threonine proteases, cysteine proteases, aspartate proteases, metalloproteases, glutamic acid proteases, or any combination thereof compared to a wild type A2M protein. Inhibition of protease activity of exemplary variant A2M polypeptides can be seen in Table 3. Inhibition of protease activity of other exemplary variant A2M polypeptides can be seen in Tables 4a and 4b.

A bait region of a variant A2M polypeptide can have one or more mutant base regions. For example, a bait region of a variant A2M polypeptide can have 2 or more, or 3, 4, 5, 6, 7, 8, 9, or 10 or more mutant base regions. A bait region of a variant A2M polypeptide can have one or more bait region fragments. For example, a bait region of a variant A2M polypeptide can have 2 or more, or 3, 4, 5, 6, 7, 8, 9, or 10 or more bait region fragments. A fragment of a bait region of a variant A2M polypeptide can be a fragment of one or more sequences of SEQ ID NOs: 6-83.

A bait region of a variant A2M polypeptide can have one or more mutant amino acids that are different than those amino acids in a wild-type A2M polypeptide. For example, a bait region of a variant A2M polypeptide can have 2 or more, or 3, 4, 5, 6, 7, 8, 9, or 10 or more mutant amino acids that are different than those amino acids in a wild-type A2M polypeptide. A bait region of a variant A2M polypeptide can have one or more mutant amino acid regions that are different than those regions in a wild-type A2M polypeptide. For example, a bait region of a variant A2M polypeptide can have 2 or more, or 3, 4, 5, 6, 7, 8, 9, or 10 or more mutant amino acid regions that are different than those regions in a wild-type A2M polypeptide. A mutant bait region of a variant A2M polypeptide can replace or substitute a bait region in a wild-type A2M polypeptide. A mutant bait region of a variant A2M polypeptide can comprise one or more sequences of any of SEQ ID NOs: 6-83.

The A2M variant polypeptides provided herein also include A2M variant proteins characterized by conservative amino acid sequences. Isolated or purified variant A2M polypeptides can have one or more amino acid residues within the polypeptide that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

A bait region of a variant A2M polypeptide can have one or more bait region isoforms. For example, a bait region of a variant A2M polypeptide can have 2 or more, or 3, 4, 5, 6, 7, 8, 9, or 10 or more bait region isoforms. A bait region of a variant A2M polypeptide can have one or more mutant or engineered bait regions. For example, a bait region of a variant A2M polypeptide can have 2 or more, or 3, 4, 5, 6, 7, 8, 9, or 10 or more mutant or engineered bait regions.

A bait region of a variant A2M polypeptide can have one or more copies of one or more bait regions. The one or more bait regions can be the same bait regions (repeats), different bait regions, or any combination thereof. For example, a bait region of a variant A2M polypeptide can have 2 or more, or 3, 4, 5, 6, 7, 8, 9, or 10 or more copies of one or more bait regions, wherein the one or more bait regions can be the same bait regions (repeats), different bait regions, or any combination thereof.

A variant A2M polypeptide can comprise one or more bait regions derived from different organisms, different species of an organism, or a combination thereof. For example, a variant A2M polypeptide can have 2 or more, or 3, 4, 5, 6, 7, 8, 9, or 10 or more bait regions derived from different organisms, different species of an organism, or a combination thereof. One or more bait regions derived from different organisms can be derived from one or more different organisms and not from different species of an organism. For example, one or more modified bait regions can be derived from 2 or more, or 3, 4, 5, 6, 7, 8, 9, or 10 or more different organisms and not contain 2 or more bait regions derived from different species of an organism. One or more bait regions derived from different species of an organism can be derived from one or more different species of an organism and not from different organisms. For example, one or more modified bait regions can be derived from 2 or more, or 3, 4, 5, 6, 7, 8, 9, or 10 or more different species of an organism and not contain 2 or more bait regions derived from different organism. The modified bait regions can be derived from any animal, insect, plant, bacteria, viral, yeast, fish, reptile, amphibian, or fungi. The modified bait regions can be derived from any animal with A2M or homologous protein, such as pig, mouse, rat, rabbit, cat, dog, frog, monkey, horse or goat.

A variant A2M polypeptide can comprise one or more bait regions of variant A2M polypeptides. For example, a variant A2M polypeptide can have 2 or more, or 3, 4, 5, 6, 7, 8, 9, or 10 or more bait region of variant A2M polypeptides. One or more bait region of variant A2M polypeptides can be derived from one or more different species. For example, one or more bait regions of variant A2M polypeptides can be derived from 2 or more, or 3, 4, 5, 6, 7, 8, 9, or 10 or more different species. The bait region of variant A2M polypeptides can be derived from any animal, insect, plant, bacteria, viral, yeast, fish, reptile, amphibian, or fungi species.

A variant A2M polypeptide can have a plurality of protease recognition sites that can be one or more protease substrate bait regions from one or more proteins other than A2M.

A variant A2M polypeptide can have a plurality of protease recognition sites that can be one or more protease substrate bait regions from A2M. A variant A2M polypeptide can have a plurality of protease recognition sites that can be one or more protease substrate bait regions from one or more non-natural protein sequences. The non-natural protein sequences can comprise one or more protease recognition sites in series and can function as bait for proteases. A variant A2M polypeptide can have a plurality of protease recognition sites that can be one or more protease substrate bait regions from or any of the combination of bait regions described herein. A variant A2M polypeptide can have any number of protease bait regions arranged in series. A variant A2M polypeptide can have any number of protease bait regions from any species and can be arranged in series. One or more protease substrate bait regions from one or more proteins other than A2M or from the one or more non-natural protein sequences can be a suicide inhibitor. For example, a variant A2M polypeptide can have 2, 3, 4, 5, 6, 7, 8, 9, 10, 11, 12, 13, 14, 15, or more suicide inhibitor bait regions. A suicide inhibitor can be operable to covalently attach a protease to A2M. Examples of known recognition sequences for exemplary ADAMTSs and MMPs in human aggrecan are indicated in Table 1. Dash shows location of proteolysis.

TABLE 1

| Protease | Aggrecan Cleavage Site Sequence |
|---|---|
| ADAMTSs | 370 NITEGE-ARGS 377 |
| ADAMTSs | 1540 TASELE-GRGTI 1550 |
| ADAMTSs | 1709 TFKEEE-GLGSV 1719 |
| MMP-8 | 370 NITEGE-ARGS377 |
| MMPs | 336 VDIPEN-FFG 344 |
| MMP-3 | 374 ARGS-V 378 |
| MMP-13 | 379 ILTVKP-IFEV 388 |

A variant A2M polypeptide can be characterized by at least about a 10% increase in protease inhibitory effectiveness compared to the protease inhibitory effectiveness of a wild type A2M protein. For example, a variant A2M polypeptide can be characterized by at least about a 20, 25%, 30%, 35%, 40%, 45%, 50%, 55%, 60%, 65%, 70%, 75%, 80%, 85%, 90%, 95%, or 100% increase in protease inhibitory effectiveness when compared to the protease inhibitory effectiveness of a wild type A2M protein. A variant A2M polypeptide can be characterized by an increase in protease inhibitory effectiveness compared to the protease inhibitory effectiveness of a wild type A2M protein. For example, a variant A2M polypeptide can be characterized by an 1.2, 1.2, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times increase in protease inhibitory effectiveness compared to the protease inhibitory effectiveness of a wild type A2M protein.

A variant A2M polypeptide can be characterized as having an increased ability to inhibit one or more proteases compared to a wild-type A2M polypeptide. A variant A2M polypeptide can have an ability to inhibit one or more proteases that is at least 1.5 times higher than the ability of a wild-type A2M polypeptide to inhibit the one or more proteases. For example, a variant A2M polypeptide can have an ability to inhibit one or more proteases that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to inhibit the one or more proteases. A variant A2M polypeptide can have an ability to inhibit one or more proteases that is from 1.5-100 times higher than the ability of a wild-type A2M polypeptide to inhibit the one or more proteases. For example, a variant A2M polypeptide can have an ability to inhibit one or more proteases that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to inhibit the one or more proteases.

The one or more proteases can include a matrix metalloprotease, such as MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11 (Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xco14, Xenopus collagenase), MMP19 (RASI-1, stromelysin-4), MMP20 (Enamelysin), MMP21 (X-MMP), MMP23A (CA-MMP), MMP23B, MMP24 (MT5-MMP), MMP25 (MT6-MMP), MMP26 (Matrilysin-2, endometase), MMP27 (MMP-22, C-MMP), MMP28 (Epilysin); A Disintegrin and Metalloproteinase with Thrombospondin Motifs protease, such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMPSTE2; ZMPSTE4; ZMPSTE24; and acetylcholinesterase.

A variant A2M polypeptide can be characterized as having an increased ability to prevent FAC formation compared to a wild-type A2M polypeptide. A variant A2M polypeptide can have an ability to prevent FAC formation that is at least 1.5 times higher than the ability of a wild-type A2M polypeptide to prevent FAC formation. For example, a variant A2M polypeptide can have an ability to prevent FAC formation that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to prevent FAC formation. A variant A2M polypeptide can have an ability to prevent FAC formation that is from 1.5-100 times higher than the ability of a wild-type A2M polypeptide to prevent FAC formation. For example, a variant A2M polypeptide can have an ability to prevent FAC formation that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to prevent FAC formation.

One aspect of the invention is a method for determining the enhanced inhibition of a protease by a variant A2M polypeptide comprising: a) providing a variant A2M polypeptide comprising a sequence of one or more of SEQ ID NOs 6-83; b) contacting the variant A2M polypeptide with the protease and a substrate cleaved by the protease; c) contacting a wild-type A2M polypeptide with the protease and the substrate cleaved by the protease; and d) comparing the amount of cleavage of the substrate from step b) to the amount of cleavage of the substrate from step c), thereby determining the enhanced inhibition of the protease by the variant A2M polypeptide.

Enzymatic glycoconjugation reactions can be targeted to glycosylation sites and to residues that are attached to glycosylation sites. The targeted glycosylation sites can be sites native to a wild-type A2M protein, native to a variant A2M polypeptide or, alternatively, they can be introduced into a wild-type A2M or variant A2M polypeptide by mutation. Thus, a method for increasing the in vivo half-life of a variant A2M polypeptide is provided by the methods of the invention.

A variant A2M polypeptide can include an amino acid sequence that mutated to insert, remove or relocate one or more glycosylation site in the protein. When a site is added or relocated, it is not present or not present in a selected location in the wild-type A2M peptide. The mutant glycosylation site can be a point of attachment for a modified glycosyl residue that can be enzymatically conjugated to the glycosylation site. Using the methods of the invention, the glycosylation site can be shifted to any efficacious position on the peptide. For example, if the native glycosylation site is sufficiently proximate or within the bait region of variant A2M polypeptide peptide that conjugation interferes with the ability to bind a protease, inhibit a protease, or a combination thereof, it is within the scope of the invention to engineer a variant A2M polypeptide that includes a glycosylation site as modified or removed from the bait as necessary to provide a biologically active variant A2M polypeptide.

Any glycosyltransferase or method of their use known in the art can be used for in vitro enzymatic synthesis of variant A2M polypeptides with custom designed glycosylation patterns, various glycosyl structures, or a combination thereof possible. See, for example, U.S. Pat. Nos. 5,876,980; 6,030,815; 5,728,554; 5,922,577; and WO/9831826; US2003180835; and WO 03/031464.

A variant A2M polypeptide can comprise one or more consensus sequences for a protease. A variant A2M polypeptide can comprise one or more protease recognition sites/sequences in Table 2.

TABLE 2

Exemplary variant A2M protease recognition sequences of bait regions for indicated protease

| Type | Protease | Protease Recognition/ Cleavage Site Sequence |
|---|---|---|
| Aggrecan cleavage sites | ADAMTS<br>MMP | TAQEAGEG, VSQELGQR<br>IPENFFGV, SEDLVVQI, EAIPMSIPT |
| General or Multiple cleavage sites | ADAMTS general<br>EXE-$_{\Theta4}$XG<br>where $\Theta$ is G, V, E, A, T, S, Q, P, N, or D<br>where X is any amino acid<br>MMP general<br>(G/P/E)XX(G/E)-$\Phi$XXG<br>where $\Phi$ is G, V, L. S, A, F, or T<br>where X is any amino acid | ELEGRG, EEEGLG, EEEGGG, ESESEG, EFEVEG, EIEEGG, ERESTG, EREAQG, EKETGG, EREAQG, ETEGRG, ENEAGG, EPESSG, EPESSG, ESESEG, EGEQEG, EPEPEG, EREAQG, EAEGTG, EFPEVEG GEEGVEEG, GARGLEG, GPPGLAPG, GYPGSSRG, GFAGLPNG, GGGGSLLG, GPAGAARG, GLEGGGGG, GGGGSLLG, GFFGFPIG, EPAGAARG, GDRGLPIG, GEPEGAKG, GFKEGVEG, GVEGVELG, GFKEGVEG, GERGVLG, GGGSLLG, PEEGVEEG, GFKEGVEG, GFKEGVEG, GEPEGAKG |

TABLE 2-continued

Exemplary variant A2M protease recognition sequences of bait regions for indicated protease

| Type | Protease | Protease Recognition/Cleavage Site Sequence |
|---|---|---|
| | MMP and ADAMTS cleavage | TEGEARGS |
| Consensus Sequences | ADAMTS | EGEGEGEG |
| | ADAMTS-4 | EFRGVT |
| | MMP-2 | PRYLTA |

TABLE 3

Variant A2M protease inhibition (% of wild-type) for indicated protease
Protease Inhibition (% of WT)

| Bait Region | Aggrecanases | | Collagenases | | | Gelatinases | | Stromolysin | Inflammatory Proteases | | Matrilysin |
|---|---|---|---|---|---|---|---|---|---|---|---|
| SEQ ID NO: | ADAMTS4 | ADAMTS5 | MMP1 | MMP8 | MMP13 | MMP2 | MMP9 | MMP3 | Elastase | Cathepsin G | MMP7 |
| 6 | | | | | | | | | | | |
| 7 | 222 | 79 | 117 | 81 | 145 | 58 | 39 | 127 | 131 | 157 | 147 |
| 8 | 120 | 97 | 48 | 28 | 56 | 33 | 9 | <100 | 39 | 12 | 64 |
| 9 | 124 | 145 | 67 | 33 | 88 | 27 | 20 | 27 | 93 | 66 | 80 |
| 10 | 159 | 412 | 111 | 38 | 128 | 25 | 16 | 27 | 106 | 134 | 191 |
| 11 | | | | | | | | | | | |
| 12 | 208 | 440 | 108 | 54 | 72 | 16 | 0 | 182 | 117 | 105 | 160 |
| 13 | 290 | 194 | 91 | 81 | 76 | 65 | 71 | 189 | 97 | 54 | 128 |
| 14 | 236 | 105 | 60 | 39 | 66 | 10 | 14 | 169 | 67 | 99 | 61 |
| 15 | 83 | 183 | 116 | 77 | 143 | 59 | 41 | 40 | 115 | 139 | 157 |
| 16 | 50-150 | 305 | 101 | 92 | 104 | 92 | 84 | 180 | 91 | 105 | 105 |
| 17 | | | | | | | | | | | |
| 18 | 0-100 | 154 | 91 | 82 | 117 | 58 | 53 | 38 | 86 | 83 | 102 |
| 19 | 0-330 | 530 | 100 | 51 | 89 | 36 | 39 | 140 | 115 | 90 | 137 |
| 20 | 201 | 246 | 119 | 64 | 100 | 37 | 41 | 122 | 124 | 117 | 170 |
| 21 | 68 | 217 | 84 | 39 | 46 | 66 | 45 | 26 | 59 | 58 | 94 |
| 22 | 104 | 316 | 68 | 54 | 93 | 42 | 30 | 265 | 92 | 78 | 75 |
| 23 | 176 | 200 | 133 | 132 | 133 | 80 | 71 | 111 | 147 | 145 | 191 |
| 24 | | | | | | | | | | | |
| 25 | 144 | 376 | 101 | 36 | 138 | 43 | 25 | 86 | 100 | 117 | 140 |
| 26 | | | | | | | | | | | |
| 27 | 50-150 | 114 | 109 | 43 | 54 | 16 | 13 | 33 | 79 | 161 | 138 |
| 28 | 180 | 398 | 67 | 38 | 90 | 36 | 14 | 129 | 75 | 69 | 94 |
| 29 | 100-390 | 85 | 87 | 29 | 70 | 16 | 5 | 101 | 98 | 84 | 104 |
| 30 | 93 | 296 | 67 | 29 | 96 | 3 | 18 | <100 | 55 | 104 | 91 |

TABLE 4

Variant A2M protease inhibition (% of wild-type) of indicated protease
Protease Inhibition (% of WT)

| Bait Region | Inflammatory Proteases | | Protease Mixtures | | Misc Serine Proteases | | Matrilysin |
|---|---|---|---|---|---|---|---|
| | | | IGD | Collagen | | | |
| SEQ ID NO | Elastase | Cathepsin G | Substrate | Substrate | Trypsin | Chymotrypsin | MMP-7 |
| 84 | 75 | | | | 100 | 71 | |
| 85 | | | | | | | |
| 86 | | | | | | | |
| 87 | | | | | | | |
| 88 | | | | | | | |
| 89 | | | | | | | |
| 90 | 550 | | | | 100 | 80 | |
| 91 | | | | | | | |
| 92 | | | | | | | |
| 93 | | | | | | | |
| 94 | | | | | | | |
| 95 | | | | | | | |
| 96 | 50 | | | | 100 | | |
| 97 | | | | | | | |
| 98 | | | | | | | |
| 99 | | | | | | | |
| 100 | | | | | | | |

TABLE 4-continued

Variant A2M protease inhibition (% of wild-type) of indicated protease
Protease Inhibition (% of WT)

| Bait Region SEQ ID NO | Aggrecanases | | Collagenases | | | Gelatinases | | Stromolysin | Metalloelastase |
|---|---|---|---|---|---|---|---|---|---|
| | ADAMTS4 | ADAMTS5 | MMP1 | MMP8 | MMP13 | MMP2 | MMP9 | MMP3 | MMP12 |
| 101 | | | | | | | | | |
| 102 | | | | | | | | | |
| 103 | | | | | | | | | |
| 104 | | | | | | | | | |
| 105 | | | | | | | | | |
| 106 | | | | | | | | | |
| 107 | | | | | | | | | |
| 108 | 50 | | | | | | 100 | 100 | |
| 109 | | | | | | | | | |
| 110 | | | | | | | | | |
| 111 | | | | | | | | | |
| 112 | | | | | | | | | |
| 113 | | | | | | | | | |
| 114 | | | | | | | | | |
| 115 | | | | | | | | | |
| 116 | | | | | | | | | |
| 117 | | | | | | | | | |
| 118 | | | | | | | | | |
| 119 | | | | | | | | | |
| 120 | | | | | | | | | |
| 121 | | | | | | | | | |
| 122 | | | | | | | | | |
| 123 | | | | | | | | | |
| 124 | 75 | 250 | | | 237 | | | | |
| 125 | 75 | 250 | | | 150 | | | | |
| 126 | 105 | 311 | | | 229 | 250 | 86 | 50 | |
| 127 | 102 | 324 | | | 229 | 180 | 84 | 25 | |
| 128 | 100 | 225 | | | 125 | | | | |
| 129 | 75 | | | | 160 | | | | |
| 130 | 103 | 311 | | | | 250 | 100 | | |
| 131 | 300 | 200 | | | 150 | | | | |
| 132 | 300 | 437 | | | 243 | 120 | 20 | 10 | |
| 133 | 350 | 100 | | | 75 | | | | |
| 134 | 300 | 250 | | | 220 | | | | |
| 135 | 300 | 100 | | | 140 | | | | |
| 136 | 250 | 376 | | | 215 | 170 | 221 | 25 | |
| 137 | 100 | 450 | | | 140 | | | | |
| 138 | 250 | 100 | | | 210 | | | | |
| 139 | 200 | 200 | | | 190 | | | | |
| 140 | | | | | | | | | |
| 141 | 75 | 100 | | | | | | | |
| 142 | 200 | 300 | | | 140 | | | | |
| 143 | 250 | 350 | | | 110 | | | | |
| 84 | 70 | 250 | 180 | 350 | 720 | 120 | 60 | 170 | 100 |
| 85 | 78 | 174 | | | 170 | | | | |
| 86 | 91 | 74 | | | 120 | | | | |
| 87 | 160 | 170 | 150 | 40 | 150 | 100 | 70 | 40 | |
| 88 | 68 | 108 | | | 156 | | | | |
| 89 | 101 | 485 | | | 18 | | | | |
| 90 | 70 | 350 | 50 | 110 | 700 | 110 | 100 | 110 | 100 |
| 91 | | | | | | | | | |
| 92 | 210 | 250 | 170 | 160 | 90 | 110 | 50 | 80 | |
| 93 | 27 | 66 | | | 119 | | | | |
| 94 | 121 | 395 | | | 173 | | | | |
| 95 | 153 | 272 | | | 79 | | | | |
| 96 | 250 | 350 | 100 | 50 | 200 | 100 | 70 | 80 | 100 |
| 97 | 131 | 128 | | | 116 | | | | |
| 98 | 124 | 82 | | | 148 | | | | |
| 99 | 63 | 87 | | | 64 | | | | |
| 100 | 50 | 400 | 40 | 20 | 210 | 110 | 50 | 50 | |
| 101 | 168 | 97 | | | 124 | | | | |
| 102 | 187 | 354 | | | 127 | | | | |
| 103 | 168 | 309 | | | 52 | | | | |
| 104 | 100 | 99 | | | 80 | | | | |
| 105 | 94 | 115 | | | 164 | | | | |
| 106 | 104 | 93 | | | 16 | | | | |
| 107 | 92 | 108 | | | 136 | | | | |
| 108 | 50 | 90 | 390 | 40 | 350 | 110 | 70 | 330 | |
| 109 | 112 | 105 | | | 122 | | | | |
| 110 | 101 | 208 | | | 51 | | | | |
| 111 | 105 | 89 | | | 113 | | | | |
| 112 | 108 | 199 | | | 56 | | | | |

TABLE 4-continued

Variant A2M protease inhibition (% of wild-type) of indicated protease
Protease Inhibition (% of WT)

| | | | | | | | | | |
|---|---|---|---|---|---|---|---|---|---|
| 113 | 115 | 92 | | 27 | | | | | |
| 114 | 118 | 237 | | 75 | | | | | |
| 115 | 108 | 163 | | 78 | | | | | |
| 116 | 107 | 92 | | 116 | | | | | |
| 117 | 100 | 190 | | 11 | | | | | |
| 118 | | | | | | | | | |
| 119 | 100 | 170 | | 90 | | | | | |
| 120 | 88 | 100 | | 121 | | | | | |
| 121 | 64 | 68 | | 115 | | | | | |
| 122 | | | | | | | | | |
| 123 | 86 | 126 | | 122 | | | | | |
| 124 | | | | | | | | | |
| 125 | | 200 | 300 | | 20 | 300 | | | 300 |
| 126 | 115 | 480 | 379 | 163 | 117 | 61 | 500 | 130 | 132 |
| 127 | 82 | 205 | 327 | 210 | 131 | 118 | 500 | 130 | 170 |
| 128 | | | 400 | | | 20 | | | |
| 129 | | | 200 | | | 20 | | | |
| 130 | 110 | 211 | 283 | 180 | 146 | 109 | 100 | | 124 |
| 131 | | | 300 | | | | | | |
| 132 | 86 | 185 | 388 | 161 | 117 | 67 | 500 | 100 | 136 |
| 133 | | | 250 | | | | | | |
| 134 | | | 200 | 200 | | | | | |
| 135 | | | 300 | | | | | | |
| 136 | 80 | 373 | 370 | 133 | 113 | 47 | 500 | 130 | 150 |
| 137 | | | | | | | | | |
| 138 | | | 200 | | | | | | |
| 139 | | | 400 | | | | | | |
| 140 | | | | | | | | | |
| 141 | | | | | | | | | |
| 142 | | | 350 | | | | | | |
| 143 | | | | | | | | | |

The present invention provides methods of improving or lengthening the in vivo half-lives of variant A2M polypeptides by conjugating a water-soluble polymer to the variant A2M polypeptides through an intact glycosyl linking group. In an exemplary embodiment, covalent attachment of polymers, such as polyethylene glycol (PEG), to such variant A2M polypeptides affords variant A2M polypeptides having in vivo residence times, and pharmacokinetic and pharmacodynamic properties, enhanced relative to the unconjugated variant A2M polypeptide.

The polymer backbone of the water-soluble polymer can be poly(ethylene glycol) (PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as $R(\text{-PEG-OH})_n$ in which R represents the core moiety, such as glycerol or pentaerythritol, and n represents the number of arms. Many other polymers are also suitable for the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), poly(hydroxypropylmethacrylamide), poly($\alpha$-hydroxy acid), poly(vinyl alcohol), polyphosphazene, polyoxazoline, poly(N-acryloylmorpholine) and copolymers, terpolymers, and mixtures thereof. Although the molecular weight of each chain of the polymer backbone can vary, it is typically in the range of from about 100 Da to about 100,000 Da often from about 6,000 Da to about 80,000 Da.

A variant A2M polypeptide can further comprise PEG. A variant A2M polypeptide can have one or more mutant or modified glycosylation sites. The modified glycosylation sites can comprise PEG. For example, a variant A2M polypeptide can have 2, 3, 4, 5, 6, 7, 8, 9, 10, 11, 12, 13, 14, 15, or more mutant or modified glycosylation sites. The conjugation or addition of PEG to a variant A2M polypeptide with one or more modified or abnormal glycosylation sites can result in a variant A2M polypeptide with a longer half-life than the half-life of a wild-type A2M protein without PEG when disposed within a subject, such as a joint or spine disc of a subject. The conjugation or addition of PEG to a variant A2M polypeptide with one or more modified or abnormal glycosylation sites can result in a variant A2M polypeptide with a longer half-life than the half-life of a variant A2M polypeptide without one or more modified glycosylation sites without PEG when disposed within a subject, such as a joint or spine disc of a subject. The conjugation or addition of PEG to a variant A2M polypeptide with one or more modified or abnormal glycosylation sites can result in a variant A2M polypeptide with a longer half-life than the half-life of a variant A2M polypeptide with one or more modified glycosylation sites without PEG when disposed within a subject, such as a joint or spine disc of a subject. For example, a variant A2M polypeptide with one or more modified or abnormal glycosylation sites with PEG can have half-life that is 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times the half-life of a wild type A2M protein without PEG, a variant A2M polypeptide with one or more modified glycosylation sites without PEG, or a variant A2M polypeptide without one or more modified glycosylation sites without PEG. For example, a variant A2M polypeptide with one or more modified or abnormal glycosylation sites with PEG can have half-life that is 2 times the half-life of a wild type A2M protein composition with one or more modified or abnormal glycosylation sites without PEG when disposed within a joint or spine disc of a subject.

The present invention further provides isolated polypeptides encoded by the nucleic acid fragments of the present invention or by degenerate variants of the nucleic acid fragments of the present invention. By "degenerate variant" can be intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

Fragments of the A2M variants of the present invention which are capable of exhibiting biological activity are also encompassed by the present invention. Fragments of the A2M variants can be in linear form or they can be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments can be fused to carrier molecules such as immunoglobulins for many purposes, including increasing the valency of protein binding sites. The present invention also provides both full-length and mature forms (for example, without a signal sequence or precursor sequence) of the disclosed A2M variants. The protein coding sequence can be identified in the sequence listing by translation of the disclosed nucleotide sequences. The mature form of such A2M variants can be obtained by expression of a full-length polynucleotide in a suitable mammalian cell or other host cell. The sequence of the mature form of the A2M variants can be also determinable from the amino acid sequence of the full-length form. Where A2M variants of the present invention are membrane bound, soluble forms of the A2M variants are also provided. In such forms, part or all of the regions causing the A2M variants to be membrane bound are deleted so that the A2M variants are fully secreted from the cell in which it can be expressed. A2M variant compositions of the present invention can further comprise an acceptable carrier, such as a hydrophilic, e.g., pharmaceutically acceptable, carrier.

Variant A2M Polynucleotide Compositions

As used herein, "A2M polynucleotide," when used with reference to SEQ ID NOs: 1 or 2, means the polynucleotide sequence of SEQ ID NO: 1 or 2, or fragments thereof, as well as any nucleic acid variants which include one or more insertions, deletions, mutations, or a combination thereof. The insertions, deletions, and mutations are preferably within the polynucleotide sequence encoding the bait region of the A2M protein. Similarly, "A2M cDNA", "A2M coding sequence" or "A2M coding nucleic acid", when used with reference to SEQ ID NOs: 1 or 2, means the nucleic acid sequences of SEQ ID NOs: 1 or 2, or fragments thereof, as well as nucleic acid variants which include one or more mutations, insertions, deletions, or a combination thereof. The A2M polynucleotides, or fragments thereof, can be manipulated using conventional techniques in molecular biology so as to create variant A2M recombinant polynucleotide constructs, encoding the variant A2M polypeptides that express variant A2M polypeptides. Variant A2M polynucleotides include nucleotide sequences having at least 99%, 98%, 97%, 96%, 95%, 94%, 93%, 92%, 91%, 90%, 89%, 88%, 87%, 86%, or 85% sequence identity to SEQ ID NOs: 1 and 2. A2M coding sequences includes nucleotide sequences having at least 99%, 98%, 97%, 96%, 95%, 94%, 93%, 92%, 91%, 90%, 89%, 88%, 87%, 86%, or 85% sequence identity to any one of SEQ ID NOs: 1 and 2.

In one aspect, provided herein is a variant A2M polynucleotide nucleotide composition. Numerous polynucleotide sequences encoding wild-type A2M proteins from various organisms have been determined. Any A2M DNA sequence identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene. Alternatively, a nucleic acid sequence encoding an A2M polypeptide can be isolated from a human cDNA or genomic DNA library using standard cloning techniques such as polymerase chain reaction (PCR), where homology-based primers can often be derived from a known nucleic acid sequence encoding an A2M polypeptide.

cDNA libraries suitable for obtaining a coding sequence for a wild-type A2M polypeptide can be obtained commercially or can be constructed. The general methods of isolating mRNA, making cDNA by reverse transcription, ligating cDNA into a recombinant vector, transfecting into a recombinant host for propagation, screening, and cloning are well known. Upon obtaining an amplified segment of nucleotide sequence by PCR, the segment can be further used as a probe to isolate the full-length polynucleotide sequence encoding the wild-type A2M protein from the cDNA library. A similar procedure can be followed to obtain a full length sequence encoding a wild-type A2M protein from a human genomic library. Human genomic libraries are commercially available or can be constructed according to various art-recognized methods. In general, to construct a genomic library, the DNA is first extracted from a tissue where a peptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage vectors. These vectors and phages are packaged in vitro. Recombinant phages are analyzed by plaque hybridization.

Based on sequence homology, degenerate oligonucleotides can be designed as primer sets and PCR can be performed under suitable conditions to amplify a segment of nucleotide sequence from a cDNA or genomic library. Using the amplified segment as a probe, the full-length nucleic acid encoding a wild-type A2M protein can be obtained Upon acquiring a nucleic acid sequence encoding a wild-type A2M protein, the coding sequence can be subcloned into a vector, for instance, an expression vector, so that a recombinant wild-type A2M protein can be expressed mutated into a variant A2M polypeptide of the invention produced from the resulting construct. Further modifications to the wild-type A2M protein coding sequence, for example, nucleotide substitutions, may be subsequently made to alter the bait region of the A2M protein.

The present invention further provides isolated polypeptides encoded by the polynucleotides, or fragments thereof, of the present invention or by degenerate variants of the polynucleotides, or fragments thereof, of the present invention. Preferred polynucleotides, or fragments thereof, of the present invention are the ORFs that encode A2M variants.

A variant A2M polynucleotide can be made by mutating the polynucleotide sequence encoding a wild-type A2M protein. This can be achieved by using any known mutagenesis methods. Exemplary modifications to a wild-type A2M polynucleotide for accepting variant bait regions described herein include those in SEQ ID NO 2. Exemplary modifications to an A2M nucleotide include inserting or substituting a nucleotide sequence encoding a variant bait region of SEQ ID NOs: 6-30 or a variant bait region comprising one or more protease recognition sequences of SEQ ID NOs 31-83, into the wild-type A2M polynucleotide sequence of SEQ ID NO: 1 and the variant A2M acceptor polynucleotide sequence of SEQ ID NO 2. Mutagenesis procedures can be used separately or in combination to produce variants of a set of nucleic acids, and hence variants of encoded polypeptides. Kits for mutagenesis are commercially available.

In one aspect, provided herein are methods of making any of the variant A2M polynucleotides. A method of making a variant A2M polynucleotide can comprise inserting or substituting a variant bait region into a wild-type A2M polynucleotide sequence or substantially similar sequence. The substantially similar sequence can be SEQ ID NO 2. One aspect of the invention is a method for making a variant A2M polynucleotide comprising: a) providing a vector containing a variant A2M polynucleotide comprising a sequence of SEQ ID NO 2; b) digesting the vector containing a variant A2M polynucleotide with restriction endonucleases to form a linear vector; c) ligating one end of the one or more polynucleotides encoding one or more of the variant bait regions of SEQ ID NOs: 6-30 or variant bait regions comprising one or more protease recognition sequences of SEQ ID NOs 31-83 to one end of the linear vector; and d) ligating the other end of the one or more polynucleotides encoding one or more of the variant bait regions of SEQ ID NOs: 6-30 or the variant bait regions comprising one or more protease recognition sequences of SEQ ID NOs 31-83 to the other end of the linear vector, thereby forming a vector containing a variant A2M polynucleotide comprising the variant bait regions of SEQ ID NOs: 6-30 or variant bait regions comprising one or more protease recognition sequences of SEQ ID NOs: 31-83.

Protein Production

A variety of methodologies known in the art can be utilized to obtain any one of the isolated A2M variant proteins of the present invention. At the simplest level, the amino acid sequence can be synthesized using commercially available peptide synthesizers. Such polypeptides can be synthesized with or without a methionine on the amino terminus. Chemically synthesized polypeptides can be oxidized using methods set forth in these references to form disulfide bridges. The synthetically constructed A2M variant sequences, by virtue of sharing primary, secondary or tertiary structural and/or conformational characteristics with A2M variants can possess biological properties in common therewith, including protease inhibitory activity. This technique can be particularly useful in producing small peptides and fragments of larger polypeptides. Fragments are useful, for example, in generating antibodies against the A2M variants. Thus, they can be employed as biologically active or immunological substitutes for natural, purified A2M variants in screening of therapeutic compounds and in immunological processes for the development of antibodies.

The A2M variant polypeptides of the present invention can alternatively be purified from cells which have been altered to express the desired A2M variant. As used herein, a cell can be said to be altered to express a desired A2M variant polypeptide or protein when the cell, through genetic manipulation, is made to produce an A2M variant polypeptide which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the A2M variant polypeptides of the present invention.

A variant A2M polypeptide can be a recombinant protein, or fragments thereof, and can be produced in a host cell or in vitro system. Recombinant polypeptides and protein promoters can be inserted in such a manner that it can be operatively produced in a host cell, for example, a bacterial culture or lower eukaryotes such as yeast or insects or in prokaryotes or any host know in the art. A variant A2M recombinant protein can be produced in a bacterium, yeast, fungi, insect, or mammalian host cell, or a cell free system. For example, a variant A2M polypeptide can be produced in *Escherichia coli, Bacillus subtilis, Salmonella typhimurium, Corynebacterium, Saccharomyces cerevisiae, Schizosaccharomyces pombe Kluyveromyces* strains, *Candida, Pichia pastoris,* baculovirus-infected insect cells, or mammalian cells such as COS cells, BHK cells, 293 cells, 3T3 cells, NS0 hybridoma cells, baby hamster kidney (BHK) cells, PER.C6™ human cells, HEK293 cells or *Cricetulus griseus* (CHO) cells. A variant A2M polypeptide can be produced by transient expression, stable cell lines, BacMam-mediated transient transduction, or cell-free protein production.

The variant A2M polypeptides can also be produced by operably linking the isolated variant A2M polynucleotides to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference.

In mammalian host cells, a number of viral-based expression systems can be utilized. In cases where an adenovirus is used as an expression vector, the variant A2M nucleotide sequence of interest can be ligated to an adenovirus transcription/translation control complex, for example, the late promoter and tripartite leader sequence. This chimeric gene can then be inserted in the adenovirus genome by in vitro or in vivo recombination. Insertion in a non-essential region of the viral genome can result in a recombinant virus that is viable and capable of expressing the variant A2M gene product in infected hosts. Specific initiation signals can also be required for efficient translation of inserted nucleotide sequences. These signals include the ATG initiation codon and adjacent sequences. In cases where an entire variant A2M gene or cDNA, including its own initiation codon and adjacent sequences, is inserted into the appropriate expression vector, for example, a pJ608 mammalian expression vector (FIG. 23) no additional translational control signals are needed. Exogenous translational control signals, such as the ATG initiation codon, can be provided.

Host cells can be genetically engineered to contain the variant A2M polynucleotides of the invention. For example, such host cells can contain variant A2M polynucleotides introduced into the host cell using known transformation, transfection or infection methods. As used herein, a cell capable of expressing a variant A2M polynucleotide can be "transformed." The variant A2M polypeptides of the invention can be prepared by culturing transformed host cells under culture conditions suitable to express the recombinant protein. Any procedure for introducing foreign nucleotide sequences into host cells may be used. Non-limiting examples include the use of calcium phosphate transfection, transfection, DEAE, dextran-mediated transfection, microinjection, lipofection, polybrene, protoplast fusion, electroporation (Davis, L. et al., *Basic Methods in Molecular Biology* (1986)), liposomes, microinjection, plasma vectors, viral vectors, and any other well-known methods for introducing cloned genomic DNA, cDNA, synthetic DNA, or other foreign genetic material into a host cell. A genetic engineering procedure capable of successfully introducing at least one gene into the host cell capable of expressing the variant A2M polynucleotide can be used.

The present invention still further provides host cells engineered to express the variant A2M polynucleotides of the invention, wherein the variant A2M polynucleotides are operative with a regulatory sequence heterologous to the host cell which drives expression of the variant A2M polynucleotides in the cell. Knowledge of A2M-like DNA allows for modification of cells to permit, or increase, expression of A2M-like polypeptide. Cells can be modified, for example, by homologous recombination, to provide increased variant A2M polypeptide expression by replacing, in whole or in part, the naturally occurring A2M derived from the SV40 viral genome, for example, SV40 macroglobulin-like promoter with all or part of a heterologous promoter so that the cells' variant A2M sites can be used to provide the required non-transcribed polypeptide and can be expressed at higher levels.

For long-term, high-yield production of recombinant variant A2M polypeptides, stable expression is preferred. For example, cell lines that stably express the variant A2M sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the variant A2M gene product. Such engineered cell lines are particularly useful in screening and evaluation of compounds that affect the endogenous activity of the variant A2M gene product. A number of selection systems can be used, including but not limited to the herpes simplex virus thymidine kinase, hypoxanthine-guanine phosphoribosyltransferase, and adenine phosphoribosyltransferase genes can be employed in tk$^-$, hgprt$^-$ or aprt$^-$ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin.

Variant A2M polynucleotide sequences can be engineered so as to modify processing or expression of the protein. For example, and not by way of limitation, the variant A2M polynucleotides can be combined with a promoter sequence and/or ribosome binding site, or a signal sequence can be inserted upstream of variant A2M polynucleotide sequences to permit secretion of the variant A2M polypeptide and thereby facilitate harvesting or bioavailability. Additionally, a variant A2M polynucleotide can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis.

Further, nucleic acids encoding other proteins or domains of other proteins can be joined to nucleic acids encoding variant A2M polypeptides or fragments thereof so as to create a fusion protein. Nucleotides encoding fusion proteins can include, but are not limited to, a full length variant or wild-type A2M protein, a truncated variant or wild-type A2M protein or a peptide fragment of a variant or wild type A2M protein fused to an unrelated protein or peptide, such as for example, a transmembrane sequence, which anchors the A2M peptide fragment to the cell membrane; an Ig Fc domain which increases the stability and half-life of the resulting fusion protein; maltose binding protein (MBP), glutathione-S-transferase (GST) or thioredoxin (TRX), a His tag, an enzyme, fluorescent protein, luminescent protein which can be used as a marker, for example, an A2M-Green Fluorescent Protein fusion protein. The fusion proteins can be used for affinity purification.

The variant A2M nucleic acids and polypeptides can also be expressed in organisms so as to create a transgenic organism. Desirable transgenic plant systems having one or more of these sequences include *Arabidopsis*, Maize, and *Chlamydomonas*. Desirable insect systems having one or more of the variant A2M polynucleotides and/or polypeptides include, for example, *D. melanogaster* and *C. elegans*. Animals of any species, including, but not limited to, amphibians, reptiles, birds, mice, rats, rabbits, guinea pigs, pigs, micro-pigs, goats, dogs, cats, and non-human primates, e.g., baboons, monkeys, and chimpanzees can be used to generate variant A2M containing transgenic animals. Transgenic organisms desirably exhibit germline transfer of variant A2M nucleic acids and polypeptides described herein.

A variety of methodologies known in the art can be utilized to obtain any one of the isolated polypeptides or proteins of the present invention. At the simplest level, the amino acid sequence can be synthesized using commercially available peptide synthesizers. The synthetically constructed protein sequences, by virtue of sharing primary, secondary or tertiary structural and/or conformational characteristics with proteins can possess biological properties in common therewith, including protein activity. This technique can be particularly useful in producing small peptides and fragments of larger polypeptides. Fragments are useful, for example, in generating antibodies against the native polypeptide. Thus, they can be employed as biologically active or immunological substitutes for natural, purified proteins in screening of therapeutic compounds and in immunological processes for the development of antibodies. The polypeptides and proteins of the present invention can alternatively be purified from cells which have been altered to express the desired polypeptide or protein. As used herein, a cell can be said to be altered to express a desired polypeptide or protein when the cell, through genetic manipulation, can be made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells in a suitable culture medium, and purifying the protein from the cells or the culture in which the cells are grown. For example, the methods can include a process for producing a polypeptide in which a host cell containing a suitable expression vector that includes a polynucleotide of the invention can be cultured under conditions that allow expression of the encoded polypeptide. The polypeptide can be recovered from the culture, conveniently from the culture medium, or from a lysate prepared from the host cells and further purified. Preferred embodiments include those in which the protein produced by such process can be a full length or mature form of the protein, such as A2M. In an alternative method, the polypeptide or protein can be purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological or immunological activity include fragments comprising greater than about 100 amino acids, or greater than about 200 amino acids, and fragments that encode specific protein domains. The purified polypeptides can be used in in vitro binding assays which are well known in the art to identify molecules which bind to the polypeptides. These molecules include, but are not limited to, small molecules, molecules from combinatorial libraries, antibodies or other proteins. The molecules identified in a binding assay can then be tested for antagonist or agonist activity in in vivo tissue culture or animal models that are well known in the art. In brief, the molecules can be titrated into a plurality of cell cultures or animals and then tested for either cell or animal death or prolonged survival of the animal or cells.

The resulting expressed variant A2M polypeptides can then be purified from a culture, for example, from culture medium or cell extracts, using known purification processes, such as affinity chromatography, gel filtration, and ion exchange chromatography. The purification of the variant A2M polypeptides can also include an affinity column containing agents which will bind to the protein; one or more column steps over such affinity resins as concanavalin A-agarose, Heparin-Toyopearl™ or Cibacron blue 3GA Sepharose™; one or more steps involving hydrophobic interaction chromatography using such resins as phenyl ether, butyl ether, or propyl ether; or immunoaffinity chromatography. Alternatively, the protein of the invention can also be expressed in a form which will facilitate purification.

For example, a protein can be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.). Finally, one or more reverse-phase high performance liquid chromatography (RP-HPLC) steps employing hydrophobic RP-HPLC media, for example, silica gel having pendant methyl or other aliphatic groups, can be employed to further purify the protein. Any combination of the foregoing purification procedures can also be employed to provide a substantially homogeneous isolated or purified recombinant variant A2M polypeptide. The variant A2M polypeptides purified can be substantially free of other mammalian proteins and can be defined in accordance with the present invention as an "isolated protein."

Therapeutic Methods

Any method known in the art can be used to treat the chronic wound, or to treat the pathology that can be causing the chronic wound. A method can comprise treatment of a chronic wound in a mammal, such as a neuropathic ulcer decubitus ulcer, a venous ulcer or a diabetic ulcer or an infected wound. The method can comprise applying an A2M composition to the wound. A2M compositions and formulations can be used for inhibiting proteases. A2M compositions can be used to prevent, slow, or alter FAC formation. A variant A2M can be more efficient than a wild-type A2M polypeptide in inhibiting proteases, have a longer half-life, have a slower clearance factor, or any combination thereof.

In some embodiments, the wound is a decubital ulcer, a pressure ulcer, a lower extremity ulcer, a deep sternal wound, a post-operative wound, a refractory post-operative wound of the trunk area, a wound to the great saphenous vein following harvesting of the great saphenous vein, a venous ulcer, or an anal fissure. In those embodiments involving a lower extremity ulcer, the ulcer may be in a diabetic patient. In other embodiments, the wound is a venous ulcer, pressure ulcer, or post-operative ulcer.

The A2M composition can be comprised on a wound dressing. Dry and hydrated, i.e. wet wound dressings and delivery systems can be used and can also be suitable for active ingredients, their use for the treatment of wounds and skin diseases, preferably chronic wounds. A wound dressing can be applied to the chronic wound for a period of at least 1 hour, at least 24 hours, at least 48 hours, or at least 72 hours. The treatment may be extended for several days, weeks or months, with dressing changes as appropriate, if necessary for chronic wounds.

Another aspect of the invention relates to articles of manufacture comprising a composition of the invention and a dressing. In some embodiments, the dressing is a dry dressing, moisture-keeping barrier dressing, or bioactive dressing. In those embodiments involving a dry dressing, the dressing may be gauze, a bandage, a non-adhesive mesh, a membrane, foils, foam, or a tissue adhesive. In those embodiments involving a moisture-keeping barrier dressing, the dressing may be a paste, a cream, an ointment, a nonpermeable or semi-permeable membrane or foil, a hydrocolloid, a hydrogel, or combinations thereof. In those embodiments involving a bioactive dressing, the dressing may be an antimicrobial dressing. For example, the wound dressing may be a woven, nonwoven or knitted fabric having the A2M composition coated thereon, or it may be a bioresorbable polymer film or sponge having the A2M composition dispersed therein for sustained release at the ulcer site.

Once the site from which the pain can be originating can be identified by the presence of A2M, any method known in the art can be used to treat the pain, or to treat the pathology that can be causing the pain. For example, if radiculopathy or discogenic pain or facet pain has been diagnosed, any number of methods known in the art for treating spinal pain can be applied to treat the patient. Suitable methods include, but are not limited to, laminotomy, laminectomy, discectomy, microdiscectomy, percutaneous discectomy, endoscopic discectomy, laser discectomy, foramenotomy, fusion, prolotherapy, other surgical decompressions, decompression with fusion with or without instrumentation.

Pain in the spine can also be treated by standard non-surgical methods, including administration of steroidal or non-steroidal anti-inflammatory agents. Non-steroidal anti-inflammatory (NSAID) agents are well known in the art. Non-steroidal agents, including NSAIDs such as ibuprofen, aspirin or paracetamol can be used. Steroids, such as glucocorticoids, which reduce inflammation by binding to cortisol receptors, can also be used for treatment.

Any number of methods known in the art for treating joint-related pain can be applied to treat the patient. Suitable methods include surgical and non-surgical methods including, but not limited to, arthroscopic debridement or administration of steroidal or non-steroidal anti-inflammatory agents.

Any of the compositions described herein can be used for enhancing the nonspecific inhibition of one or more proteases in a human or non-human animal experiencing or susceptible to one or more conditions selected from the group of arthritis, inflammation, ligament injury, tendon injury, bone injury, cartilage degeneration, cartilage injury, an autoimmune disease, back pain, joint pain, joint degeneration, disc degeneration, spine degeneration, bone degeneration, or any combination thereof. A variant A2M polypeptide can be administered to an animal to reduce one or more protease activities in an animal.

A variant A2M polypeptide can be used for inhibiting proteases. A variant A2M polypeptide can be used for treatment of pain and inflammation conditions and diseases. A variant A2M polypeptide can be used to prevent, slow, or alter FAC formation. A variant A2M can be more efficient than a wild-type A2M polypeptide in inhibiting proteases, have a longer half-life, have a slower clearance factor, or any combination thereof.

A variant A2M polypeptide can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual), oral, intra-articular or inhalation routes of administration. A variant A2M polypeptide can also be administered using bioerodible inserts, bare-metal stents (BMS), or drug-eluting stents (DES or coated stents, or medicated stents), and can be delivered directly to spinal structures, such as intervertebral discs, the epidural space and facet joints, or to diarthroidal joints. A variant A2M polypeptide can be formulated in dosage forms appropriate for each route of administration. A variant A2M polypeptide can additionally be formulated for enteral administration.

A variant A2M polypeptide can be administered to a subject in a therapeutically effective amount. The precise dosage will vary according to a variety of factors such as subject dependent variables, such as age, the injury or pathology being treated, and the treatment being affected. The exact dosage can be chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

For some compositions, such a variant A2M polypeptide disclosed herein, as further studies are conducted information will emerge regarding appropriate dosage levels for treatment of various conditions in various subjects, and the ordinary skilled worker, considering the therapeutic context, age, and general health of the recipient, will be able to ascertain proper dosing. The selected dosage depends upon the route of administration, and on the duration of the treatment desired. Generally dosage levels can include 0.1 to 40 mg/kg of body weight daily. Generally, for local injection or infusion, dosages can be lower. Depending on the composition and site of administration, dosage levels can be between about 1 to 500,000 mg, in a volume between about 0.1 to 10 mL. For example, dosage levels can be between about 5 to 450 mg, 5 to 400 mg, 5 to 350 mg, 5 to 300 mg, 5 to 250 mg, 5 to 200 mg, 5 to 150 mg, 5 to 100 mg, 5 to 500 mg, 5 to 25 mg, 100 to 150 mg, 100 to 200 mg, 100 to 250 mg, 100 to 300 mg, 100 to 350 mg, 100 to 400 mg, 100 to 450 mg, or 100 to 500 mg in a volume between about 0.1 to 9 mL, 0.1 to 8 mL, 0.1 to 7 mL, 0.1 to 6 mL, 0.1 to 5 mL, 0.1 to 4 mL, 0.1 to 3 mL, 0.1 to 2 mL, 0.1 to 1 mL, 0.1 to 0.9 mL, 0.1 to 0.7 mL, 0.1 to 0.6 mL, 0.1 to 0.5 mL, 0.1 to 0.4 mL, 0.1 to 0.3 mL, 0.1 to 0.2 mL, 1 to 9 mL, 1 to 8 mL, 1 to 7 mL, 1 to 6 mL, 1 to 5 mL, 1 to 4 mL, 1 to 3 mL, or 1 to 2 mL. Normal dosage amounts of various variant A2M polypeptides or nucleic acids, or fragment thereof can vary from any number between approximately 1 to 500,000 micrograms, up to a total dose of about 50 grams, depending upon the route of administration. Desirable dosages include, for example, 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, 10 g, 20 g, 30 g, 40 g, and 50 g.

The dose of the variant A2M polypeptide, or fragment thereof, can be administered to produce a tissue or blood concentration or both from approximately any number between 0.1 µM to 500 mM. Desirable doses produce a tissue or blood concentration or both of about any number between 1 to 80004. Preferable doses produce a tissue or blood concentration of greater than about any number between 10 µM to about 500 µM. Preferable doses are, for example, the amount of active ingredient required to achieve a tissue or blood concentration, or both, of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 145 µM, 150 µM, 160 µM, 170 µM, 180 µM, 190 µM, 200 µM, 220 µM, 240 µM, 250 µM, 260 µM, 280 µM, 300 µM, 320

μM, 340 μM, 360 μM, 380 μM, 400 μM, 420 μM, 440 μM, 460 μM, 480 μM, and 500 μM. Although doses that produce a tissue concentration of greater than 800 μM are not preferred, they can be used with some embodiments of the invention. A constant infusion of the variant A2M polypeptide, or fragment thereof, can also be provided so as to maintain a stable concentration in the tissues as measured by blood levels.

A variant A2M polypeptide can be administered in an aqueous solution by parenteral, intradiscal, intrafacet, intrathecal, epidural or joint injection. A variant A2M polypeptide herein can be administered directly into the area of the spine or joint that can be the source of pain in the subject. For example, when fibronectin-aggrecan complexes are detected in the epidural space, a variant A2M polypeptide that inhibits proteases or that prevents FAC formation can be administered by direct injection into the epidural space. Alternatively, variant A2M polypeptide that inhibits proteases or that prevents FAC formation can be administered by direct injection into the disc space, facet joint, or diarthroidial joint when fibronectin-aggrecan complexes are detected in these spaces. In some embodiments, aggrecan can include any naturally-occurring variants and splice variants of aggrecan, versican, brevican and neurocan, and any variants of aggrecan, versican, brevican and neurocan due to splicing by different cell types. In some embodiments, fibronectin can include any naturally occurring fibronectin variants including approximately 20 known splice variants associated with a disease or a disorder and fibronectin variants due to different splicing by different cell types.

A composition or formulation or agent can also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations can be lyophilized and redissolved or resuspended immediately before use. The formulation can be sterilized by, for example, filtration through a bacteria retaining filter, by incorporating sterilizing agents into the compositions, by irradiating the compositions, or by heating the compositions.

A variant A2M polypeptide can also be administered in controlled release formulations. Controlled release polymeric devices can be made for long term release systemically following implantation of a polymeric device (rod, cylinder, film, or disc) or injection (microparticles). The matrix can be in the form of microparticles such as microspheres, where peptides are dispersed within a solid polymeric matrix or microcapsules, where the core can be of a different material than the polymeric shell, and the peptide can be dispersed or suspended in the core, which can be liquid or solid in nature. Unless specifically defined herein, microparticles, microspheres, and microcapsules are used interchangeably. Alternatively, the polymer can be cast as a thin slab or film, ranging from nanometers to four centimeters, a powder produced by grinding or other standard techniques, or even a gel such as a hydrogel.

Either non-biodegradable or biodegradable matrices can be used for delivery of any composition described herein, although biodegradable matrices are preferred. These can be natural or synthetic polymers, although synthetic polymers are preferred due to the better characterization of degradation and release profiles. The polymer can be selected based on the period over which release can be desired. In some cases linear release can be most useful, although in others a pulse release or "bulk release" can provide more effective results. The polymer can be in the form of a hydro gel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection which will typically deliver a dosage that can be much less than the dosage for treatment of an entire body or systemic delivery. These can be implanted or injected subcutaneously, into the muscle, fat, or swallowed.

A variant A2M polypeptide can be used in the treatment of a condition or a disease, such as a chronic wound. For example, a condition or disease can be tendon condition, ligament condition, joint injury, spine injury, or inflammation, Alzheimer's disease, cerebral amyloid angiopathy, multiple sclerosis, congenital anti-thrombin deficiency, rheumatoid arthritis, growth of various tumors, coronary or limb ischemia, retinopathies, and regulation of immune response to tumors and viral infections. Others include Acne vulgaris, Alzheimer's disease, arthritis, asthma, acne, allergies and sensitivities, Autoimmune diseases, atherosclerosis, bronchitis, cancer, carditis, Crohn's disease, colitis, chronic pain, cirrhosis, Celiac disease, Chronic prostatitis, dermatitis diverticulitis, dementia, dermatitis, diabetes, dry eyes, edema, emphysema, eczema, fibromyalgia, gastroenteritis, gingivitis, Glomerulonephritis, Hypersensitivities, hepatitislupus erythematous, acid reflux/heartburn, heart disease, hepatitis, high blood pressure, insulin resistance, Interstitial cystitis, Inflammatory bowel diseases, irritable bowel syndrome (IBS), joint pain/arthritis/rheumatoid arthritis, metabolic syndrome (syndrome X), myositis, nephritis, obesity, osteopenia, osteoporosis, Pelvic inflammatory disease, Parkinson's disease, periodontal disease, polyarteritis, polychondritis, psoriasis, Reperfusion injury, Rheumatoid arthritis, Sarcoidosis, scleroderma, sinusitis, Sjögren's syndrome, spastic colon, systemic candidiasis, tendonitis, Transplant rejection, ulcerative colitcis, UTI's, Vasculitis, and vaginitis.

In some embodiments, a variant A2M polypeptide, can be used in the treatment of cancer. For example, variant A2M polypeptides can be administered directly into a tumor, such as a solid tumor, by injection or another suitable means.

An autoimmune disease can be a disease or disorder arising from and directed against an individual's own tissues or organs or a co-segregate or manifestation thereof or resulting condition therefrom. In many of these autoimmune and inflammatory disorders, a number of clinical and laboratory markers can exist, including, but not limited to, hypergammaglobulinemia, high levels of auto-antibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B-cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis.

Each of these pathways can participate to different degrees in the pathology of autoimmune diseases. "Autoimmune disease" can be an organ-specific disease (i.e., the immune response can be specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, SLE, RA, polymyositis, etc.). Preferred such diseases include autoimmune rheumatologic disorders (such as, for example, RA, Sjogren's syndrome, scleroderma, lupus such as SLE and lupus nephritis, polymyositis, dermatomyositis, cryoglobulinemia, antiphospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis be (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, MS, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, posttransfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, MS, Sjogren's syndrome, Graves' disease, IDDM, pernicious anemia, thyroiditis, and glomerulonephritis.

A variant A2M polypeptide can be suitable for delivery into one or more joints or into the spine. One or more joints can be one or more synovial, diarthrodial, amphiarthrodial, synarthrodial, symphyseal, or cartilaginous joints. A joint can be a wrist, spinal, vertebral, cervical, shoulder, elbow, carpal, metacarpal, phalangeal, acromioclavicular, sternoclavicular, scapular, costal, sacroiliac, hip, knee, ankle tarsal, articulations of a foot or hand, axillary articulations, or a metatarsal.

A joint can refer to any diarthoidal (also called synovial) joints. A joint can be any joint containing bone, articular cartilage, a joint capsule, a synovial tissue lining, or lubricating synovial fluid inside a joint capsule. Cartilage components of a joint can be a chondral component. A component of the knee can be a meniscal component. In some embodiments, a synovial joint can be a shoulder or wrist or ankle or hip or elbow, or the small joints of the fingers or toes. A joint can be a normal joint or a control joint. A normal or control joint can be a joint that can be an insignificant source of pain to a subject. The level of pain that can be present in a normal joint typically may not impact the function or quality of the patient's life to the degree that the patient seeks medical care. A joint sample or sample from a joint can be a sample of tissue or fluid from a joint including, but not limited to, ex vivo and in vivo synovial fluid samples and joint or tissue lavages. A joint sample or sample from a joint can be a biological sample.

A variant A2M polypeptide can be used in the treatment of pain, such as pain associated with a condition or a disease of the current disclosure.

Pain can be radicular pain, radiculopathy, radiculopathic pain and sciatica and can be radiating pain of the extremities which emanates from the spinal root level or "radic" along the path of one or more irritated lumbar nerve roots. In the case of sciatica, this can originate from the L4, L5 and/or L6 or transitional vertebrae if present and/or sacroiliac spinal nerve roots, which make up the sciatic nerve. Radiating pain can be also possible from the high lumbar disc herniations in the l3, l2 or l1 regions or from any cervical nerve root in the case of a cervical disc herniation, cervical nerve root irritation or cervical disc degeneration. This pain can differ from pain resulting from a facet joint or other spinal structure, which can be classified as "referred" pain. Radiating pain can be also possible from the high lumbar disc herniations in the L3, L2 or L1 regions or cervical spine regions.

Pain can be discogenic pain and can be spinal related pain that generates from an intervertebral disc. The intervertebral disc suffers from reduced functionality in association with a loss of hydration from the nucleus pulposus. The reduction in functionality coincides with damage in the annulus fibrosus. This weakening can lead to anatomic lesions such as bulging, prolapsed, extruded, or sequestered disc. This weakening can also lead to possible biochemical lesions resulting from leakage of the disc contents that can manifest in back pain or aforementioned chemical radiculopathy.

Pain can be facet joint pain or facetogenic pain and can be pain generating from a facet joint, facet joints, or zygapophysial joints that are paired, true synovial joints endowed with cartilage, capsule, meniscoid, and synovial membrane. Spinal-pain or spine related pain includes, but is not limited to, discogenic, facetogenic and radiculopathic pain.

Pain can be acute pain and can be pain lasting up to six months, e.g., five months, four months, three months, two months, four weeks, three weeks, two weeks, one week, six days, five days, four days, three days, two days or one day or less. Chronic pain can be pain of duration longer than six months.

Any subject described herein can be treated with any of the compositions described herein. In some embodiments, a subject can be diagnosed with a condition or disease before or after being diagnosed with a condition or disease, such as by the methods described in U.S. Pat. No. 7,709,215 and U.S. Publication No.: US 2010/0098684A1. In some embodiments, a subject can be treated with any composition described herein, before or after being diagnosed with a condition or disease.

Subjects

Subjects can include any subject that presents with pain in the spine or joint. In some embodiments, a subject can be selected for the detection of A2M. Preferably the subject can be human. Subjects can be experiencing any pain, such as pain associated with the spine, including, but not limited to, discogenic, facetogenic or radiculopathic pain.

Subjects can be suspected of experiencing pain associated with any anatomic structure of a joint including, but not limited to, bone, articular cartilage, or the synovial tissue lining. Joints can include, but are not limited to, large diarthrodial (synovial) joints (e.g. knee, hip, shoulder), small diarthrodial (synovial) joints (e.g. elbow, wrist, ankle, zygoapophyseal or facet joints of spine), and amphiarthrodial joints (e.g. sacroiliac joint, sternoclavicular joint, tempomandibular joint ("TMJ")). Subjects can be experiencing acute joint-related pain, or can suffer from chronic joint-related pain. These can be related to degenerative disease (e.g. osteoarthritis), myofascial pain syndromes, inflammatory or crystalline arthritides, or other enthesopathies, tendon/ligament injuries or degeneration, or soft tissue pathology outside the musculoskeletal system.

In some embodiments, a subject may have been experiencing joint-related or spine-related pain for 30 or 25 weeks or less. In some embodiments, a subject may have been experiencing joint-related or spine-related pain for 20, 15, 10, 8, or 6 weeks, or less. Subjects can be of either sex and can be of any age. Subjects may be experiencing acute or chronic pain.

A subject can be human or non-human animal. For example, the animal can be a mammal, such as a mouse, rat, rabbit, cat, dog, monkey, horse or goat. A subject can be a virus, bacterium, *mycoplasma*, parasite, fungus, or plant, or animal, such as a mammal, for example, a human.

In some embodiments, a subject can be diagnosed as needing treatment with any of the compositions described herein. For example, a subject can be diagnosed as needing treatment with an A2M enriched sample or an agent that can prevent FAC formation.

Samples

Any of the compositions described herein can be derived from a biological sample. Biological samples can also include sections of tissues such as biopsy samples, frozen sections taken for histologic purposes, and lavage samples. A biological sample can be from a virus, bacterium, mycoplasma, parasite, fungus, or plant. A biological sample can be from an animal, such as a mammal, for example, a human, non-human primate, rodent, caprine, bovine, ovine, equine, canine, feline, mouse, rat, rabbit, horse or goat.

A biological sample can be a tissue sample or bodily fluid, such as a human bodily fluid. For example, the bodily fluid can be blood, sera, plasma, lavage, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocyl cavity fluid, or umbilical cord blood. One or more of the biological sample(s) can comprise a cell, such as a stem cell, undifferentiated cell, differentiated cell, or cell from a diseased subject or subject with a specific condition. A biological sample can be blood, a cell, a population of cells, a quantity of tissue, fluid, or lavasate from a joint of a subject. A biological sample can comprise cells from cartilaginous tissue or can be free of cells. A biological sample can be substantially depleted of a common serum protein, such as, but not limited to, albumin or IgG. Depletion can comprise filtration, fractionation, or affinity purification.

Biological samples can be collected by any non-invasive means, such as, for example, by drawing blood from a subject, or using fine needle aspiration or needle biopsy. Alternatively, biological samples can be collected by an invasive method, including, for example, surgical biopsy.

A biological sample can comprise disease or condition specific proteins. A biological sample can be from a subject with a disease or condition or from a subject without a disease or condition. In some embodiments, a biological sample can be from a subject diagnosed with a disease or condition or from a subject not diagnosed with or without a disease or condition. A diagnosis can be made by any of the methods described herein. A biological sample can be from a subject at one time point and another biological sample can be from a subject at a later or earlier time point, wherein the subject can be the same or a different subject. For example, the subject may have a disease or condition or have been diagnosed with a disease or condition, and samples can be taken as the disease or condition progresses. A biological sample can be from a subject pretreatment and another biological sample can be from a subject at post treatment, wherein the subject can be the same or different subject. A biological sample can be from a subject non-responsive to treatment and another biological sample can be from a subject responsive to a treatment. Biological samples can be from the same or different species. One or more biological samples can be from the same subject or from a different subject from which one or more other biological samples were obtained.

A spine sample or sample from the spine can be a sample of tissue or fluid from the spine or added to the spine (lavage) including, but not limited to, spinal disc samples, epidural samples, and facet joint samples. A spine sample or sample from the spine can be a biological sample. Any number of methods known in the art can be used to retrieve sample from the spine for the detection of inflammation biomarkers. These methods include, but are not limited to, methods for obtaining samples from the epidural space, the intervertebral disc space and the facet joint space. Any number of methods known in the art can be used to obtain joint samples for the detection of inflammation biomarkers. Suitable methods include, but are not limited to, percutaneous or open aspiration, biopsy, or lavage.

The methods of the invention can be applied to the study of any type of biological samples allowing one or more biomarkers to be assayed. A biological sample can be a fresh or frozen sample collected from a subject, or archival samples with known diagnosis, treatment and/or outcome history.

The inventive methods can be performed on the biological sample itself without or with limited processing of the sample. The inventive methods can be performed at the single cell level (e.g., isolation of cells from the biological sample). Multiple biological samples can be taken from the same tissue/body part in order to obtain a representative sampling of the tissue.

Any of the method described herein can be performed on a protein extract prepared from the biological sample. The methods can also be performed on extracts containing one or more of: membrane proteins, nuclear proteins, and cytosolic proteins. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). After the protein extract has been obtained, the protein concentration of the extract can be standardized to a value being the same as that of the control sample in order to allow signals of the protein markers to be quantitated. Such standardization can be made using photometric or spectrometric methods or gel electrophoresis.

Any of the method described herein can be performed on nucleic acid molecules extracted from the biological sample. For example, RNA can be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA can then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

After extraction, mRNA can be amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions can be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

OTHER EMBODIMENTS

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-911910-18-2); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998), which are all incorporated by reference herein in their entireties.

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art can recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described as these can vary. It is also to be understood that the terminology used herein is for the purpose of describing particular embodiments only, and is not intended to limit the scope of the present disclosure which can be limited only by the appended claims.

Unless defined otherwise, all technical and scientific terms used herein have the meanings that would be commonly understood by one of skill in the art in the context of the present specification.

It should be noted that as used herein and in the appended claims, the singular forms "a," "an," and "the" include plural reference unless the context clearly dictates otherwise. Thus, for example, reference to "a nucleotide" includes a plurality of such nucleotides; reference to "the nucleotide" is a reference to one or more nucleotides and equivalents thereof known to those skilled in the art, and so forth.

The term "and/or" shall in the present context be understood to indicate that either or both of the items connected by it are involved. While preferred embodiments of the present disclosure have been shown and described herein, it can be obvious to those skilled in the art that such embodiments are provided by way of example only. Numerous variations, changes, and substitutions can now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Sequences:

SEQ ID NO 1: Wild-type A2M precursor protein-complete vector DNA sequence including tag sequences for easier purification.

```
   1   CTCATGACCA AAATCCCTTA ACGTGAGTTA CGCGCGCGTC GTTCCACTGA GCGTCAGACC
  61   CCGTAGAAAA GATCAAAGGA TCTTCTTGAG ATCCTTTTTT TCTGCGCGTA ATCTGCTGCT
 121   TGCAAACAAA AAAACCACCG CTACCAGCGG TGGTTTGTTT GCCGGATCAA GAGCTACCAA
 181   CTCTTTTTCC GAAGGTAACT GGCTTCAGCA GAGCGCAGAT ACCAAATACT GTTCTTCTAG
 241   TGTAGCCGTA GTTAGCCCAC CACTTCAAGA ACTCTGTAGC ACCGCCTACA TACCTCGCTC
 301   TGCTAATCCT GTTACCAGTG GCTGCTGCCA GTGGCGATAA GTCGTGTCTT ACCGGGTTGG
 361   ACTCAAGACG ATAGTTACCG GATAAGGCGC AGCGGTCGGG CTGAACGGGG GGTTCGTGCA
 421   CACAGCCCAG CTTGGAGCGA ACGACCTACA CCGAACTGAG ATACCTACAG CGTGAGCTAT
 481   GAGAAAGCGC CACGCTTCCC GAAGGGAGAA AGGCGGACAG GTATCCGGTA AGCGGCAGGG
 541   TCGGAACAGG AGAGCGCACG AGGGAGCTTC CAGGGGGAAA CGCCTGGTAT CTTTATAGTC
 601   CTGTCGGGTT TCGCCACCTC TGACTTGAGC GTCGATTTTT GTGATGCTCG TCAGGGGGGC
 661   GGAGCCTATG GAAAAACGCC AGCAACGCGG CCTTTTTACG GTTCCTGGCC TTTTGCTGGC
 721   CTTTTGCTCA CATGTTCTTT CCTGCGTTAT CCCCTGATTC TGTGGATAAC CGTATTACCG
 781   CCTTTGAGTG AGCTGATACC GCTCGCCGCA GCCGAACGAC CGAGCGCAGC GAGTCAGTGA
 841   GCGAGGAAGC GGAAGGCGAG AGTAGGGAAC TGCCAGGCAT CAAACTAAGC AGAAGGCCCC
 901   TGACGGATGG CCTTTTTGCG TTTCTACAAA CTCTTTCTGT GTTGTAAAAC GACGGCCAGT
 961   CTTAAGCTCG GGCCCCCTGG GCGGTTCTGA TAACGAGTAA TCGTTAATCC GCAAATAACG
1021   TAAAAACCCG CTTCGGCGGG TTTTTTTATG GGGGGAGTTT AGGGAAAGAG CATTTGTCAG
1081   AATATTTAAG GGCGCCTGTC ACTTTGCTTG ATATATGAGA ATTATTTAAC CTTATAAATG
1141   AGAAAAAAGC AACGCACTTT AAATAAGATA CGTTGCTTTT TCGATTGATG AACACCTATA
1201   ATTAAACTAT TCATCTATTA TTTATGATTT TTTGTATATA CAATATTTCT AGTTTGTTAA
1261   AGAGAATTAA GAAAATAAAT CTCGAAAATA ATAAAGGGAA AATCAGTTTT TGATATCAAA
1321   ATTATACATG TCAACGATAA TACAAAATAT AATACAAACT ATAAGATGTT ATCAGTATTT
```

-continued

Sequences:

```
1381  ATTATCATTT AGAATAAATT TTGTGTCGCC CTTAATTGTG AGCGGATAAC AATTACGAGC
1441  TTCATGCACA GTGGCGTTGA CATTGATTAT TGACTAGTTA TTAATAGTAA TCAATTACGG
1501  GGTCATTAGT TCATAGCCCA TATATGGAGT TCCGCGTTAC ATAACTTACG GTAAATGGCC
1561  CGCCTGGCTG ACCGCCCAAC GACCCCCGCC CATTGACGTC AATAATGACG TATGTTCCCA
1621  TAGTAACGCC AATAGGGACT TTCCATTGAC GTCAATGGGT GGAGTATTTA CGGTAAACTG
1681  CCCACTTGGC AGTACATCAA GTGTATCATA TGCCAAGTAC GCCCCCTATT GACGTCAATG
1741  ACGGTAAATG GCCCGCCTGG CATTATGCCC AGTACATGAC CTTATGGGAC TTTCCTACTT
1801  GGCAGTACAT CTACGTATTA GTCATCGCTA TTACCATGGT GATGCGGTTT TGGCAGTACA
1861  TCAATGGGCG TGGATAGCGG TTTGACTCAC GGGGATTTCC AAGTCTCCAC CCCATTGACG
1921  TCAATGGGAG TTTGTTTTGG CACCAAAATC AACGGGACTT TCCAAAATGT CGTAACAACT
1981  CCGCCCCATT GACGCAAATG GGCGGTAGGC GTGTACGGTG GGAGGTCTAT ATAAGCAGAG
2041  CTCTCTGGCT AACTAGAGAA CCCACTGCTT ACTGGCTTAT CGAAATTAAT ACGACTCACT
2101  ATAGGGGTAC CTGCCACCAT GGGGAAAAAC AAACTGCTGC ATCCAAGCCT GGTCCTGCTG
2161  CTGCTGGTTC TGCTGCCTAC TGACGCCTCT GTGAGCGGAA AGCCCCAGTA TATGGTTCTG
2221  GTCCCGTCCC TGCTGCACAC CGAGACCACA GAAAAGGGT GCGTGCTGCT GTCTTACCTG
2281  AATGAAACAG TGACTGTTAG TGCCTCACTG GAGAGTGTGC GCGGAAATCG TTCACTGTTC
2341  ACCGATCTGG AGGCGGAAAA CGATGTGCTG CATTGCGTCG CATTTGCTGT GCCAAAAGC
2401  TCCTCTAATG AAGAAGTGAT GTTCCTGACC GTCCAGGTGA AGGGCCCTAC ACAGGAATTC
2461  AAAAAACGCA CTACCGTTAT GGTCAAAAAC GAGGATAGCC TGGTGTTTGT TCAGACAGAC
2521  AAATCCATCT ATAAGCCTGG TCAGACTGTG AAGTTCCGGG TGGTTAGCAT GGATGAAAAT
2581  TTTCACCCCC TGAACGAGCT GATTCCACTG GTGTACATCC AGGACCCTAA AGGCAACCGC
2641  ATCGCCCAGT GGCAGTCTTT CCAGCTGGAA GGCGGTCTGA AGCAGTTTAG TTTCCCTCTG
2701  AGTTCAGAGC CGTTTCAGGG TTCTTATAAA GTCGTGGTTC AGAAAAAGAG TGGGGGACGT
2761  ACTGAACATC CTTTTACCGT TGAAGAGTTC GTCCTGCCGA AATTTGAGGT CCAGGTGACC
2821  GTTCCCAAGA TTATCACAAT TCTGGAAGAG GAAATGAACG TGAGCGTGTG CGGACTGTAT
2881  ACCTACGGCA AACCAGTGCC TGGTCACGTT ACAGTCAGTA TCTGCCGTAA GTACTCAGAT
2941  GCAAGCGACT GTCATGGCGA AGATTCACAG GCTTTTTGCG AGAAGTTCAG CGGCCAGCTG
3001  AACTCCCACG GTTGCTTCTA TCAGCAGGTG AAAACCAAGG TTTTTCAGCT GAAACGGAAG
3061  GAGTACGAAA TGAAACTGCA TACAGAAGCC CAGATTCAGG AAGAAGGCAC CGTCGTGGAA
3121  CTGACTGGTC GTCAGAGCTC CGAGATTACC CGGACAATCA CTAAACTGAG CTTCGTGAAG
3181  GTTGATTCCC ACTTTCGGCA GGGGATTCCC TTTTTCGGAC AGGTGCGCCT GGTTGACGGG
3241  AAAGGAGTTC CGATCCCCAA CAAAGTGATC TTTATTCGCG GCAATGAAGC CAACTATTAC
3301  AGCAACGCGA CAACTGATGA GCATGGGCTG GTGCAGTTCA GTATCAATAC CACAAACGTG
3361  ATGGGAACCT CACTGACAGT CCGCGTGAAT TATAAAGACC GTTCACCGTG TTATGGCTAC
3421  CAGTGGGTGA GCGAGGAACA CGAGGAAGCC CACCATACCG CGTACCTGGT TTTCAGCCCC
3481  TCCAAATCTT TTGTCCATCT GGAACCTATG TCTCACGAGC TGCCGTGCGG CCATACCCAG
3541  ACAGTGCAGG CACATTATAT TCTGAACGGC GGCACCCTGC TGGGTCTGAA AAAGCTGAGC
3601  TTTTATTACC TGATTATGGC TAAGGGGGGA ATCGTCCGCA CTGGCACCCA CGGTCTGCTG
3661  GTTAAACAGG AAGATATGAA GGGCCATTTC AGTATTTCAA TCCCTGTTAA AAGCGACATT
```

-continued

```
3721   GCTCCGGTCG CCCGTCTGCT GATCTATGCC GTGCTGCCAA CCGGCGATGT TATCGGTGAC
3781   TCCGCCAAAT ACGATGTGGA GAATTGTCTG GCGAACAAGG TTGACCTGAG CTTTTCCCCC
3841   TCTCAGAGTC TGCCAGCGTC TCATGCACAT CTGCGTGTGA CCGCAGCCCC TCAGAGCGTT
3901   TGCGCTCTGC GTGCAGTGGA TCAGTCCGTG CTGCTGATGA AGCCAGACGC AGAACTGTCT
3961   GCTAGCAGCG TGTATAATCT GCTGCCTGAG AAAGATCTGA CCGGGTTCCC AGGACCTCTG
4021   AACGATCAGG ATGACGAAGA CTGTATTAAT CGCCACAACG TGTATATTAA TGGGATCACA
4081   TACACTCCGG TTTCAAGCAC CAACGAAAAA GATATGTACA GCTTCCTGGA GGACATGGGT
4141   CTGAAAGCGT TTACCAATTC CAAGATCCGG AAACCCAAGA TGTGCCCACA GCTGCAGCAG
4201   TATGAAATGC ACGGACCTGA GGGTCTGCGT GTGGGCTTTT ACGAATCTGA TGTGATGGGA
4261   CGTGGTCATG CACGTCTGGT TCATGTCGAG GAACCACACA CCGAAACAGT GCGTAAATAC
4321   TTCCCTGAGA CCTGGATTTG GACCTGGTT GTGGTGAACT CCGCGGGTGT GGCAGAAGTG
4381   GGTGTTACCG TCCCGGATAC TATTACCGAA TGGAAAGCAG GTGCCTTCTG TCTGTCTGAG
4441   GATGCAGGGC TGGGAATCTC CTCTACAGCC TCTCTGCGCG CGTTTCAGCC CTTTTTCGTC
4501   GAACTGACTA TGCCATATAG CGTGATTCGT GGCGAGGCAT TCACTCTGAA AGCTACCGTG
4561   CTGAATTACC TGCCCAAGTG CATCCGCGTG AGCGTGCAGC TGGAAGCTAG TCCCGCCTTT
4621   CTGGCGGTCC CAGTGGAGAA GGAACAGGCA CCGCACTGCA TTTGTGCTAA CGGCCGGCAG
4681   ACTGTTTCCT GGGCCGTCAC CCCCAAATCT CTGGGTAATG TGAACTTCAC CGTTTCAGCA
4741   GAGGCTCTGG AAAGCCAGGA GCTGTGCGGC ACCGAAGTCC CATCCGTGCC TGAGCATGGT
4801   CGCAAAGATA CAGTCATCAA GCCTCTGCTG GTTGAACCGG AAGGCCTGGA GAAGGAAACT
4861   ACCTTTAATT CTCTGCTGTG CCCAAGTGGC GGTGAAGTGT CCGAGGAACT GTCTCTGAAA
4921   CTGCCGCCCA ACGTGGTCGA GGAATCTGCC CGTGCGTCAG TTAGCGTCCT GGGGGATATT
4981   CTGGGAAGTG CCATGCAGAA TACCCAGAAC CTGCTGCAGA TGCCGTATGG CTGTGGCGAG
5041   CAGAATATGG TTCTGTTTGC GCCCAACATC TATGTCCTGG ATTACCTGAA TGAAACACAG
5101   CAGCTGACTC CTGAAATCAA AAGCAAGGCA ATCGGGTATC TGAATACCGG ATACCAGCGG
5161   CAGCTGAACT ATAAGCACTA CGACGGCTCC TATTCTACCT TCGGCGAACG GTACGGTCGC
5221   AATCAGGGGA ACACTTGGCT GACCGCCTTT GTGCTGAAAA CCTTTGCCCA GGCTCGCGCC
5281   TATATCTTTA TTGATGAGGC CCATATTACA CAGGCGCTGA TCTGGCTGTC ACAGCGCCAG
5341   AAGGACAACG GGTGTTTCCG TAGTTCAGGA AGCCTGCTGA ACAATGCCAT CAAAGGCGGC
5401   GTCGAGGATG AAGTGACACT GAGCGCATAC ATTACTATCG CTCTGCTGGA AATCCCTCTG
5461   ACAGTGACTC ACCCGGTGGT TCGCAATGCT CTGTTTTGCC TGGAAAGTGC ATGGAAAACA
5521   GCTCAGGAAG GCGATCACGG ATCACACGTG TATACTAAGG CACTGCTGGC GTACGCATTC
5581   GCTCTGGCCG GCAACCAGGA TAAACGTAAA GAAGTGCTGA ATCACTGAA TGAGGAAGCA
5641   GTTAAAAAGG ACAACAGCGT CCACTGGGAA CGGCCGCAGA AACCCAAGGC TCCAGTGGGT
5701   CACTTTTATG AGCCTCAGGC ACCGAGTGCT GAGGTGGAAA TGACCTCATA TGTTCTGCTG
5761   GCATACCTGA CCGCACAGCC TGCCCCCACA TCAGAAGATC TGACAAGCGC CACTAATATT
5821   GTGAAATGGA TCACCAAGCA GCAGAACGCG CAGGGCGGTT TTAGCTCCAC CCAGGACACA
5881   GTCGTGGCAC TGCACGCTCT GTCTAAATAT GGGGCAGCTA CCTTCACACG CACTGGAAAG
5941   GCCGCGCAAG TGACTATTCA GTCTAGTGGC ACCTTTTCAA GCAAGTTCCA GGTGGATAAC
6001   AATAACCGTC TGCTGCTGCA GCAGGTGTCC CTGCCCGAAC TGCCAGGCGA GTACTCTATG
```

-continued

| | Sequences: |
|---|---|
| 6061 | AAAGTCACTG GGGAAGGATG CGTGTATCTG CAGACCTCCC TGAAATACAA TATTCTGCCC |
| 6121 | GAGAAAGAAG AATTTCCATT CGCACTGGGC GTGCAGACCC TGCCTCAGAC ATGCGATGAA |
| 6181 | CCGAAGGCTC ATACTTCTTT TCAGATCAGT CTGTCAGTGA GCTATACCGG GTCCCGCTCT |
| 6241 | GCCAGTAACA TGGCGATTGT GGATGTGAAA ATGGTGAGTG GATTCATCCC TCTGAAACCG |
| 6301 | ACTGTGAAGA TGCTGGAACG GAGTAATCAC GTTTCACGCA CCGAGGTCTC CTCTAACCAT |
| 6361 | GTGCTGATCT ACCTGGATAA AGTGTCCAAT CAGACACTGT CTCTGTTTTT CACTGTGCTG |
| 6421 | CAGGATGTCC CCGTGCGTGA CCTGAAACCA GCCATTGTTA AGGTCTATGA TTATTACGAA |
| 6481 | ACCGACGAGT TCGCGATCGC AGAATACAAC GCGCCGTGCA GCAAAGACCT GGGGAATGCT |
| 6541 | GACTACAAGG ACGACGACGA CAAGGGGGCA AGCCACCACC ATCACCATCA CTAAGGATCC |
| 6601 | AAAATCAGCC TCGACTGTGC CTTCTAGTTG CCAGCCATCT GTTGTTTGCC CCTCCCCCGT |
| 6661 | GCCTTCCTTG ACCCTGGAAG GTGCCACTCC CACTGTCCTT TCCTAATAAA ATGAGGAAAT |
| 6721 | TGCATCACAA CACTCAACCC TATCTCGGTC TATTCTTTTG ATTTATAAGG GATTTTGCCG |
| 6781 | ATTTCGGCCT ATTGGTTAAA AAATGAGCTG ATTTAACAAA AATTTAACGC GAATTAATTC |
| 6841 | TGTGGAATGT GTGTCAGTTA GGGTGTGGAA AGTCCCCAGG CTCCCCAGCA GGCAGAAGTA |
| 6901 | TGCAAAGCAT GCATCTCAAT TAGTCAGCAA CCAGGTGTGG AAAGTCCCCA GGCTCCCCAG |
| 6961 | CAGGCAGAAG TATGCAAAGC ATGCATCTCA ATTAGTCAGC AACCATAGTC CCGCCCCTAA |
| 7021 | CTCCGCCCAT CCCGCCCCTA ACTCCGCCCA GTTCCGCCCA TTCTCCGCCC CATGGCTGAC |
| 7081 | TAATTTTTTT TATTTATGCA GAGGCCGAGG CCGCCTCTGC CTCTGAGCTA TTCCAGAAGT |
| 7141 | AGTGAGGAGG CTTTTTTGGA GGCCTAGGCT TTTGCAAAAA GCTCCCGGGA GCTTGTATAT |
| 7201 | CCATTTTCGG ATCTGATCAG CACGTGTTGA CAATTAATCA TCGGCATAGT ATATCGGCAT |
| 7261 | AGTATAATAC GACAAGGTGA GGAACTAAAC CATGGCCAAG CCTTTGTCTC AAGAAGAATC |
| 7321 | CACCCTCATT GAAAGAGCAA CGGCTACAAT CAACAGCATC CCCATCTCTG AAGACTACAG |
| 7381 | CGTCGCCAGC GCAGCTCTCT CTAGCGACGG CCGCATCTTC ACTGGTGTCA ATGTATATCA |
| 7441 | TTTTACTGGG GGACCTTGTG CAGAACTCGT GGTGCTGGGC ACTGCTGCTG CTGCGGCAGC |
| 7501 | TGGCAACCTG ACTTGTATCG TCGCGATCGG AAATGAGAAC AGGGGCATCT TGAGCCCCTG |
| 7561 | CGGACGGTGC CGACAGGTGC TTCTCGATCT GCATCCTGGG ATCAAAGCCA TAGTGAAGGA |
| 7621 | CAGTGATGGA CAGCCGACGG CAGTTGGGAT TCGTGAATTG CTGCCCTCTG GTTATGTGTG |
| 7681 | GGAGGGCTAA CACGTGCTAC GAGATTTCGA TTCCACCGCC GCCTTCTATG AAAGGTTGGG |
| 7741 | CTTCGGAATC GTTTTCCGGG ACGCCGGCTG GATGATCCTC CAGCGCGGGG ATCTCATGCT |
| 7801 | GGAGTTCTTC GCCCACCCCA ACTTGTTTAT TGCAGCTTAT AATGGTTACA AATAAAGCAA |
| 7861 | TAGCATCACA AATTTCACAA ATAAAGCATT TTTTTCACTG CATTCTAGTT GTGGTTTGTC |
| 7921 | CAAACTCATC AATGTATCTT ATCATGTCTG TATACCGTCG ACCTCTAGCT AGAGCTTGGC |
| 7981 | GTAATCATGG TCATTACCAA TGCTTAATCA GTGAGGCACC TATCTCAGCG ATCTGTCTAT |
| 8041 | TTCGTTCATC CATAGTTGCC TGACTCCCCG TCGTGTAGAT AACTACGATA CGGGAGGGCT |
| 8101 | TACCATCTGG CCCCAGCGCT GCGATGATAC CGCGAGAACC ACGCTCACCG GCTCCGGATT |
| 8161 | TATCAGCAAT AAACCAGCCA GCCGGAAGGG CCGAGCGCAG AAGTGGTCCT GCAACTTTAT |
| 8221 | CCGCCTCCAT CCAGTCTATT AATTGTTGCC GGGAAGCTAG AGTAAGTAGT TCGCCAGTTA |
| 8281 | ATAGTTTGCG CAACGTTGTT GCCATCGCTA CAGGCATCGT GGTGTCACGC TCGTCGTTTG |
| 8341 | GTATGGCTTC ATTCAGCTCC GGTTCCCAAC GATCAAGGCG AGTTACATGA TCCCCCATGT |

| | |
|---|---|
| 8401 | TGTGCAAAAA AGCGGTTAGC TCCTTCGGTC CTCCGATCGT TGTCAGAAGT AAGTTGGCCG |
| 8461 | CAGTGTTATC ACTCATGGTT ATGGCAGCAC TGCATAATTC TCTTACTGTC ATGCCATCCG |
| 8521 | TAAGATGCTT TTCTGTGACT GGTGAGTACT CAACCAAGTC ATTCTGAGAA TAGTGTATGC |
| 8581 | GGCGACCGAG TTGCTCTTGC CCGGCGTCAA TACGGGATAA TACCGCGCCA CATAGCAGAA |
| 8641 | CTTTAAAAGT GCTCATCATT GGAAAACGTT CTTCGGGGCG AAAACTCTCA AGGATCTTAC |
| 8701 | CGCTGTTGAG ATCCAGTTCG ATGTAACCCA CTCGTGCACC CAACTGATCT TCAGCATCTT |
| 8761 | TTACTTTCAC CAGCGTTTCT GGGTGAGCAA AAACAGGAAG GCAAAATGCC GCAAAAAAGG |
| 8821 | GAATAAGGGC GACACGGAAA TGTTGAATAC TCATATTCTT CCTTTTTCAA TATTATTGAA |
| 8881 | GCATTTATCA GGGTTATTGT CTCATGAGCG GATACATATT TGAATGTATT TAGAAAAATA |
| 8941 | AACAAATAGG GGTCAGTGTT ACAACCAATT AACCAATTCT GAACATTATC GCG |

SEQ ID NO 2: Complete vector DNA sequence of the of the acceptor mutant.

| | |
|---|---|
| 1 | CTCATGACCA AAATCCCTTA ACGTGAGTTA CGCGCGCGTC GTTCCACTGA GCGTCAGACC |
| 61 | CCGTAGAAAA GATCAAAGGA TCTTCTTGAG ATCCTTTTTT TCTGCGCGTA ATCTGCTGCT |
| 121 | TGCAAACAAA AAAACCACCG CTACCAGCGG TGGTTTGTTT GCCGGATCAA GAGCTACCAA |
| 181 | CTCTTTTTCC GAAGGTAACT GGCTTCAGCA GAGCGCAGAT ACCAAATACT GTTCTTCTAG |
| 241 | TGTAGCCGTA GTTAGCCCAC CACTTCAAGA ACTCTGTAGC ACCGCCTACA TACCTCGCTC |
| 301 | TGCTAATCCT GTTACCAGTG GCTGCTGCCA GTGGCGATAA GTCGTGTCTT ACCGGGTTGG |
| 361 | ACTCAAGACG ATAGTTACCG GATAAGGCGC AGCGGTCGGG CTGAACGGGG GGTTCGTGCA |
| 421 | CACAGCCCAG CTTGGAGCGA ACGACCTACA CCGAACTGAG ATACCTACAG CGTGAGCTAT |
| 481 | GAGAAAGCGC CACGCTTCCC GAAGGGAGAA AGGCGGACAG GTATCCGGTA AGCGGCAGGG |
| 541 | TCGGAACAGG AGAGCGCACG AGGGAGCTTC CAGGGGGAAA CGCCTGGTAT CTTTATAGTC |
| 601 | CTGTCGGGTT TCGCCACCTC TGACTTGAGC GTCGATTTTT GTGATGCTCG TCAGGGGGGC |
| 661 | GGAGCCTATG GAAAAACGCC AGCAACGCGG CCTTTTTACG GTTCCTGGCC TTTTGCTGGC |
| 721 | CTTTTGCTCA CATGTTCTTT CCTGCGTTAT CCCCTGATTC TGTGGATAAC CGTATTACCG |
| 781 | CCTTTGAGTG AGCTGATACC GCTCGCCGCA GCCGAACGAC CGAGCGCAGC GAGTCAGTGA |
| 841 | GCGAGGAAGC GGAAGGCGAG AGTAGGGAAC TGCCAGGCAT CAAACTAAGC AGAAGGCCCC |
| 901 | TGACGGATGG CCTTTTTGCG TTTCTACAAA CTCTTTCTGT GTTGTAAAAC GACGGCCAGT |
| 961 | CTTAAGCTCG GGCCCCCTGG GCGGTTCTGA TAACGAGTAA TCGTTAATCC GCAAATAACG |
| 1021 | TAAAAACCCG CTTCGGCGGG TTTTTTTATG GGGGGAGTTT AGGGAAAGAG CATTTGTCAG |
| 1081 | AATATTTAAG GGCGCCTGTC ACTTTGCTTG ATATATGAGA ATTATTTAAC CTTATAAATG |
| 1141 | AGAAAAAAGC AACGCACTTT AAATAAGATA CGTTGCTTTT TCGATTGATG AACACCTATA |
| 1201 | ATTAAACTAT TCATCTATTA TTTATGATTT TTTGTATATA CAATATTCT AGTTTGTTAA |
| 1261 | AGAGAATTAA GAAAATAAAT CTCGAAAATA ATAAAGGGAA AATCAGTTTT TGATATCAAA |
| 1321 | ATTATACATG TCAACGATAA TACAAAATAT AATACAAACT ATAAGATGTT ATCAGTATTT |
| 1381 | ATTATCATTT AGAATAAATT TTGTGTCGCC CTTAATTGTG AGCGGATAAC AATTACGAGC |
| 1441 | TTCATGCACA GTGGCGTTGA CATTGATTAT TGACTAGTTA TTAATAGTAA TCAATTACGG |
| 1501 | GGTCATTAGT TCATAGCCCA TATATGGAGT TCCGCGTTAC ATAACTTACG GTAAATGGCC |
| 1561 | CGCCTGGCTG ACCGCCCAAC GACCCCCGCC CATTGACGTC AATAATGACG TATGTTCCCA |
| 1621 | TAGTAACGCC AATAGGGACT TTCCATTGAC GTCAATGGGT GGAGTATTTA CGGTAAACTG |

| | |
|---|---|
| 1681 | CCCACTTGGC AGTACATCAA GTGTATCATA TGCCAAGTAC GCCCCCTATT GACGTCAATG |
| 1741 | ACGGTAAATG GCCCGCCTGG CATTATGCCC AGTACATGAC CTTATGGGAC TTTCCTACTT |
| 1801 | GGCAGTACAT CTACGTATTA GTCATCGCTA TTACCATGGT GATGCGGTTT TGGCAGTACA |
| 1861 | TCAATGGGCG TGGATAGCGG TTTGACTCAC GGGGATTTCC AAGTCTCCAC CCCATTGACG |
| 1921 | TCAATGGGAG TTTGTTTTGG CACCAAAATC AACGGGACTT TCCAAAATGT CGTAACAACT |
| 1981 | CCGCCCCATT GACGCAAATG GGCGGTAGGC GTGTACGGTG GGAGGTCTAT ATAAGCAGAG |
| 2041 | CTCTCTGGCT AACTAGAGAA CCCACTGCTT ACTGGCTTAT CGAAATTAAT ACGACTCACT |
| 2101 | ATAGGGGTAC CTGCCACCAT GGGGAAAAAC AAACTGCTGC ATCCAAGCCT GGTCCTGCTG |
| 2161 | CTGCTGGTTC TGCTGCCTAC TGACGCCTCT GTGAGCGGAA AGCCCCAGTA TATGGTTCTG |
| 2221 | GTCCCGTCCC TGCTGCACAC CGAGACCACA GAAAAGGGT GCGTGCTGCT GTCTTACCTG |
| 2281 | AATGAAACAG TGACTGTTAG TGCCTCACTG GAGAGTGTGC GCGGAAATCG TTCACTGTTC |
| 2341 | ACCGATCTGG AGGCGGAAAA CGATGTGCTG CATTGCGTCG CATTTGCTGT GCCAAAAAGC |
| 2401 | TCCTCTAATG AAGAAGTGAT GTTCCTGACC GTCCAGGTGA AGGGCCCTAC ACAGGAATTC |
| 2461 | AAAAAACGCA CTACCGTTAT GGTCAAAAAC GAGGATAGCC TGGTGTTTGT TCAGACAGAC |
| 2521 | AAATCCATCT ATAAGCCTGG TCAGACTGTG AAGTTCCGGG TGGTTAGCAT GGATGAAAAT |
| 2581 | TTTCACCCCC TGAACAGCT GATTCCACTG GTGTACATCC AGGACCCTAA AGGCAACCGC |
| 2641 | ATCGCCCAGT GGCAGTCTTT CCAGCTGGAA GGCGGTCTGA AGCAGTTTAG TTTCCCTCTG |
| 2701 | AGTTCAGAGC CGTTTCAGGG TTCTTATAAA GTCGTGGTTC AGAAAAAGAG TGGGGGACGT |
| 2761 | ACTGAACATC CTTTTACCGT TGAAGAGTTC GTCCTGCCGA AATTTGAGGT CCAGGTGACC |
| 2821 | GTTCCCAAGA TTATCACAAT TCTGGAAGAG GAAATGAACG TGAGCGTGTG CGGACTGTAT |
| 2881 | ACCTACGGCA AACCAGTGCC TGGTCACGTT ACAGTCAGTA TCTGCCGTAA GTACTCAGAT |
| 2941 | GCAAGCGACT GTCATGGCGA AGATTCACAG GCTTTTTGCG AGAAGTTCAG CGGCCAGCTG |
| 3001 | AACTCCCACG GTTGCTTCTA TCAGCAGGTG AAAACCAAGG TTTTTCAGCT GAAACGGAAG |
| 3061 | GAGTACGAAA TGAAACTGCA TACAGAAGCC CAGATTCAGG AAGAAGGCAC CGTCGTGGAA |
| 3121 | CTGACTGGTC GTCAGAGCTC CGAGATTACC CGGACAATCA CTAAACTGAG CTTCGTGAAG |
| 3181 | GTTGATTCCC ACTTTCGGCA GGGGATTCCC TTTTTCGGAC AGGTGCGCCT GGTTGACGGG |
| 3241 | AAAGGAGTTC CGATCCCCAA CAAAGTGATC TTTATTCGCG GCAATGAAGC CAACTATTAC |
| 3301 | AGCAACGCGA CAACTGATGA GCATGGGCTG GTGCAGTTCA GTATCAATAC CACAAACGTG |
| 3361 | ATGGGAACCT CACTGACAGT CCGCGTGAAT TATAAAGACC GTTCACCGTG TTATGGCTAC |
| 3421 | CAGTGGGTGA GCGAGGAACA CGAGGAAGCC CACCATACCG CGTACCTGGT TTTCAGCCCC |
| 3481 | TCCAAATCTT TTGTCCATCT GGAACCTATG TCTCACGAGC TGCCGTGCGG CCATACCCAG |
| 3541 | ACAGTGCAGG CACATTATAT TCTGAACGGC GGCACCCTGC TGGGTCTGAA AAAGCTGAGC |
| 3601 | TTTTATTACC TGATTATGGC TAAGGGGGGA ATCGTCCGCA CTGGCACCCA CGGTCTGCTG |
| 3661 | GTTAAACAGG AAGATATGAA GGGCCATTTC AGTATTTCAA TCCCTGTTAA AAGCGACATT |
| 3721 | GCTCCGGTCG CCCGTCTGCT GATCTATGCC GTGCTGCCAA CCGGCGATGT TATCGGTGAC |
| 3781 | TCCGCCAAAT ACGATGTGGA GAATTGTCTG GCGAACAAGG TTGACCTGAG CTTTTCCCCC |
| 3841 | TCTCAGAGTC TGCCAGCGTC TCATGCACAT CTGCGTGTGA CCGCAGCCCC TCAGAGCGTT |
| 3901 | TGCGCTCTGC GTGCAGTGGA TCAGTCCGTG CTGCTGATGA AGCCAGACGC AGAACTGTCT |
| 3961 | GCTAGCAGCG TGTATAATCT GCTGCCTGAG AAAGATCTGA CCGGGTTCCC AGGACCTCTG |

-continued

Sequences:

```
4021  AACGATCAGG ATGACGAAGA CTGTATTAAT CGCCACAACG TGTATATTAA TGGGATCACA
4081  TACACTCCGG TTTCAAGCAC CAACGAAAAA GATATGTACA GCTTCCTGGA GGACATGGGT
4141  CTGAAAGCGT TTACCAATTC CAAGATCCGG AAACCCCAAG ATGTGCCCAC AGCTCGAGCA
4201  GTATGAAATG CACGGACCTG AGGGTCTGCG TGTGGGCTTT TACGAATCTG ATGTGATGGG
4261  ACGTGGTCAT GCACGTCTGG TTCATGTCGA GGAACCACAC ACCGAAAAGC TTCGTAAATA
4321  CTTCCCTGAG ACCTGGATTT GGGACCTGGT TGTGGTGAAC TCCGCGGGTG TGGCAGAAGT
4381  GGGTGTTACC GTCCCGGATA CTATTACCGA ATGGAAAGCA GGTGCCTTCT GTCTGTCTGA
4441  GGATGCAGGG CTGGGAATCT CCTCTACAGC CTCTCTGCGC GCGTTTCAGC CCTTTTTCGT
4501  CGAACTGACT ATGCCATATA GCGTGATTCG TGGCGAGGCA TTCACTCTGA AAGCTACCGT
4561  GCTGAATTAC CTGCCCAAGT GCATCCGCGT GAGCGTGCAG CTGGAAGCTA GTCCCGCCTT
4621  TCTGGCGGTC CCAGTGGAGA AGGAACAGGC ACCGCACTGC ATTTGTGCTA ACGGCCGGCA
4681  GACTGTTTCC TGGGCCGTCA CCCCCAAATC TCTGGGTAAT GTGAACTTCA CCGTTTCAGC
4741  AGAGGCTCTG GAAAGCCAGG AGCTGTGCGG CACCGAAGTC CCATCCGTGC CTGAGCATGG
4801  TCGCAAAGAT ACAGTCATCA AGCCTCTGCT GGTTGAACCG GAAGGCCTGG AGAAGGAAAC
4861  TACCTTTAAT TCTCTGCTGT GCCCAAGTGG CGGTGAAGTG TCCGAGGAAC TGTCTCTGAA
4921  ACTGCCGCCC AACGTGGTCG AGGAATCTGC CCGTGCGTCA GTTAGCGTCC TGGGGGATAT
4981  TCTGGGAAGT GCCATGCAGA ATACCCAGAA CCTGCTGCAG ATGCCGTATG CTGTGGCGA
5041  GCAGAATATG GTTCTGTTTG CGCCCAACAT CTATGTCCTG GATTACCTGA ATGAAACACA
5101  GCAGCTGACT CCTGAAATCA AAAGCAAGGC AATCGGGTAT CTGAATACCG ATACCAGCG
5161  GCAGCTGAAC TATAAGCACT ACGACGGCTC CTATTCTACC TTCGGCGAAC GGTACGGTCG
5221  CAATCAGGGG AACACTTGGC TGACCGCCTT TGTGCTGAAA ACCTTTGCCC AGGCTCGCGC
5281  CTATATCTTT ATTGATGAGG CCCATATTAC ACAGGCGCTG ATCTGGCTGT CACAGCGCCA
5341  GAAGGACAAC GGGTGTTTCC GTAGTTCAGG AAGCCTGCTG AACAATGCCA TCAAAGGCGG
5401  CGTCGAGGAT GAAGTGACAC TGAGCGCATA CATTACTATC GCTCTGCTGG AAATCCCTCT
5461  GACAGTGACT CACCCGGTGG TTCGCAATGC TCTGTTTTGC CTGGAAAGTG CATGGAAAAC
5521  AGCTCAGGAA GGCGATCACG GATCACACGT GTATACTAAG GCACTGCTGG CGTACGCATT
5581  CGCTCTGGCC GGCAACCAGG ATAAACGTAA AGAAGTGCTG AAATCACTGA ATGAGGAAGC
5641  AGTTAAAAAG GACAACAGCG TCCACTGGGA ACGGCCGCAG AAACCCAAGG CTCCAGTGGG
5701  TCACTTTTAT GAGCCTCAGG CACCGAGTGC TGAGGTGGAA ATGACCTCAT ATGTTCTGCT
5761  GGCATACCTG ACCGCACAGC CTGCCCCCAC ATCAGAAGAT CTGACAAGCC CACTAATAT
5821  TGTGAAATGG ATCACCAAGC AGCAGAACGC GCAGGGCGGT TTTAGCTCCA CCCAGGACAC
5881  AGTCGTGGCA CTGCACGCTC TGTCTAAATA TGGGGCAGCT ACCTTCACAC GCACTGGAAA
5941  GGCCGCGCAA GTGACTATTC AGTCTAGTGG CACCTTTTCA AGCAAGTTCC AGGTGGATAA
6001  CAATAACCGT CTGCTGCTGC AGCAGGTGTC CCTGCCCGAA CTGCCAGGCG AGTACTCTAT
6061  GAAAGTCACT GGGGAAGGAT GCGTGTATCT GCAGACCTCC CTGAAATACA ATATTCTGCC
6121  CGAGAAAGAA GAATTTCCAT TCGCACTGGG CGTGCAGACC CTGCCTCAGA CATGCGATGA
6181  ACCGAAGGCT CATACTTCTT TTCAGATCAG TCTGTCAGTG AGCTATACCG GGTCCCGCTC
6241  TGCCAGTAAC ATGGCGATTG TGGATGTGAA AATGGTGAGT GGATTCATCC CTCTGAAACC
6301  GACTGTGAAG ATGCTGGAAC GGAGTAATCA CGTTTCACGC ACCGAGGTCT CCTCTAACCA
```

| | Sequences: |
|---|---|
| 6361 | TGTGCTGATC TACCTGGATA AAGTGTCCAA TCAGACACTG TCTCTGTTTT TCACTGTGCT |
| 6421 | GCAGGATGTC CCCGTGCGTG ACCTGAAACC AGCCATTGTT AAGGTCTATG ATTATTACGA |
| 6481 | AACCGACGAG TTCGCGATCG CAGAATACAA CGCGCCGTGC AGCAAAGACC TGGGGAATGC |
| 6541 | TGACTACAAG GACGACGACG ACAAGGGGGC AAGCCACCAC CATCACCATC ACTAAGGATC |
| 6601 | CAAAATCAGC CTCGACTGTG CCTTCTAGTT GCCAGCCATC TGTTGTTTGC CCCTCCCCCG |
| 6661 | TGCCTTCCTT GACCCTGGAA GGTGCCACTC CCACTGTCCT TTCCTAATAA AATGAGGAAA |
| 6721 | TTGCATCACA ACACTCAACC CTATCTCGGT CTATTCTTTT GATTTATAAG GGATTTTGCC |
| 6781 | GATTTCGGCC TATTGGTTAA AAAATGAGCT GATTTAACAA AAATTTAACG CGAATTAATT |
| 6841 | CTGTGGAATG TGTGTCAGTT AGGGTGTGGA AAGTCCCCAG GCTCCCCAGC AGGCAGAAGT |
| 6901 | ATGCAAAGCA TGCATCTCAA TTAGTCAGCA ACCAGGTGTG GAAAGTCCCC AGGCTCCCCA |
| 6961 | GCAGGCAGAA GTATGCAAAG CATGCATCTC AATTAGTCAG CAACCATAGT CCCGCCCCTA |
| 7021 | ACTCCGCCCA TCCCGCCCCT AACTCCGCCC AGTTCCGCCC ATTCTCCGCC CCATGGCTGA |
| 7081 | CTAATTTTTT TTATTTATGC AGAGGCCGAG GCCGCCTCTG CCTCTGAGCT ATTCCAGAAG |
| 7141 | TAGTGAGGAG GCTTTTTTGG AGGCCTAGGC TTTTGCAAAA AGCTCCCGGG AGCTTGTATA |
| 7201 | TCCATTTTCG GATCTGATCA GCACGTGTTG ACAATTAATC ATCGGCATAG TATATCGGCA |
| 7261 | TAGTATAATA CGACAAGGTG AGGAACTAAA CCATGGCCAA GCCTTTGTCT CAAGAAGAAT |
| 7321 | CCACCCTCAT TGAAAGAGCA ACGGCTACAA TCAACAGCAT CCCCATCTCT GAAGACTACA |
| 7381 | GCGTCGCCAG CGCAGCTCTC TCTAGCGACG GCCGCATCTT CACTGGTGTC AATGTATATC |
| 7441 | ATTTTACTGG GGGACCTTGT GCAGAACTCG TGGTGCTGGG CACTGCTGCT GCTGCGGCAG |
| 7501 | CTGGCAACCT GACTTGTATC GTCGCGATCG GAAATGAGAA CAGGGGCATC TTGAGCCCCT |
| 7561 | GCGGACGGTG CCGACAGGTG CTTCTCGATC TGCATCCTGG GATCAAAGCC ATAGTGAAGG |
| 7621 | ACAGTGATGG ACAGCCGACG GCAGTTGGGA TTCGTGAATT GCTGCCCTCT GGTTATGTGT |
| 7681 | GGGAGGGCTA ACACGTGCTA CGAGAfTTCG ATTCCACCGC CGCCTTCTAT GAAAGGTTGG |
| 7741 | GCTTCGGAAT CGTTTTCCGG GACGCCGGCT GGATGATCCT CCAGCGCGGG GATCTCATGC |
| 7801 | TGGAGTTCTT CGCCCACCCC AACTTGTTTA TTGCAGCTTA ATGGTTAC AAATAAAGCA |
| 7861 | ATAGCATCAC AAATTTCACA AATAAAGCAT TTTTTTCACT GCATTCTAGT TGTGGTTTGT |
| 7921 | CCAAACTCAT CAATGTATCT TATCATGTCT GTATACCGTC GACCTCTAGC TAGAGCTTGG |
| 7981 | CGTAATCATG GTCATTACCA ATGCTTAATC AGTGAGGCAC CTATCTCAGC GATCTGTCTA |
| 8041 | TTTCGTTCAT CCATAGTTGC CTGACTCCCC GTCGTGTAGA TAACTACGAT ACGGGAGGGC |
| 8101 | TTACCATCTG GCCCCAGCGC TGCGATGATA CCGCGAGAAC CACGCTCACC GGCTCCGGAT |
| 8161 | TTATCAGCAA TAAACCAGCC AGCCGGAAGG GCCGAGCGCA GAAGTGGTCC TGCAACTTTA |
| 8221 | TCCGCCTCCA TCCAGTCTAT TAATTGTTGC CGGGAAGCTA GAGTAAGTAG TTCGCCAGTT |
| 8281 | AATAGTTTGC GCAACGTTGT TGCCATCGCT ACAGGCATCG TGGTGTCACG CTCGTCGTTT |
| 8341 | GGTATGGCTT CATTCAGCTC CGGTTCCCAA CGATCAAGGC GAGTTACATG ATCCCCCATG |
| 8401 | TTGTGCAAAA AAGCGGTTAG CTCCTTCGGT CCTCCGATCG TTGTCAGAAG TAAGTTGGCC |
| 8461 | GCAGTGTTAT CACTCATGGT TATGGCAGCA CTGCATAATT CTCTTACTGT CATGCCATCC |
| 8521 | GTAAGATGCT TTTCTGTGAC TGGTGAGTAC TCAACCAAGT CATTCTGAGA ATAGTGTATG |
| 8581 | CGGCGACCGA GTTGCTCTTG CCCGGCGTCA ATACGGGATA ATACCGCGCC ACATAGCAGA |
| 8641 | ACTTTAAAAG TGCTCATCAT TGGAAAACGT TCTTCGGGGC GAAAACTCTC AAGGATCTTA |

| | Sequences: |
|---|---|
| 8701 | CCGCTGTTGA GATCCAGTTC GATGTAACCC ACTCGTGCAC CCAACTGATC TTCAGCATCT |
| 8761 | TTTACTTTCA CCAGCGTTTC TGGGTGAGCA AAAACAGGAA GGCAAAATGC CGCAAAAAAG |
| 8821 | GGAATAAGGG CGACACGGAA ATGTTGAATA CTCATATTCT TCCTTTTTCA ATATTATTGA |
| 8881 | AGCATTTATC AGGGTTATTG TCTCATGAGC GGATACATAT TTGAATGTAT TTAGAAAAAT |
| 8941 | AAACAAATAG GGGTCAGTGT TACAACCAAT TAACCAATTC TGAACATTAT CGCG |

SEQ ID NO 3: Amino Acid Sequence of Tagged wild-type human A2M
```
   1  MGKNKLLHPS LVLLLLVLLP TDASVSGKPQ YMVLVPSLLH TETTEKGCVL LSYLNETVTV
  61  SASLESVRGN RSLFTDLEAE NDVLHCVAFA VPKSSSNEEV MFLTVQVKGP TQEFKKRTTV
 121  MVKNEDSLVF VQTDKSIYKP GQTVKFRVVS MDENFHPLNE LIPLVYIQDP KGNRIAQWQS
 181  FQLEGGLKQF SFPLSSEPFQ GSYKVVVQKK SGGRTEHPFT VEEFVLPKFE VQVTVPKIIT
 241  ILEEEMNVSV CGLYTYGKPV PGHVTVSICR KYSDASDCHG EDSQAFCEKF SGQLNSHGCF
 301  YQQVKTKVFQ LKRKEYEMKL HTEAQIQEEG TVVELTGRQS SEITRTITKL SFVKVDSHFR
 361  QGIPFFGQVR LVDGKGVPIP NKVIFIRGNE ANYYSNATTD EHGLVQFSIN TTNVMGTSLT
 421  VRVNYKDRSP CYGYQWVSEE HEEAHHTAYL VFSPSKSFVH LEPMSHELPC GHTQTVQAHY
 481  ILNGGTLLGL KKLSFYYLIM AKGGIVRTGT HGLLVKQEDM KGHFSISIPV KSDIAPVARL
 541  LIYAVLPTGD VIGDSAKYDV ENCLANKVDL SFSPSQSLPA SHAHLRVTAA PQSVCALRAV
 601  DQSVLLMKPD AELSASSVYN LLPEKDLTGF PGPLNDQDDE DCINRHNVYI NGITYTPVSS
 661  TNEKDMYSFL EDMGLKAFTN SKIRKPKMCP QLQQYEMHGP EGLRVGFYES DVMGRGHARL
 721  VHVEEPHTET VRKYFPETWI WDLVVVNSAG VAEVGVTVPD TITEWKAGAF CLSEDAGLGI
 781  SSTASLRAFQ PFFVELTMPY SVIRGEAFTL KATVLNYLPK CIRVSVQLEA SPAFLAVPVE
 841  KEQAPHCICA NGRQTVSWAV TPKSLGNVNF TVSAEALESQ ELCGTEVPSV PEHGRKDTVI
 901  KPLLVEPEGL EKETTFNSLL CPSGGEVSEE LSLKLPPNVV EESARASVSV LGDILGSAMQ
 961  NTQNLLQMPY GCGEQNMVLF APNIYVLDYL NETQQLTPEI KSKAIGYLNT GYQRQLNYKH
1021  YDGSYSTFGE RYGRNQGNTW LTAFVLKTFA QARAYIFIDE AHITQALIWL SQRQKDNGCF
1081  RSSGSLLNNA IKGGVEDEVT LSAYITIALL EIPLTVTHPV VRNALFCLES AWKTAQEGDH
1141  GSHVYTKALL AYAFALAGNQ DKRKEVLKSL NEEAVKKDNS VHWERPQKPK APVGHFYEPQ
1201  APSAEVEMTS YVLLAYLTAQ RAPTSEDLTS ATNIVKWITK QQNAQGGFSS TQDTVVALHA
1261  LSKYGAATFT RTGKAAQVTI QSSGTFSSKF QVDNNNRLLL QQVSLPELPG EYSMKVTGEG
1321  CVYLQTSLKY NILPEKEEFP FALGVQTLPQ TCDEPKAHTS FQISLSVSYT GSRSASNMAI
1381  VDVKMVSGFI PLKPTVKMLE RSNHVSRTEV SSNHVLIYLD KVSNQTLSLF FTVLQDVPVR
1441  DLKPAIVKVY DYYETDEFAI AEYNAPCSKD LGNADYKDDD DKGASHHHHHH
```

SEQ ID NO 4: Amino Acid Sequence of the Acceptor Mutant.
```
   1  MGKNKLLHPS LVLLLLVLLP TDASVSGKPQ YMVLVPSLLH TETTEKGCVL LSYLNETVTV
  61  SASLESVRGN RSLFTDLEAE NDVLHCVAFA VPKSSSNEEV MFLTVQVKGP TQEFKKRTTV
 121  MVKNEDSLVF VQTDKSIYKP GQTVKFRVVS MDENFHPLNE LIPLVYIQDP KGNRIAQWQS
 181  FQLEGGLKQF SFPLSSEPFQ GSYKVVVQKK SGGRTEHPFT VEEFVLPKFE VQVTVPKIIT
 241  ILEEEMNVSV CGLYTYGKPV PGHVTVSICR KYSDASDCHG EDSQAFCEKF SGQLNSHGCF
 301  YQQVKTKVFQ LKRKEYEMKL HTEAQIQEEG TVVELTGRQS SEITRTITKL SFVKVDSHFR
 361  QGIPFFGQVR LVDGKGVPIP NKVIFIRGNE ANYYSNATTD EHGLVQFSIN TTNVMGTSLT
 421  VRVNYKDRSP CYGYQWVSEE HEEAHHTAYL VFSPSKSFVH LEPMSHELPC GHTQTVQAHY
```

```
                                Sequences:

481   ILNGGTLLGL KKLSFYYLIM AKGGIVRTGT HGLLVKQEDM KGHFSISIPV KSDIAPVARL

541   LIYAVLPTGD VIGDSAKYDV ENCLANKVDL SFSPSQSLPA SHAHLRVTAA PQSVCALRAV

601   DQSVLLMKPD AELSASSVYN LLPEKDLTGF PGPLNDQDDE DCINRHNVYI NGITYTPVSS

661   TNEKDMYSFL EDMGLKAFTN SKIRKPKMCP QLEQYEMHGP EGLRVGFYES DVMGRGHARL

721   VHVEEPHTEK LRKYFPETWI WDLVVVNSAG VAEVGVTVPD TITEWKAGAF CLSEDAGLGI

781   SSTASLRAFQ PFFVELTMPY SVIRGEAFTL KATVLNYLPK CIRVSVQLEA SPAFLAVPVE

841   KEQAPHCICA NGRQTVSWAV TPKSLGNVNF TVSAEALESQ ELCGTEVPSV PEHGRKDTVI

901   KPLLVEPEGL EKETTFNSLL CPSGGEVSEE LSLKLPPNVV EESARASVSV LGDILGSAMQ

961   NTQNLLQMPY GCGEQNMVLF APNIYVLDYL NETQQLTPEI KSKAIGYLNT GYQRQLNYKH

1021   YDGSYSTFGE RYGRNQGNTW LTAFVLKTFA QARAYIFIDE AHITQALIWL SQRQKDNGCF

1081   RSSGSLLNNA IKGGVEDEVT LSAYITIALL EIPLTVTHPV VRNALFCLES AWKTAQEGDH

1141   GSHVYTKALL AYAFALAGNQ DKRKEVLKSL NEEAVKKDNS VHWERPQKPK APVGHFYEPQ

1201   APSAEVEMTS YVLLAYLTAQ PAPTSEDLTS ATNIVKWITK QQNAQGGFSS TQDTVVALHA

1261   LSKYGAATFT RTGKAAQVTI QSSGTFSSKF QVDNNNRLLL QQVSLPELPG EYSMKVTGEG

1321   CVYLQTSLKY NILPEKEEFP FALGVQTLPQ TCDEPKAHTS FQISLSVSYT GSRSASNMAI

1381   VDVKMVSGFI PLKPTVKMLE RSNHVSRTEV SSNHVLIYLD KVSNQTLSLF FTVLQDVPVR

1441   DLKPAIVKVY DYYETDEFAI AEYNAPCSKD LGNADYKDDD DKGASHHHHH H
```

SEQ ID NO 5: Amino Acid Sequence of wild-type A2M Bait Region.
SEQ ID NO: 5-PQLQQYEMHGPEGLRVGFYESDVMGRGHARLVHVEEPHTET SEQ ID NOs 6-30: Amino Acid Sequences of Variant Bait Regions
SEQ ID NO: 6-LEHGPEGEGEGEGIPENFYGVSEDLVVQISELEGRGSVEEPHTKL

SEQ ID NO: 7-LEHGPEGEGEGEGIPENFFGVRYSEDLVVQISELEGRGSVEEPHTKL

SEQ ID NO: 8-LEHGPEGEGEGEGIPENFFGVLYSEDLVVQISELEGRGSVEEPHTKL

SEQ ID NO: 9-LEHGPEGEGEGEGIPENFFGVPRYLSEDLVVQISELEGRGSVEEPHTKL

SEQ ID NO: 10-LEHGPEGEGLGEGIPENFYGVSEDLVVQISELEGRGSVEEPHTKL

SEQ ID NO: 11-LEHGPEGEGEGPRYLTAIPENFFGVSEDLVVQISELEGRGSVEEPHTKL

SEQ ID NO: 12-LEHGPEGEGEGEGIPENFEFRGVSEDLVVQISELEGRGSVEEPHTKL

SEQ ID NO: 13-LEHGPRYLTAEGEGEGIPENFFGVSEDLVVQISELEGRGSVEEPHTKL

SEQ ID NO: 14-LEHGPEGEGEGEGIPRYLTAENFFGVSEDLVVQISELEGRGSVEEPHTKL

SEQ ID NO: 15-LEHGPEGEGEGEGIPENFFGVSEDLVVQISELEGRGSRYLTAVEEPHTKL

SEQ ID NO: 16-LEHGPEFRGVTRYLTAIPENFYGVSELEGRGSSEDLVVQIVEEPHTKL

SEQ ID NO: 17-LEHGPTEGEARGSIPENFYGVSEDLVVQISELEGRGSVEEPHTKL

SEQ ID NO: 18-LEHGPIPENFYGLEGEGEGEGEAIPMSIPRYLTAEFRGVTVEEPHTKL

SEQ ID NO: 19-LEHGPEGEGEGEFRGVTIPENFYGVSEDLVVQISELEGRGSVEEPHTKL

SEQ ID NO: 20-LEHGPEFRGVTEGEGEGIPENFYGVSEDLVVQISELEGRGSVEEPHTKL

SEQ ID NO: 21-LEHGPTEGEARGSPRYLTAIPENFYGVSEDLVVQISELEGRGSPHTKL

SEQ ID NO: 22-LEHGPEGEGEGEFRGVTIPENFFGVPRYLTASEDLVVQISELEGRGSPHTKL

SEQ ID NO: 23-LEHGPIPENFYGVEGEGLGIGSEDLVVQISELEGRGSVEEPHTKL

SEQ ID NO: 24-LEHGPIPENFYGVEGEGEGEGSEDLVVQISELEGRGSVEEPHTKL

SEQ ID NO: 25-LEHGPEGEGEGEGIPENFYGVSEDLYTASELEGRGSVEEPHTKL

-continued

| Sequences: |
|---|

SEQ ID NO: 26-LEHGPEGEGEGEFRAAPFLTAIPENFFGVSEDLVVQISELEGRGSPHTKL

SEQ ID NO: 27-LEQYEMHGPEGEGEGEGIPENFYGVSEDLYTASELEGRGSVEEPHTKL

SEQ ID NO: 28-LEQYEMHGPEGEGEGEFRAAPFLTAIPENFFGVSEDLVVQISELEGRGSPHTKL

SEQ ID NO: 29-LEQPEGEGEGPRYLTAIPENFFGVSEDLVVQISELEGRGSVEEPHTKL

SEQ ID NO: 30-LEQYEMHGPEGEGEGPRYLTAIPENFFGVSEDLVVQISELEGRGSPHTKL

SEQ ID NOs 31-83:
Amino Acid Sequences of Protease Recognition Sites and Consensus Protease
Recognition Sites of Variant A2M Bait Regions
SEQ ID NO: 31-TAQEAGEG

SEQ ID NO: 32-VSQELGQR

SEQ ID NO: 33-IPENFFGV

SEQ ID NO: 34-SEDLVVQI

SEQ ID NO: 35-EAIPMSIPT

SEQ ID NO: 36-ELEGRG

SEQ ID NO: 37-EEEGLG

SEQ ID NO: 38-EEEGGG

SEQ ID NO: 39-ESESEG

SEQ ID NO: 40-EFEVEG

SEQ ID NO: 41-EIEEGG

SEQ ID NO: 42-ERESTG

SEQ ID NO: 43-EREAQG

SEQ ID NO: 44-EKETGG

SEQ ID NO: 45-EREAQG

SEQ ID NO: 46-ETEGRG

SEQ ID NO: 47-ENEAGG

SEQ ID NO: 48-EPESSG

SEQ ID NO: 49-EPESSG

SEQ ID NO: 50-ESESEG

SEQ ID NO: 51-EGEQEG

SEQ ID NO: 52-EPEPEG

SEQ ID NO: 53-EREAQG

SEQ ID NO: 54-EAEGTG

SEQ ID NO: 55-EFPEVEG

SEQ ID NO: 56-GEEGVEEG

SEQ ID NO: 57-GARGLEG

SEQ ID NO: 58-GPPGLAPG

SEQ ID NO: 59-GYPGSSRG

SEQ ID NO: 60-GFAGLPNG

SEQ ID NO: 61-GGGGSLLG

SEQ ID NO: 62-GPAGAARG

| Sequences: |
|---|

SEQ ID NO: 63-GLEGGGGG

SEQ ID NO: 64-GGGGSLLG

SEQ ID NO: 65-GFFGFPIG

SEQ ID NO: 66-EPAGAARG

SEQ ID NO: 67-GDRGLPIG

SEQ ID NO: 68-GEPEGAKG

SEQ ID NO: 69-GFKEGVEG

SEQ ID NO: 70-GVEGVELG

SEQ ID NO: 71-GFKEGVEG

SEQ ID NO: 72-GERGVLG

SEQ ID NO: 73-GGGSLLG

SEQ ID NO: 74-PEEGVEEG

SEQ ID NO: 75-GFKEGVEG

SEQ ID NO: 76-GFKEGVEG

SEQ ID NO: 77-GEPEGAKG

SEQ ID NO: 78-TEGEARGS

SEQ ID NO: 79-EGEGEGEG

SEQ ID NO: 80-EFRGVT

SEQ ID NO: 81-PRYLTA

SEQ ID NO: 82-(G/P/E)XX(G/E)-ΦXXG, where Φ is G, V, L, S, A, F, or T and X is any amino acid.

SEQ ID NO: 83-EXE-ΘXG, where Θ is G, V, E, A, T, S, Q, P, N, or D and X is any amino acid.

SEQ ID NOs 84-143: Other Exemplary Variant Bait Region Sequences.
SEQ ID NO 84: LEQYEMHGPE GLRVGKEEEG LGSIPENFFG VSELEGRGSK L

SEQ ID NO 85: LEQYEMHGPE GLRVGIPENF FGVSELEGRG SKEEEGLGSK L

SEQ ID NO 86: LEQYEMHGPE GLRVGSELEG RGSKEEEGLG SIPENFFGVK L

SEQ ID NO 87: LEQYEMHGPE GLRVGKEEEG LGSSELEGRG STAQEAGEGK L

SEQ ID NO 88: LEQYEMHGPE GLRVGIPENF FGVFYESDVM GRGHARLVHV EEPHTKLL

SEQ ID NO 89: LEQYEMHGPE GLRVGKEEEG LGSFYESDVM GRGHARLVHV EEPHTKLL

SEQ ID NO 90: LEQYEMHGPE GLRVGSELEG RGSFYESDVM GRGHARLVHV EEPHTKLL

SEQ ID NO 91: LEQYEMHGPE GLRVGEAIPM SIPFYESDVM GRGHARLVHV EEPHTKLL

SEQ ID NO 92: LEQYEMHGPE GLRVGTAQEA GEGFYESDVM GRGHARLVHV EEPHTKLL

SEQ ID NO 93: LEQYEMHGPE GLRVGVSQEL GQRFYESDVM GRGHARLVHV EEPHTKLL

SEQ ID NO 94: LEQYEMHGPE GLRVGTEGEA RGSFYESDVM GRGHARLVHV EEPHTKLL

SEQ ID NO 95: LEQYEMHGPE GLRVGTSEDL VVQFYESDVM GRGHARLVHV EEPHTKLL

SEQ ID NO 96: LEQYEMHGPE GLRVGEGEGE GEGFYESDVM GRGHARLVHV EEPHTKLL

SEQ ID NO 97: LEQYEMHGPE GLRVGGEEGV EEGFYESDVM GRGHARLVHV EEPHTKLL

SEQ ID NO 98: LEQYEMHGPE GLRVGGARGL EGFYESDVMG RGHARLVHVE EPHTKL

SEQ ID NO 99: LEQYEMHGPE GLRVGGPPGL APGFYESDVM GRGHARLVHV EEPHTKLL

| Sequences: |
|---|
| SEQ ID NO 100: LEQYEMHGPE GLRVGGEPEG AKGFYESDVM GRGHARLVHV EEPHTKLL |
| SEQ ID NO 101: LEQYEMHGPE GLRVGEEEGG GFYESDVMGR GHARLVHVEE PHTKL |
| SEQ ID NO 102: LEQYEMHGPE GLRVGGYPGS SRGFYESDVM GRGHARLVHV EEPHTKLL |
| SEQ ID NO 103: LEQYEMHGPE GLRVGGARGL EGGFAGLPNG GEEGVEEGKL |
| SEQ ID NO 104: LEQYEMHGPE GLRVGESESE GGGGGSLLGE FEVEGGFAGL PNGKL |
| SEQ ID NO 105: LEQYEMHGPE GLRVGGFKEG VEGEIEEGGG FKEGVEGKL |
| SEQ ID NO 106: LEQYEMHGPE GLRVGESESE GGFAGLPNGK EEEGLGSIPE NFFGVKL |
| SEQ ID NO 107: LEQYEMHGPE GLRVGIPENF FGVTSEDLVV QEAIPMSIPK L |
| SEQ ID NO 108: LEQYEMHGPE GLRVGEAIPM SIPTSEDLVV QIPENFFGVK L |
| SEQ ID NO 109: LEPAGAARGE SESEGGFFGF PIGERESTGG DRGLPIGENE AGGKL |
| SEQ ID NO 110: LETEGRGERE AQGEFPEVEG EEEGGGPEKE TGGEREAQGK L |
| SEQ ID NO 111: LEARGLEGGG GGSLLGGYPG SSRGGFKEGV EGGPAGAARG KL |
| SEQ ID NO 112: LEPGLAPGGE EGVEEGGPEE GVEEGGFKEG VEGEPESSGK L |
| SEQ ID NO 113: LEEGEARGST AQEAGEGPKE EEGLGSSELE GRGSPVSQEL GQRKL |
| SEQ ID NO 114: LEAQEAGEGK EEEGLGSPVS QELGQRSELE GRGSPTEGEA RGSKL |
| SEQ ID NO 115: LEEEEGLGSK EEEGLGSPKE EEGLGSKEEE GLGSPKEEEG LGSKL |
| SEQ ID NO 116: LEELEGRGSK EEEGLGSIPE NFFGVFYESD VMGRGHARLV HVEEPHTKL |
| SEQ ID NO 117: LEENFFGVTE GEARGSPTSE DLVVQKEEEG LGSEAIPMSI PKL |
| SEQ ID NO 118: LEIPMSIPKE EEGLGSIPEN FFGVTEGEAR GSPTSEDLVV QKL |
| SEQ ID NO 119: LELQQYEMHG PEGLRVGEAI PMSIPIPENF FGVKEEEGLG SKL |
| SEQ ID NO 120: LEEEGVEEGK EEEGLGSGPA GAARGSELEG RGSPTEGEAR GSKL |
| SEQ ID NO 121: LEPESSGEAI PMSIPTSEDL VVQIPENFFG VEAEGTGGER GVLGKL |
| SEQ ID NO 122: LEGGGSLLGE PEPEGEREAQ GGVEGVELGG FKEGVEGEQE GRGKL |
| SEQ ID NO 123: LESQELGQRE SESEGGSELEG RGSGFKEGVE GKEEEGLGSG FFGFPIGKL |
| SEQ ID NO 124: LEQYEMHGPK EEEGLGSSEL EGRGSEAIPM SIPTIPENFF GVVEEPHTKL |
| SEQ ID NO 125: LEQYEMHGPS ELEGRGSIPE NFFGVEAIPM SIPTSEDLVV QIVEEPHTKL |
| SEQ ID NO 126: LEQYEMHGPE GEGEGEGIPE NFFGVSEDLV VQISELEGRG SVEEPHTKL |
| SEQ ID NO 127: LEQYEMHGPI PENFFGVSEL EGRGSEAIPM SIPTEGEGEG EGVEEPHTKL |
| SEQ ID NO 128: LEQYEMHGPS ELEGRGSEAI PMSIPTKEEE GLGSIPENFF GVVEEPHTKL |
| SEQ ID NO 129: LEQYEMHGPE AIPMSIPTEG EGEGEGIPEN FFGVSEDLVV QIVEEPHTKL |
| SEQ ID NO 130: LEQYEMHGPS EDLVVQIEGE GEGEGIPENF FGVEAIPMSI PTVEEPHTKL |
| SEQ ID NO 131: LEQYEMHGPE GEGEGEGISE DLVVQIPENF FGVKEEEGLG SVEEPHTKL |
| SEQ ID NO 132: LEQYEMHGPE GEGEGEGIPE NFFGVSELEG RGSSEDLVVQ IVEEPHTKL |
| SEQ ID NO 133: LEQYEMHGPI PENFFGVEGE GEGESELEGR GSSEDLVVQI VEEPHTKL |
| SEQ ID NO 134: LEQYEMHGPS ELEGRGSIPE NFFGVKEEEG LGSSEDLVVQ IVEEPHTKL |
| SEQ ID NO 135: LEQYEMHGPI PENFFGVSEL EGRGSSEDLV VQIKEEEGLG SVEEPHTKL |
| SEQ ID NO 136: LEQYEMHGPK EEEGLGSIPE NFFGVSELEG RGSEGEGEGE GVEEPHTKL |
| SEQ ID NO 137: LEQYEMHGPS EDLVVQIKEE EGLGSIPENF FGVSELEGRG SVEEPHTKL |
| SEQ ID NO 138: LEQYEMHGPS EDLVVQIEGE GEGEGIPENF FGVKEEEGLG SVEEPHTKL |

-continued

```
Sequences:

SEQ ID NO 139:  LEQYEMHGPS EDLVVQIEGE GEGEGIPENF FGVEAIPMSI PTEPHTKL

SEQ ID NO 140:  LEQYEMHGPE GEGEGEGIPE NFFGVEAIPM SIPTSELEGR GSEPHTKL

SEQ ID NO 141:  LEQYEMHGPE AIPMSIPTSE LEGRGSIPEN FFGVEGEGEG EGEPHTKL

SEQ ID NO 142:  LEQYEMHGPS ELEGRGSIPE NFFGVEGEGE GEGKEEEGLG SVEEPHTKL

SEQ ID NO 143:  LEQYEMHGPI PENFFGVSED LVVQIEGEGE GEGEAIPMSI PTEPHTKL
```

EXAMPLES

Figure 1:
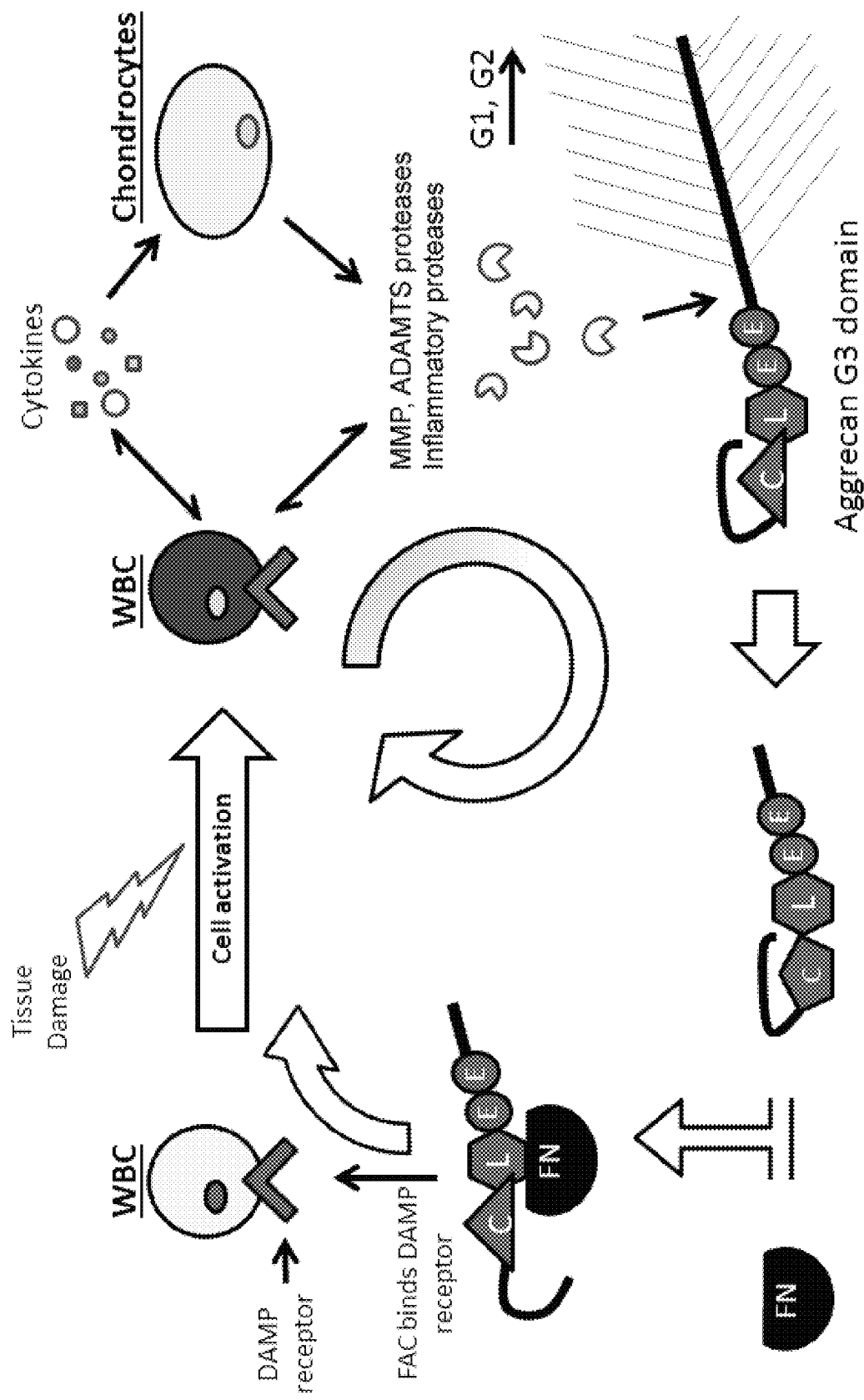
FIG. 1 depicts a schematic of the steps and signaling pathways associated with formation of a fibronectin-aggrecan complex (FAC) and the FAC-induced activation of Damage-Associated-Molecular Pattern (DAMP) receptor signaling in cells. The combination of the two processes creates a cyclic process that continually degrades cartilage.
Figures 2A, 2B:
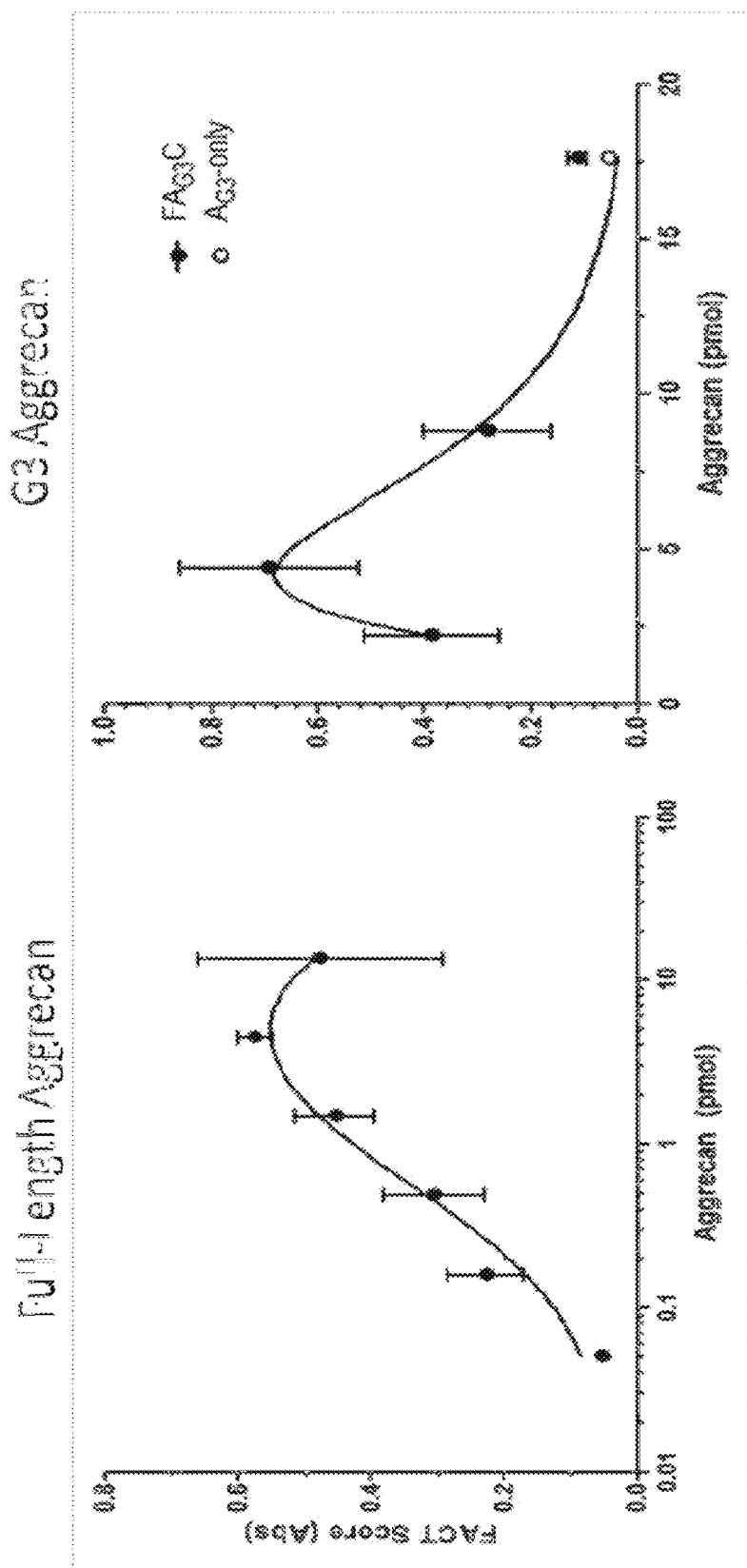
FIG. 2A and FIG. 2B are exemplary graphs depicting FAC formation using fibronectin to form a complex with purified full length Aggrecan or recombinant G3 Aggrecan. Both Aggrecan and the G3 domain bind fibronectin to form FAC.
Figure 3:
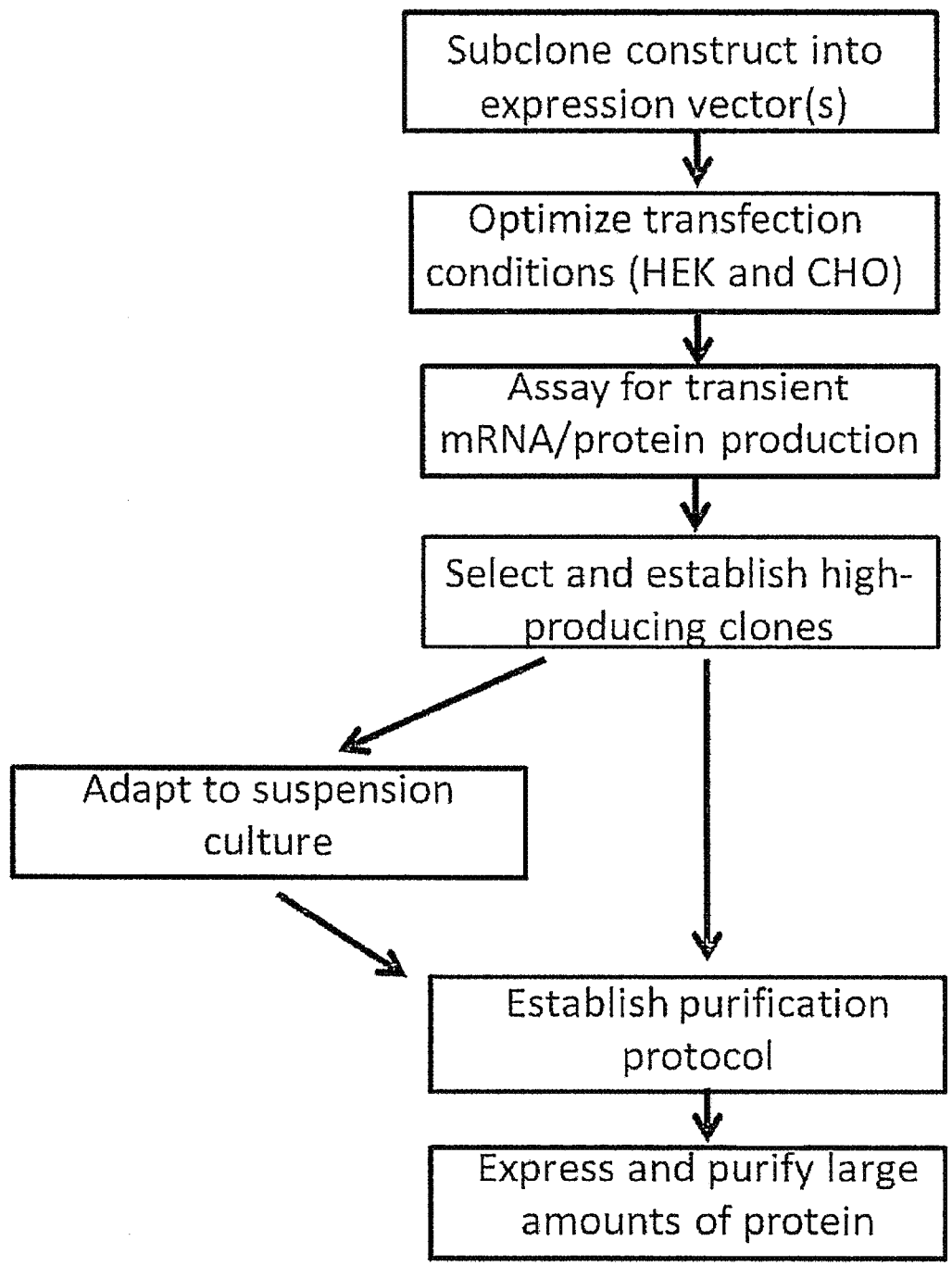
FIG. 3 depicts a flow chart of the steps for construct or protein expression.
Figure 4:
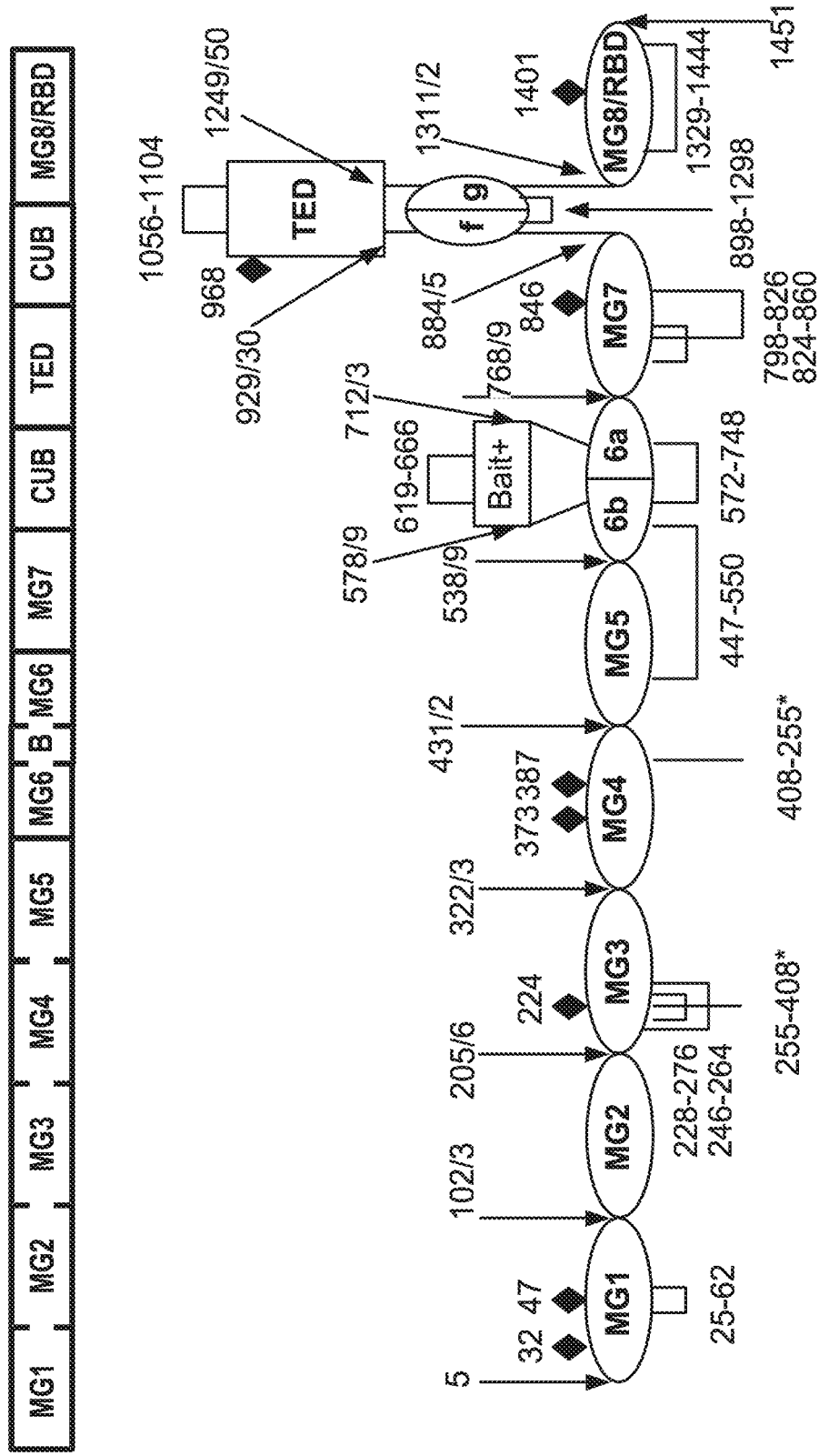
FIG. 4 depicts the A2M structure and various domains of A2M.
Figures 5A, 5B, 5C:
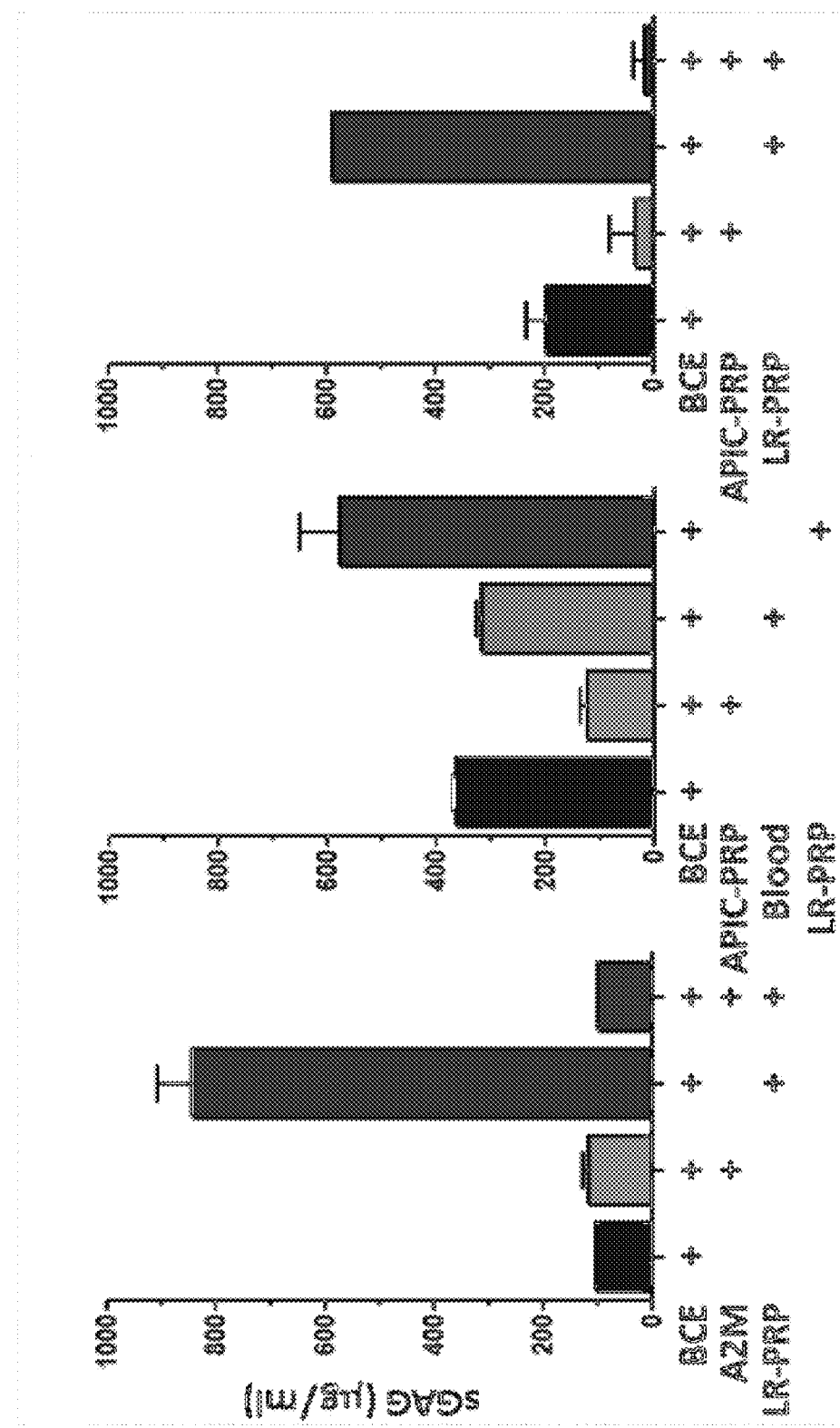
FIG. 5A depicts a graph demonstrating treatment of Bovine Cartilage Explants (BCE) with leukocyte-rich Platelet Rich Plasma (LR-PRP), which induces cartilage catabolism, and treatment with purified A2M to inhibit cartilage degradation.
FIG. 5B depicts a graph demonstrating treatment of Bovine Cartilage Explants (BCE) with APIC-PRP, blood, or leukocyte-rich Platelet Rich Plasma (LR-PRP) from the same patient. LR-PRP, but not blood, induces cartilage catabolism. Treatment of BCE with APIC-PRP inhibits cartilage degradation below endogenous levels.
FIG. 5C depicts a graph demonstrating leukocyte-rich Platelet Rich Plasma (LR-PRP) induces cartilage catabolism in a Bovine Cartilage Explant (BCE) model. Treatment with APIC-PRP inhibits the cartilage degradation induced by treatment with LR-PRP.
Figures 6A, 6B:
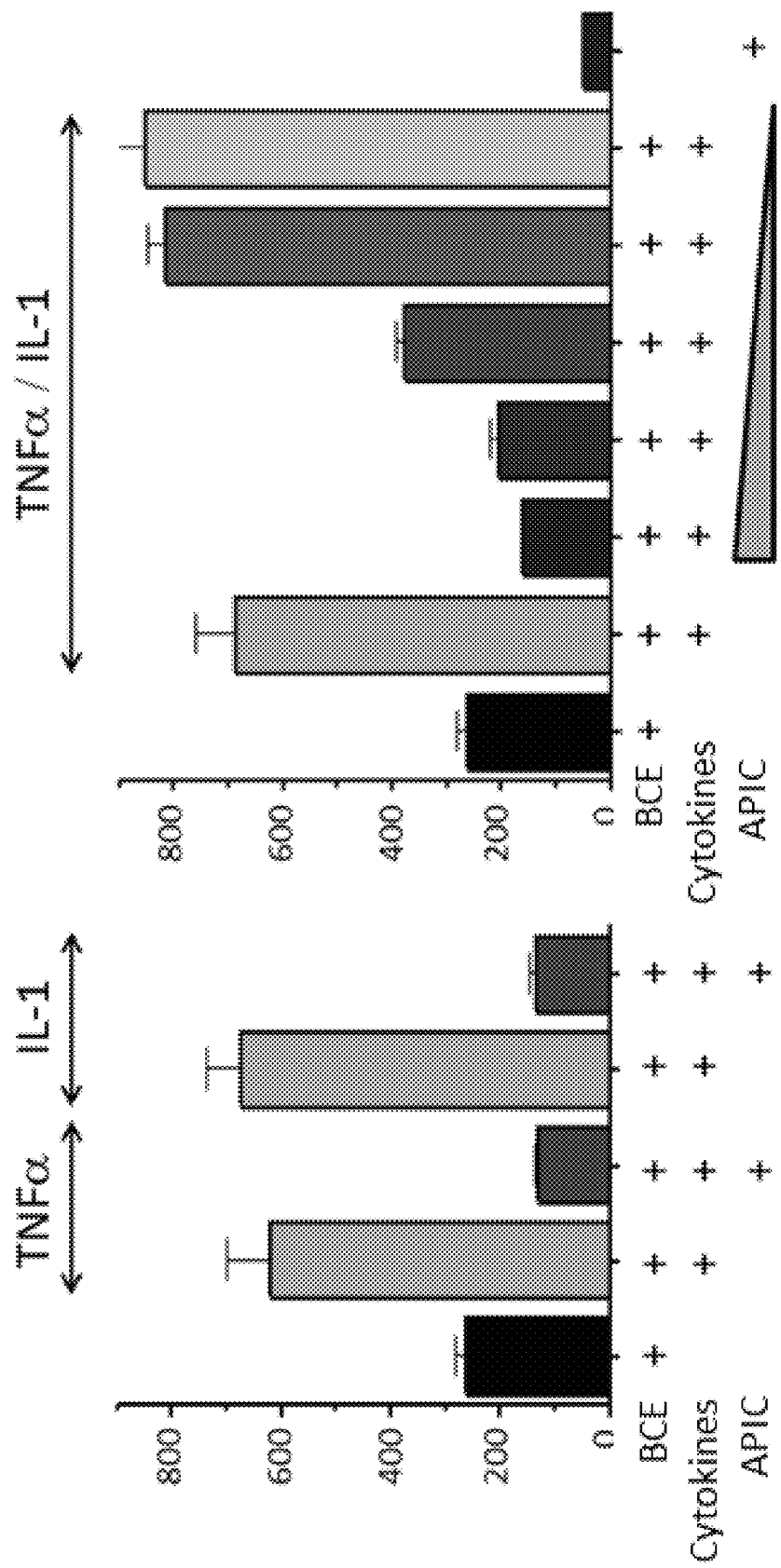
FIG. 6A depicts a graph showing Bovine Cartilage Explants (BCE) treated with pro-inflammatory cytokines TNF-α and IL-1β to induce cartilage catabolism. Cartilage catabolism with each cytokines separately is demonstrated by the release of sulfated Glycosaminoglycans (sGAG) into the culture media. Treatment with APIC-PRP efficiently inhibits cartilage catabolism by each pro-inflammatory cytokine separately.
FIG. 6B depicts a graph showing Bovine Cartilage Explants (BCE) treated with the combination of pro-inflammatory cytokines TNF-α and IL-1β to induce cartilage catabolism. Treatment with APIC-PRP efficiently inhibited cartilage catabolism by the combination of pro-inflammatory cytokines in a dose dependent manner.
Figure 15:
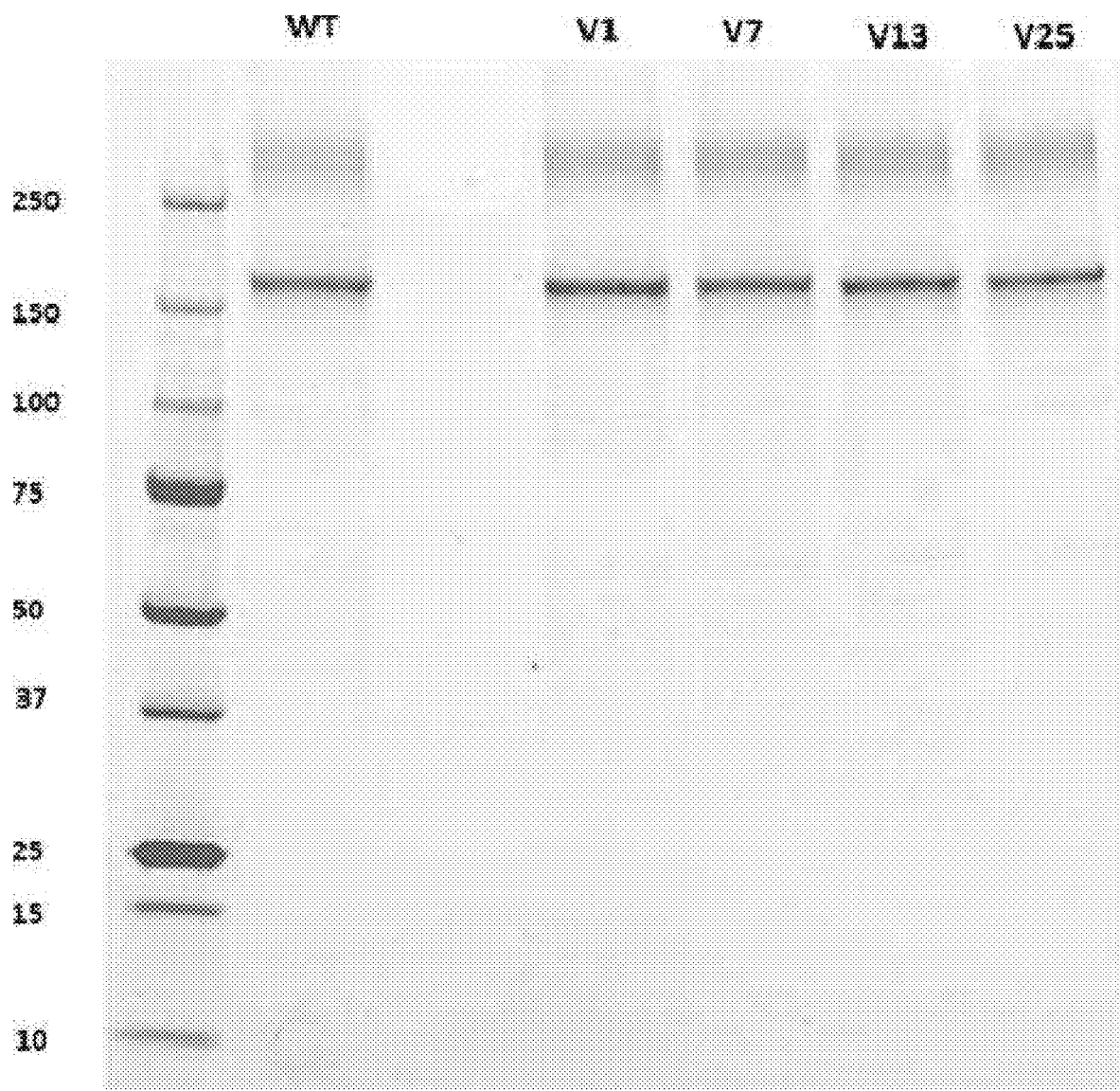
FIG. 15 is a depiction of a pseudocolored stain-free SDS-PAGE gel of a representative purification of tagged wild-type A2M and the four selected variable bait region A2M proteins. The theoretical molecular weight of a monomer of wild-type A2M is 163 KDa, not including glycosylation. The blurry band above 250 KDa is comprised of dimeric A2M that is not thoroughly reduced during sample preparation or covalently bound dimer through amino acid modification mechanisms.
Figure 16:
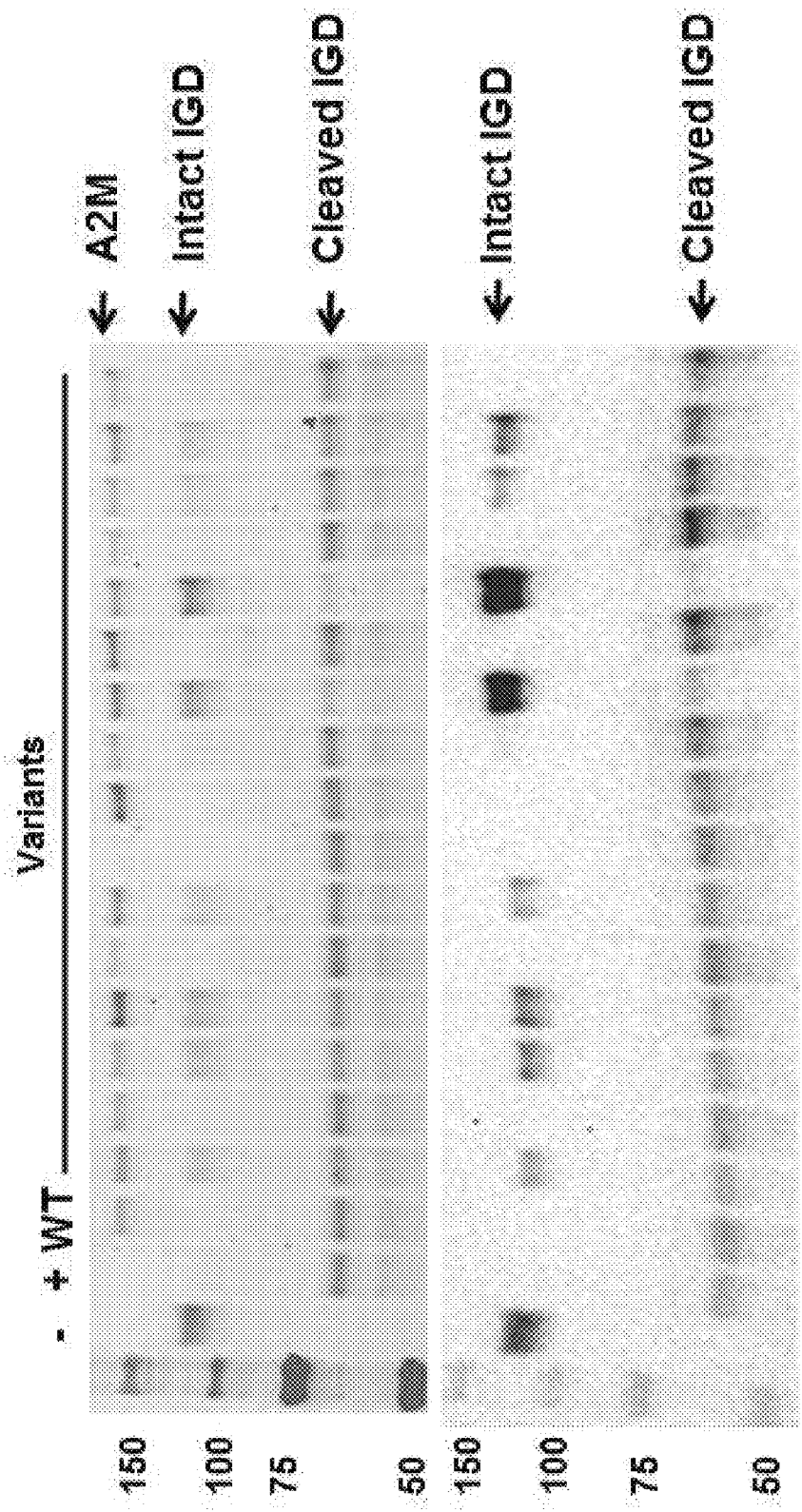
FIG. 16 is a depiction of a pseudocolored stain-free SDS-PAGE gel (top) and Western blot (bottom) of a representative screening assay for inhibition of ADAMTS-5 cleavage of aggrecan IGD domain (IGD fragment) by wild-type (WT) and bait region substituted A2M. The negative control is IGD fragment protein alone; the positive control is IGD fragment plus ADAMTS-5. ADAMTS-5, Wild-type and variant A2M were each kept at 50 nM, and the A2M and ADAMTS-5 were pre-mixed for 10 min. before addition of IGD fragment. The primary antibody for the Western blot was an anti-Aggrecan G1-IGD-G2 polyclonal antibody (R&D).
Figure 17A:
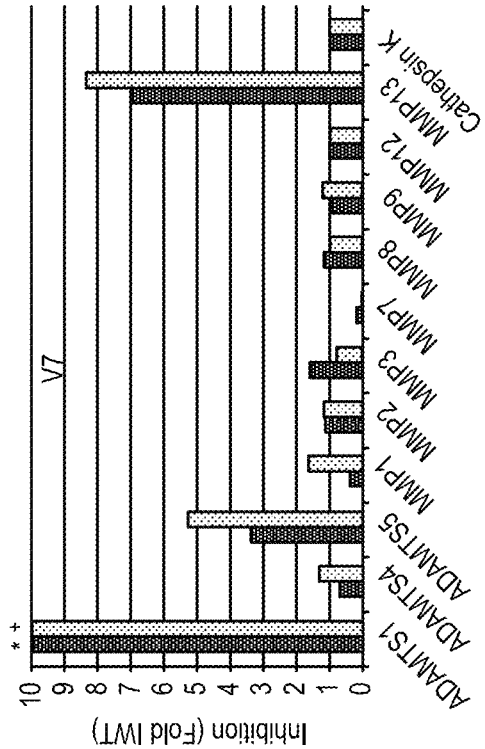
FIG. 17A, FIG. 17B, FIG. 17C, and FIG. 17D are exemplary graphs depicting a comparison of the relative inhibitory characteristics of the four chosen variants vs. various MMPs and ADAMTS-4 and -5 as determined by the two IGD screening experiments. In each case the unit for the y-axis is multiples of the wild-type inhibition of each protease.
Figure 17B:
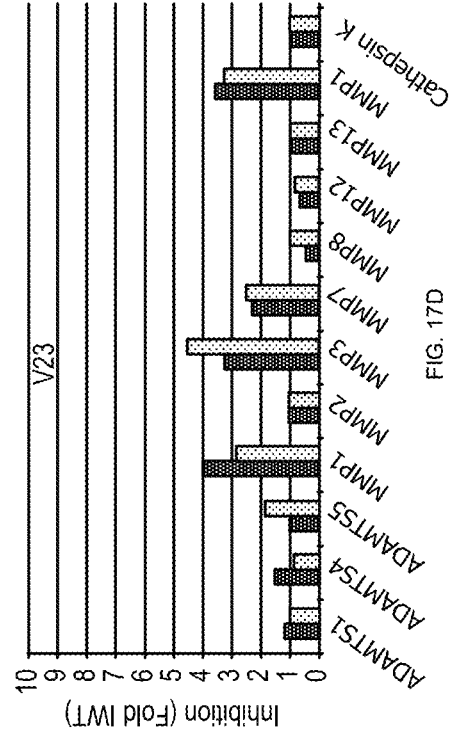
Figure 17C:
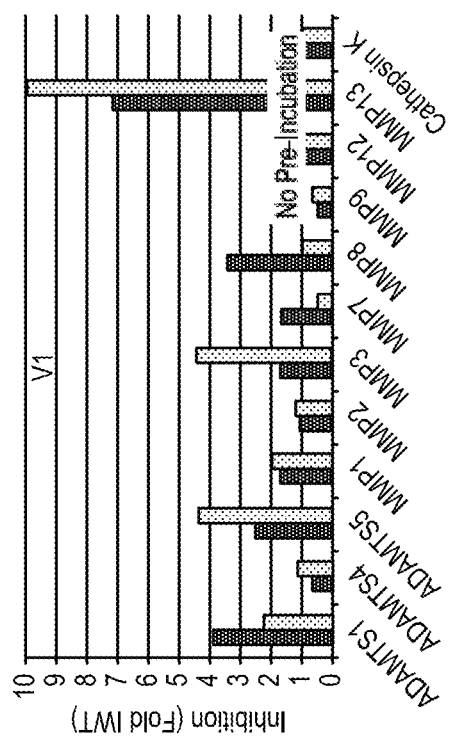
Figure 17D:
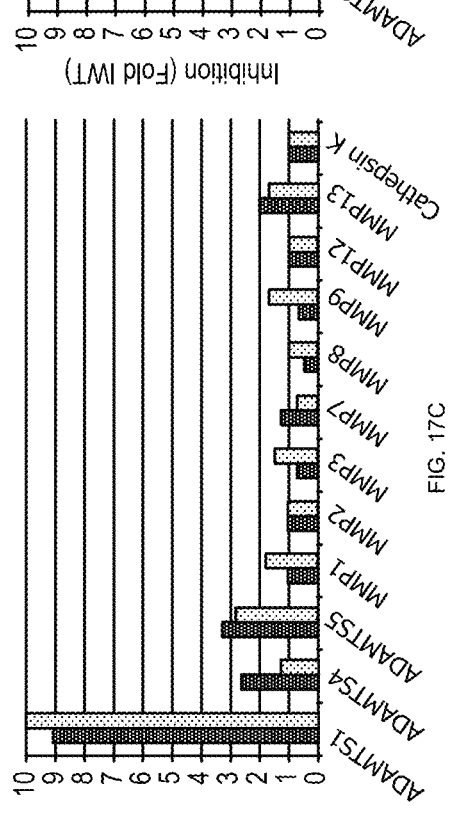

Example 1—Generation and Selection of HEK293 Clones Expressing Recombinant A2M Recombinant A2M wild type sequence was expressed in HEK293F cells. Hek293F cells are plated adherently and allowed to attach overnight. Cells are transfected with XTreme Gene HP (Roche) and DNA in a 6 uL reagent: 2 ug DNA ratio. Cells are grown for 48 hours at 5% CO2 and 37 degrees Celsius. Forty-eight hours after transfection media samples are taken to confirm success of the transfection via an ELISA assay that quantifies A2M protein. Cells are split so as to be in logarithmic growth phase and selection antibiotic (blasticidin) is added at 10 µg/mL (selection concentration determined experimentally). Cells are selected in antibiotic until all of the negative control cells are dead (usually about 4 to 5 days). Another media sample is taken at this point to confirm that this newly established pool is still producing protein. Upon confirmation of protein production cells are plated at a density of ~100 cells/10 cm dish with 7.5 µg/mL blasticidin (maintenance concentration determined experimentally). This plating density is sparse enough that cells will be spaced far enough apart to allow each cell to grow into an individual colony. These colonies are collected using cloning cylinders (Sigma) and plated in a 24 well plate to allow further cell growth. Once cells become confluent in the 24 well plate an ELISA is performed on a media sample again to screen for the highest producing clone. High-expressing clones were selected and used for production of A2M. The chosen clones were expanded and adapted to suspension (FIG. 3). Suspension adaption was completed by slowly changing the media to a serum-free media while the cells are in shaker flasks. Once the culture is in suspension, protein can be collected by simply spinning the cells out of the media. The A2M containing supernatants were subjected to purification for A2M. The higher cell number per volume of media results in a higher protein concentration per milliliter of media. High purity samples were obtained after two chromatography methods. A yield of ~12 mg/L (adherent pool) was typical (FIG. 15).

Figures 7A, 7B:
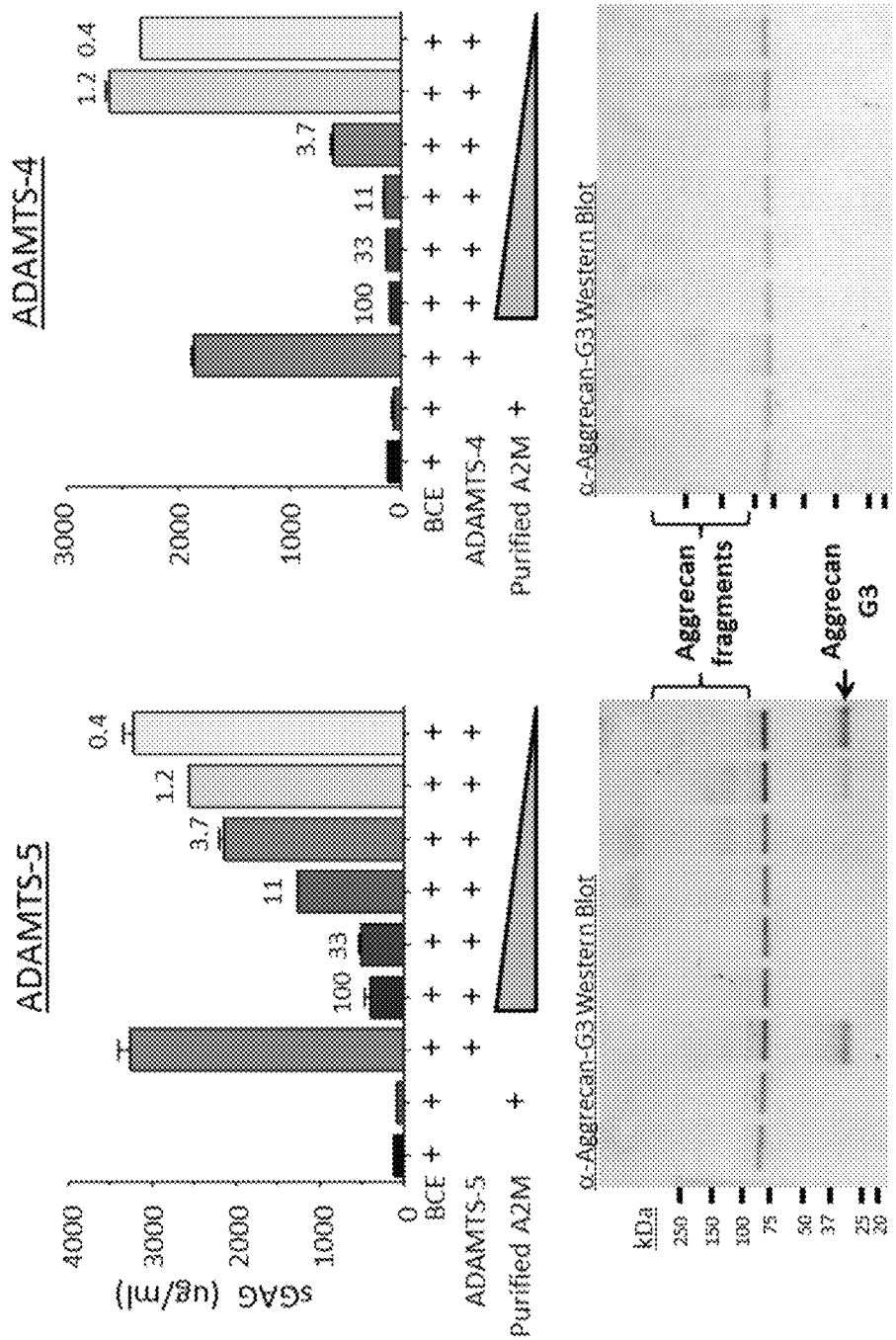
FIG. 7A depicts the sulfated glycosaminoglycan (sGAG) released upon cartilage catabolism in a BCE model with and without treatment of ADAMTS-5 and treatment with or without a serial dilution of purified A2M (top). Western Blots of the samples (bottom) demonstrate ADAMTS-5 degradation of cartilage produced an Aggrecan G3 fragment and higher molecular weight Aggrecan fragments, which were inhibited by treatment with A2M in a dose dependent manner. Values above the columns indicate the concentration of A2M (µg/ml) needed to inhibit ADATMS-5. An 85 kDa non-specific band is also visible, which was apparent in media-only controls (data not shown).
FIG. 7B depicts the sulfated glycosaminoglycan (sGAG) released upon cartilage catabolism in a BCE model with and without treatment of ADAMTS-4 and treatment with or without a serial dilution of purified A2M (top). Western Blot analysis with α-Aggrecan G3 antibody (bottom) of the samples demonstrates ADAMTS-4 degradation of cartilage produced high molecular weight Aggrecan C-terminal fragments containing the G3 domain. Cartilage catabolism is inhibited by A2M in a dose dependent manner and reduces the release of cartilage aggrecan fragments. An 85 kDa non-specific band is also visible, which was apparent in media-only controls (data not shown).

Example 2—Inhibition of ADAMTS-5- and ADAMTS-4-Induced Damage of Cartilage with A2M Bovine Cartilage Explants (BCEs) were treated with 500 ng/ml ADAMTS-5 or ADAMTS-4 for 2 days, with a 3-fold serial dilution of purified A2M (FIGS. 7A, B). Concentration of A2M tested were 100, 33.3, 11.1, 3.7, 1.2, 0.4 µg/mL. The variant A2M inhibited cartilage catabolism in a concentration dependent manner. The $IC_{50}$ for inhibiting 500 ng/ml of ADAMTS-5 was calculated to be ~7 µg/ml A2M (a 1:1 molar ratio). Maximum inhibition was observed in ~90% with 100 µg/ml A2M (a 14:1 molar ratio). The A2M was shown to block formation of Aggrecan G3 fragments (FIGS. 7A, B) and FAC formation (FIGS. 9A-9F).

Example 3—Comparison of APIC Retentate and Filtrate

Fresh cartilage was treated with APIC containing ~7 mg/ml A2M. Cartilage catabolism was efficiently blocked by 1% v/v of the Retentate of the APIC production process (concentration of proteins >500 kDa in size), but not by the Filtrate (contains proteins <500 kDa), even at 5% v/v (FIGS. 10A and 10B). The chondroprotective effects of APIC were dose dependent. The inability of Filtrate to protect cartilage from catabolism by ADAMTS-5 demonstrates that APIC concentrates >99% of the protective factors of autologous blood.

Example 4—A2M Inhibition of Cartilage Catabolism in an Osteoarthritis Model

Fresh cartilage was treated with TNF-α or IL-1βeta to induce chondrocytes to secrete proteases, similar to the pathology of osteoarthritis. Cartilage catabolism is detected as increased sulfated glycosaminoglycans (sGAG) in the culture media. Treatment with pro-inflammatory cytokines induces cartilage catabolism which treatment with variant A2M polypeptides block in a dose-dependent manner.

Example 5—Cytokine Profile of Monocytes Treated with Variant A2M

Figure 11:
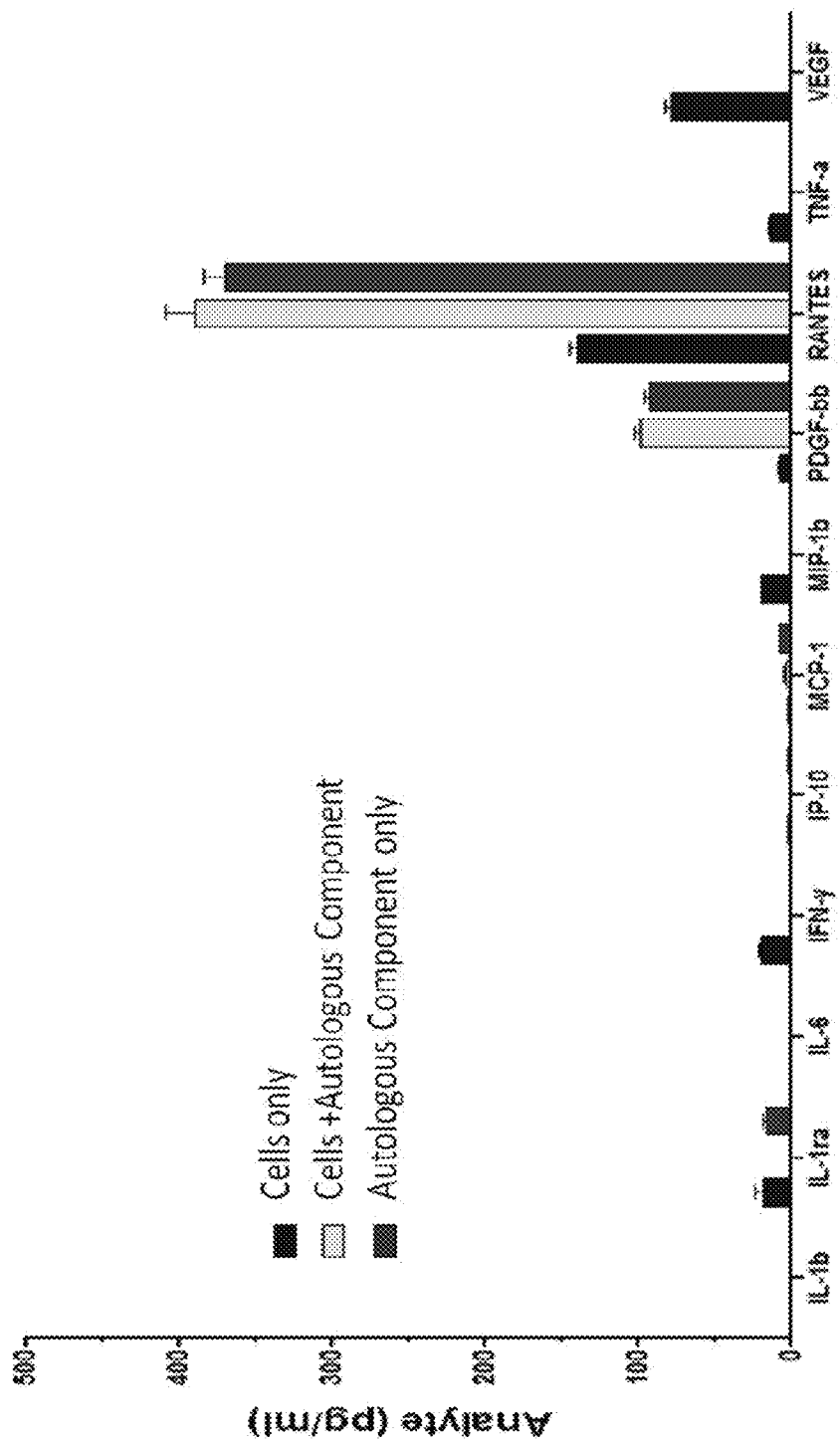
FIG. 11 is a bar graph depicting the effects of treatment of THP-1 monocytes with variant A2M for two days in culture. No activation of the monocytes was observed through monitoring with a panel of cytokines, chemokines, and growth factors (Left to right: IL-1β, IL-1 receptor agonist (IL-1ra), IL-6, IFN-γ, IP-10, MCP-10, MIP-1β, PDGF-ββ, RANTES, TNF-α, and VEGF).

THP-1 monocyte cells were treated with or without variant A2M for 2 days and the activation of the cells was monitored by secretion of cytokines and growth factors into the medium. THP-1 did not show a change in the cytokines profile tested (FIG. 11). Similar results were seen in E6-1 T-cells and SW982 fibroblast cells.

Example 6—Design and Synthesis of Tagged Wild-Type A2M Expression Construct

A DNA sequence coding for the wild-type A2M precursor protein (SEQ ID NO. 1) was synthesized by GenScript based on the RefSeq amino acid sequence of human A2M precursor protein (RefSeq #NP_000005.2) (SEQ ID NO. 3). The codons used in the construct were optimized by GenScript for mammalian codon usage bias, GC content, CpG dinucleotide content, mRNA secondary structure, cryptic splicing sites, premature polyadenylation sites, internal chi and ribosome binding sites, negative CpG islands, RNA instability motifs, repeat sequences, and restriction endonuclease sites.

A sequence encoding a fusion tag (DYKDDDDK-GASHHHHHH) was added to the natural end of the protein sequence, followed by a STOP codon. The expression construct was given a Kpn1 restriction site at the 5' end and a BamH1 restriction site at the 3' end. This construct was cloned into a pUC57 vector. The insert encoding the expression construct was extracted from the pUC57 vector via double digestion with Kpn1 and BamH1 followed by agarose gel electrophoresis and gel extraction of the fragment. This insert was ligated into a pJ608 mammalian expression vector (DNA 2.0) behind a cytomegalovirus (CMV) promoter (FIG. 23) and transformed into E. coli strain GC10 (Genessee Scientific). This step is performed to maintain and propagate the vector. The sequence of the expression construct was verified by DNA sequencing (Genewiz).

Example 7—Design of Acceptor Construct for Variable Bait Regions

The wild-type expression construct was mutated to allow switching of bait region sequences by first introducing XhoI and HindIII restriction sites flanking the sequence encoding the bait region. This was done via two sequential site-directed mutagenesis reactions using the wild-type expression construct as the template. The sequence of the mutant "acceptor" construct was verified by DNA sequencing of the bait region by Genewiz (SEQ ID NO 2). The corresponding amino acid sequence is SEQ ID No 4. The mutations in the DNA sequence necessarily result in three amino acid substitutions in the protein Q693E on the N-terminal side of the bait region and T730K and V731L on the C-terminal of the bait region. These mutations could not be avoided because the natural DNA sequence does not have restriction endonuclease sites that could be used to remove the bait sequence. These mutations are included in the new bait regions design. The preservation of function of the acceptor mutant was verified by its ability to inhibit trypsin (see below), and it was tested versus other proteases as part of the evaluation of the designed bait regions.

Example 8—Design and Creation of Variable Bait Region Expression Constructs

Novel variant bait region sequences (SEQ ID NOs: 6-30) and variant bait regions comprising one or more protease recognition sequences (SEQ ID NOs 31-83) were designed based on the known cleavage sites of human aggrecan by ADAMTS-4, ADAMTS-5, various MMPs, and other proteases (Fosang et al., Eur. Cells and Mat., Vol. 15, 2008, pp. 11-26) (Table 1). Some constructs retained part or the entirety of the wild-type A2M bait sequence, but with an insertion of non-native amino acid sequences including the variant bait regions of SEQ ID NOs: 6-30 and variant bait regions comprising one or more protease recognition sequences of SEQ ID NOs 31-83. Several pUC57 plasmids, each containing DNA insert sequences encoding between one and six bait region sequences, were synthesized by GenScript and delivered to us as a lyophilized powder. Each insert sequence contains an XhoI site at the 5' end and a HindIII site at the 3' end for ligation into the acceptor construct. Each insert plasmid, along with the acceptor plasmid, was reconstituted in water and double digested overnight with 20 U of XhoI and HindIII to liberate the insert sequences, and the digested plasmids were separated by electrophoresis on a 1% agarose gel and visualized under UV light. Bands corresponding to the insert and acceptor length were extracted from the gel via a Qiagen Qiaquick Gel Extraction Kit as per the kit instructions. The concentration of DNA obtained from each extraction was determined using a Qubit fluorimeter (Invitrogen). Ligation of inserts into the region of the acceptor encoding the bait region was undertaken in a semi-random fashion, by mixing the extracted insert fragment(s) from each insert vector digestion with 50 ng of digested acceptor plasmid in a 3:1 molar ratio of insert:plasmid. Ligation was achieved using a Quick Ligation kit (New England Biolabs) according to the kit instructions. The mixture of ligated plasmids was then transformed into E. coli strain GC10 (Genessee Scientific) and spread onto Luria broth/agar plates containing 100 mg/mL ampicillin to generate single colonies of transformants. 5 mL Luria broth cultures of individual colonies from each ligation reaction were grown and the plasmid DNA contained within each extracted via a Qiagen QiaPrep miniprep kit according to the kit instructions. These plasmids were sent to Genewiz for sequence confirmation using a primer that anneals to the sequence of the A2M construct just upstream of the bait region. The individual chromatogram traces were analyzed for the presence of heterogeneity in the sequence, and the sequences of the individual inserts confirmed.

Example 9—Expression of A2M Variants

A2M variants were expressed in HEK293F cells (Gibco) by transient transfection of each construct in suspension cells. Cells were grown to a density of 550,000 cells/mL in a Erlenmeyer cell culture flask containing 20 mL of FreeStyle F17 medium (Invitrogen) containing 1× GlutaMax (Gibco) on a rotator at a speed of 125 rpm inside a 37° C. incubator containing an 8% CO2/air mixture. Cells were transfected by mixing 20 µg of plasmid DNA of each construct (wild-type or variant) in a 1:2 (w/v) ratio with TransIT Pro plus 10 µL TransIT Boost (Mirus) 15 minutes before addition to media. Cells were maintained in the same conditions for three days after transfection before the media containing secreted recombinant protein was removed for protein purification (FIG. 3).

Example 10—Purification of A2M Variants

Since the A2M expression construct encodes the precursor A2M protein, the expressed and processed recombinant protein is secreted into the cell culture medium via the natural A2M secretion signal. Secreted recombinant wild-type A2M and A2M bait region variants were purified from the transfected cell culture media by Immobilized Metal Affinity Chromatography using the 6× His tag at the C-terminus of each construct. The media removed from the transfected cells was centrifuged at 17,500 G for 15 minutes to remove all cells. Imidazole was added to the clarified media to a final concentration of 10 mM. 1 mL of HisPur Cobalt resin slurry (Pierce) was added to the sample and allowed to equilibrate with shaking on a rocker at 4° C. for one hour. The beads were collected by centrifugation at 700 G for 2 minutes and the supernatant discarded. The beads were washed three times in 10 mL of a buffer of 50 mM Tris-Cl, 150 mM NaCl, 10 mM imidazole, pH 7.4, each time the beads were collected by centrifugation at 700 G, and the supernatant removed and discarded. The protein was eluted by mixing of 2 mL of elution buffer (wash buffer containing 200 mM imidazole) with the beads and centrifuging for 2 minutes at 700 G. The supernatant was collected and retained, and the elution repeated a total of three times. The purified proteins contained in the sample were then concentrated to 100 µL volume (typically between 100 mg/mL and 600 mg/mL) using an Amicon spin filter with a NMCO of 100 KDa. During concentration the imidazole containing buffer was exhaustively exchanged for 50 mM HEPES, 150 mM NaCl, 10 mM $CaCl_2$, 100 µm $ZnCl_2$, 0.05% (w/v) Brij-35, pH 7.4 (HNZCB buffer). The concentration of the protein was determined using BCA (Pierce) and 660 nm (Pierce) assays. 1 µg of each purified protein was mixed with reducing SDS-PAGE loading buffer, heated for five minutes at 95° C., and loaded onto a 7.5% Tris-glycine SDS-PAGE stain-free gel (Bio-rad). The gel was developed by exposing to UV light for five minutes, and a picture taken of the total protein bands. The purity of the recombinant A2M was estimated to be consistently greater than 90% across all variants and wild-type proteins (FIG. 15).

Example 11—Screening Increased Protease Inhibition by A2M Variants

Wild-type A2M protein and A2M variant polypeptides, including A2M variants containing the bait regions of SEQ ID NOs: 6-30 containing one or more protease recognition sites of SEQ ID NOs 31-83, were screened for their comparative ability to inhibit proteolysis of a recombinant IDG fragment of human aggrecan which consist of the G1, G2, and interglobular domains (R&D) by ADAMTS-4, ADAMTS-5, and MMP13. Screening the effectiveness of variants for the inhibition of each of these enzymes was done in the same manner taking in consideration the rate of the proteolytic activity of each protease, such as those in Tables 3, 4a and 4b. The amount of IGD fragment in each sample was held constant at 0.1 µg, whereas the amount of protease varied depending on the activity of the protease toward IGD fragment. Since each of the variants and wild-type A2M vary greatly in the kinetics of bind to each protease, some showed complete inhibition with no pre-incubation of A2M with the protease, where others showed some inhibition if incubated with the protease for 10 minutes, and others showed no inhibition even after a pre-incubation of A2M with the protease. Two independent assays were performed on each A2M variant: one in which the protease, IGD fragment, and A2M were all added at the same time (no pre-incubation), and one in which the protease and A2M were pre-incubated at room temperature for ten minutes before addition of the IGD fragment, in order to detect slower inhibitors binding to the proteases. For the experiment with no pre-incubation of protease with A2M, 5 µL of 150 nM tagged wild-type A2M or an A2M variant in HNZCB buffer was added to a microcentrifuge tube. 5 µL of 40 mg/mL IGD fragment was then added to the same tube and mixed. Finally 5 µL of 150 nM (ADAMTS-4 and ADAMTS-5, a 1:1 A2M:protease molar ratio) or 75 nM (MMP13—a 2:1 A2M:protease molar ratio) protease was added to the tube. For the experiment with a 10 minute pre-incubation, 5 µL of each A2M was mixed with 5 µL of protease 10 minutes before addition of 5 µL of IGD fragment. All samples were incubated at 37° C. for one hour before being stopped by addition of 2× reducing SDS-PAGE loading buffer (Bio-rad) and heating for 5 min. at 95° C. 15 µL of each sample was loaded onto a 7.5% Tris-Glycine Stain Free Gel (Bio-Rad) and run at 150 V for 1 hour. Total protein was visualized and imaged under UV light as per gel instructions. The proteins were then blotted onto a nitrocellulose membrane via an iBlot (Invitrogen) dry blotting system using a transfer time of seven minutes, blocked for one hour using TBS casein blocking solution (Bio-rad), and probed using an anti-IGD fragment goat polyclonal antibody (R&D Biosystems catalog #AF1220) at a concentration of 0.1 mg/mL in TBS-T. The blot was washed three times with TBS-T and probed with an HRP-conjugated anti-goat IgG polyclonal antibody (Sigma catalog #A5420) at 0.1 mg/mL in casein blocking solution. The blots were developed using ECL Plus chemiluminescence kits (Pierce) according to the manufacturer instructions. The Western blots were imaged in a ChemiDoc imager system (Bio-rad). Each IGD fragment band on the Western (intact and degraded IGD fragment) was quantified using ImageLab software. The amount of degradation of IGD fragment in the presence of each A2M variant was quantified by comparing the intensities of the degraded and intact IGD fragment bands (FIGS. 16-20), and the inhibitory capacity of each variant was compared to a wild-type A2M sample that was prepared along with each batch of variants. From this initial round of screening, eight variants were selected for further screening against MMP1, MMP2, MMP3, MMP8, MMP9, MMP12, and Cathepsin K (all enzymes are recombinant human constructs and purchased from R&D) and others, such as those in Tables, 4a, and 4b. The comparison of the inhibitory capacity of each variant was done by taking the ratio of the intensity of the degraded band to the intact band with the exception of MMP9 and MMP13 which degraded IGD fragment in such a manner that cleaved fragments did not appear on the Western blot. In these cases the comparison was done based solely on the intensity of the remaining intact IGD fragment band. Additionally, ADAMTS-1 and MMP7 only cleaved the IGD fragment perceptibly; therefore, accurate inhibition measurements could not be quantified. In these cases all of the variants were judged to be essentially equivalent to wild-type with respect to these two proteases. After evaluating all inhibition data, four variants were selected based on improved or at least equivalent inhibition characteristics against all proteases tested (FIGS. 17-21) or a mixture of proteases known to degrade cartilage (FIG. 22).

Example 12—Screening of A2M Variants Vs. Proteases

To verify that the four selected A2M variants are still capable of inhibiting the general proteases trypsin and chymotrypsin to a similar degree as the wild-type protein, the variants were tested in a fluorescent proteolysis assay (Twining, S. S., *Anal. Biochem*. Vol. 143, 1984, pp. 30-34). In this assay, one monitors the increase in fluorescence emission from a FITC-labeled protein substrate that is caused by a proteolysis-dependent release of the fluorophore. Two experiments were done on each variant: one in which the molar ratio of A2M:protease is held at 1:1, and another in which the A2M is reduced to 0.5:1. 40 µL of wild-type or variant A2M at a concentration of 100 nM (for the 1:1 ratio) or 50 nM (for the 0.5:1 ratio) in HNZCB buffer was mixed with 100 µL of bovine trypsin (Sigma) at 40 nM and incubated at room temp for 5 minutes. Into this mixture 70 µL of 40 µg/mL FTC-casein substrate (Pierce) was added, mixed, and immediately pipetted into three wells of a 384 well plate (65 µL/well) The plate was placed into a Cary Eclipse fluorimeter and read in kinetic mode (single wavelength) with excitation wavelength of 485 nm and emission wavelengths of 519 nm for fifteen minutes, during which time the rate of casein degradation by the protease remains approximately linear. The emission intensity was averaged for the three sample wells, plotted vs. time, and a straight line fitted to the data from each sample and control (FIGS. 18A and 18C). The slope of the fitted line was taken as a measure of the protease activity remaining in solution.

Comparison of the four chosen A2M variants to the wild-type protein shows that the variants are all capable of inhibiting various proteases, including trypsin and chymotrypsin approximately equally, to the wild-type A2M (FIGS. 18B and 18D).

Example 13—Preparation of Blood for Autologous Therapy 120 mL of whole human blood was obtained from a subject by venipuncture. 38 mL aliquots of the blood were collected into two or more hematologic collection bottles with a suitable volume of citrate dextrose solution A ("ACD-A") in each collection bottle. The collection bottles with blood/ACD-A were placed into a fixed angle rotor centrifuge, and centrifuged at predetermined velocities and times under ambient temperature conditions. Approximately 15 mL of plasma was aliquoted from each tube with a serological pipette, leaving approximately 1 mL, of plasma above the level of the buffy coat so as not to disturb the precipitated cells. This process was repeated for the collection bottles in one or more centrifuge spin cycles to yield a volume 45 mL of total plasma from a total blood draw of 120 mL. The plasma was pooled into a separate sterile hematologic collection bag. The compositions described herein can be mixed with autograft or allograft tissue, such as bone, before administration to a subject.

Example 14—In Vitro Cartilage Degradation Assay

To test the hypotheses that cartilage catabolism caused by proinflammatory cytokines and cartilage-degrading metalloproteinases (ADAMTS) can be inhibited by preparations of Leukocyte-rich PRP (LR-PRP) or Autologous Platelet Integrated Concentrate (APIC-PRP) a controlled in vitro cartilage degradation assay was performed. BCE was treated with ADAMTS-5, TNF-α or IL-1β in the presence or absence of LR-PRP or APIC-PRP. Cartilage catabolism was measured following 2 or 3 days in culture by proteoglycan release via the presence of sulfated glycosaminoglycan (sGAG) in the media. Bovine articular cartilage explants (BCE, 200 tit mg) were isolated from 1-1.5 year-old heifers and are equilibrated 3 days in culture. BCE cultures were treated for 3 days with or without a 33% (v/v) Leukocyte rich platelet-rich Plasma (LR-PRP), or APIC-PRP prepared from the same patient. Protease digestion of cartilage with 500 ng/ml ADAMTS-5 for 2 days was inhibited with a 2-fold serial dilution of APIC-PRP [$ED_{50}$=0.1% v/v]. For cytokine-induced cartilage catabolism, BCE was incubated 3 days in SFM with or without 80 ng/ml human TNF-α or 8 ng/ml human IL-1β. Cartilage degradation was inhibited with the addition of 5 mg/ml A2M or 30% (v/v) APIC-PRP. To demonstrate a dose-response curve of APIC-PRP, 3-fold serial dilutions of APIC-PRP [ED50=3% v/v] were used to inhibit TNF-α/1L-1p induced cartilage degradation. Cartilage catabolism was measured in culture supernatant by proteoglycan release via the presence of sulfated glycosaminoglycan (sGAG) using a DMMB assay with chondroitin sulphate standard curve. Cartilage degradation in 200 mg BCE was induced by addition of LR-PRP (33% v/v), demonstrating it as a source of cartilage catabolism. Treatment with proinflammatory cytokines (80 ngiml TNF-α or 8 ng/ml IL-1β), ADAMTS-5 (500 ng/ml) also resulted in increased sGAG in the medium. Addition of APIC-PRP inhibited cartilage catabolism induced by cytokines, metalloproteinases or LR-PRP in a dose dependent manner. The addition of LR-PRP at the highest concentration used in the APIC-PRP study reduced but did not inhibit cartilage catabolism induced by cytokines or MMP's measured by the release of sGAG in the medium (data not shown). Osteoarthritis (OA) is characterized by progressive degeneration of articular cartilage. The BCE model is representative of studying putative therapeutics in OA. This study demonstrates that Leukocyte-rich PRP (LR-PRP) contributed to cartilage catabolism, but APIC-PRP protected cartilage from degradation by known OA mediators. This activity can be explained by the 5-10 fold increased concentration of A2M in APIC-PRP over its concentration in blood. This conclusion is in agreement with experiments that demonstrate the protective effect of A2M on cartilage. This improved understanding of cartilage biology and metabolism should lead to clinical trials of APIC-PRP in humans.

Example 15—Chondroprotective Effect in Rabbit Model

The pathology ad osteoarthritis involves the upregulation of inflammatory mediators and preleases such as matrix metalloproteases (MMPs) A2M is a naturally occurring plasma glycoprotein that is a potent protease inhibitor. A2M is behaved to modulate cartilage catabolism by its ability to bind, trap and clear MMPs. Though A2M functions throughout multiple tissues and extracellular spaces, it does not normally reach high levels within the intrarticular joint space. The ability of the Autologous Protease Inhibitor Concentrate (APIC-Cell Free), which concentrates A2M from the blood, was tested to inhibit cartilage catabolism, and thereby attenuate the development of osteoarthritis in a ACL-T rabbit model. The rabbit model represents a functional load-bearing in vivo anatomical model for the evaluation of osteoarthritis, which exhibits mechanical properties, morphological structures, and healing capacity similar to human tissues. Female 8-12 months old New Zealand white rabbits were used in this study. This rabbit model represents a functional load-bearing in vivo anatomical model for the evaluation of osteoarthritis which exhibits mechanical properties, morphological structures and healing capacity similar to human tissue. Multiple Injection Cohort (Group 1): 6 rabbits received ACL-T surgery on the right knee and sham surgery on the left knee. Four injections of 0.3 mL Autologous Protease Inhibitor Concentrate (APIC-Cell Free) were prepared from the rabbit blood and were administered on day 1, 4, 14, and 28 following the ACL knee injury. Rabbits received an equivalent volume of the sterile isotonic saline in the contra-lateral control knee. The rabbits were monitored for 6 weeks, then sacrificed for cartilage degeneration assessment. Control Group (Group 2): 6 rabbits received ACL-T surgery on the right knee without sham surgery on the left knee. These rabbits were the control group and accordingly did not receive any treatment.

Variant A2M Preparation

Prior to the ACL injury, variant A2M polypeptides were prepared. Every rabbit received the protease inhibitor concentrate. Six weeks after the ACL-T operation the animal was sacrificed for macroscopic and microscopic knee joint cartilage evaluation to determine OA progression.

Macroscopic and Histological Analyses

Figure 12:
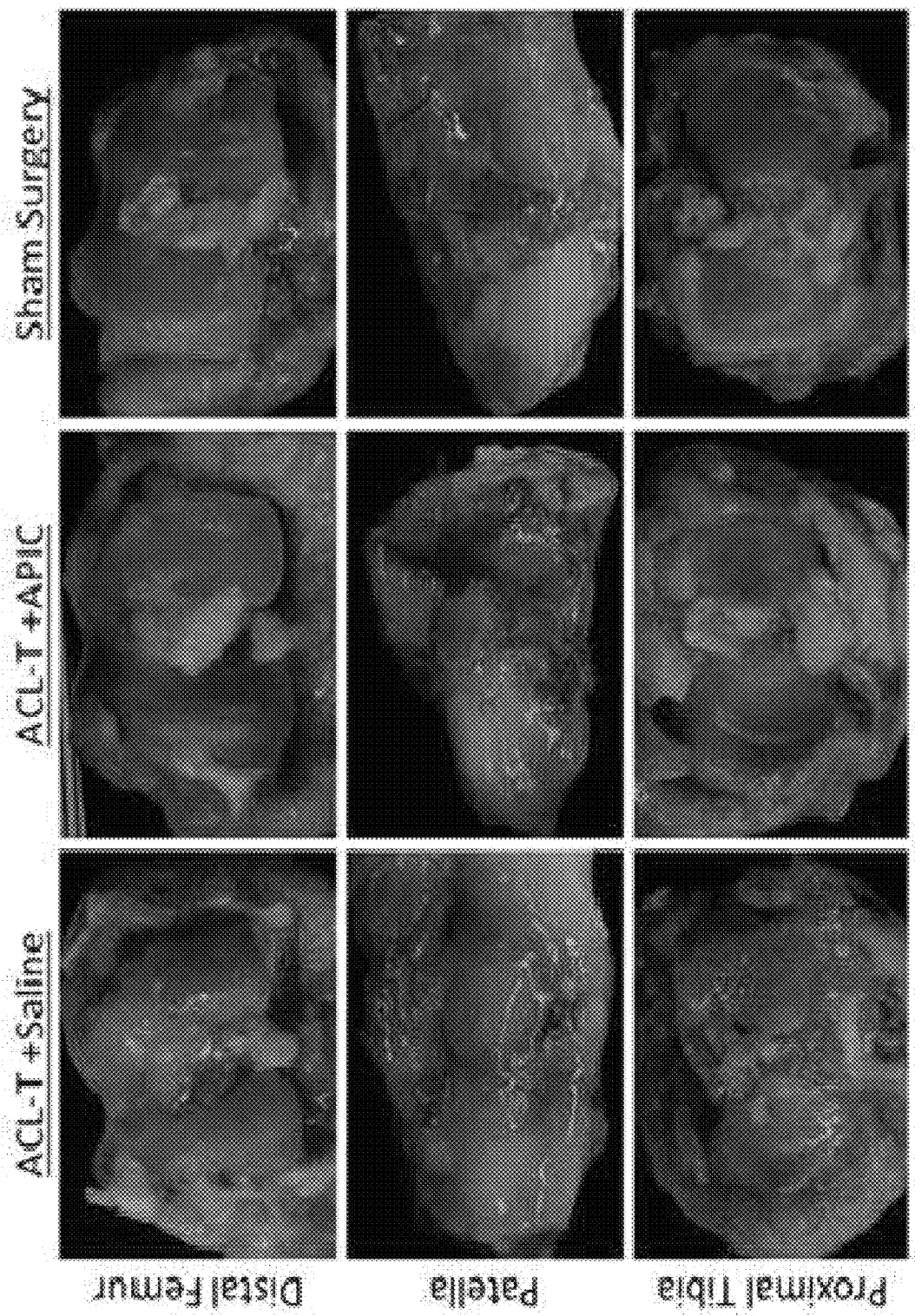
FIG. 12 depicts macroscopic images of rabbit knees 6 weeks after ACL-T surgery and treatment with saline or APIC cell free. Sham surgeries without ACL-T were performed as a control.
Figures 13A, 13B:
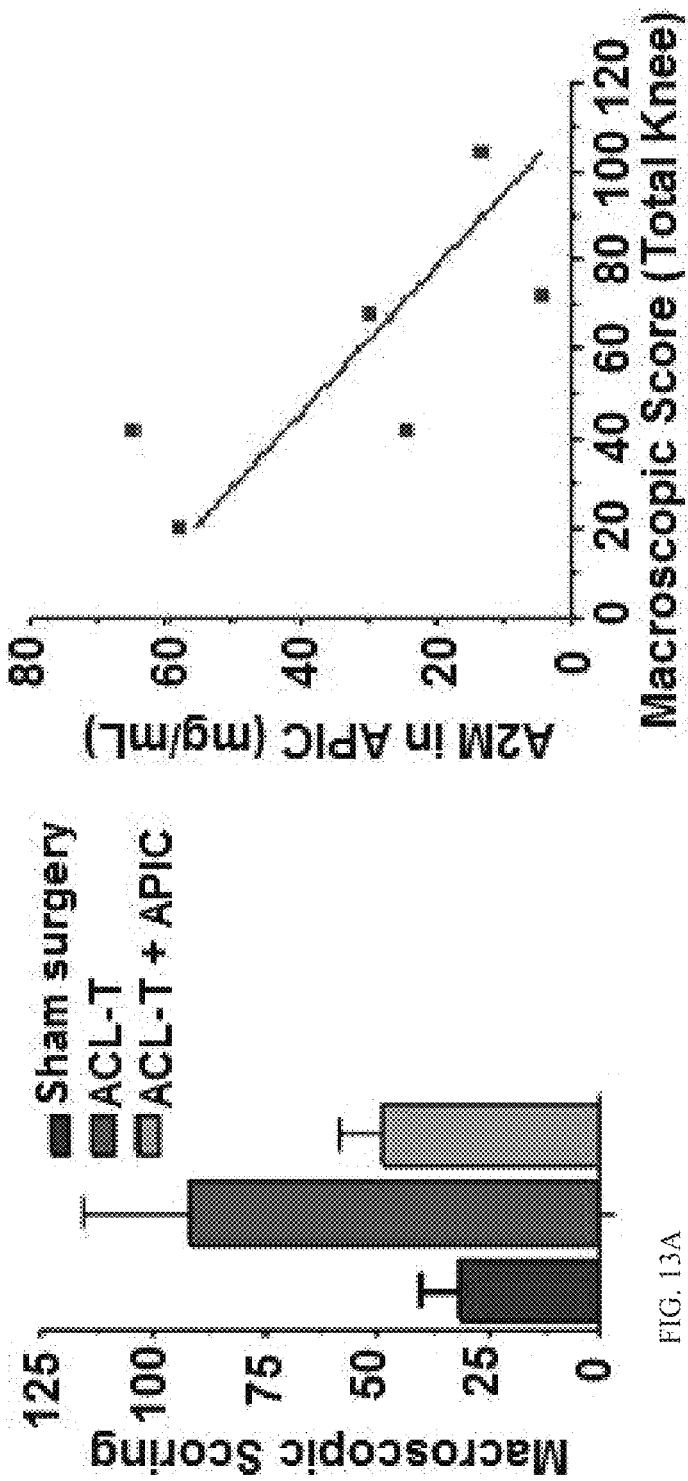
FIG. 13A depicts a graph of macroscopic evaluation for the experiments shown in FIG. 12. The values shown are the average of the macroscopic evaluation of 6 rabbits.
FIG. 13B depicts a graph of macroscopic evaluation, showing an inverse correlation of A2M in APIC cell free treatment and cartilage degradation for the experiments shown in FIG. 12.

For macroscopic evaluation, the distal femoral condyles and tibial plateau surfaces were analyzed and lesions were classified using a validated 0 to 8 scale as previously described. The locations of the lesions in the joint were recorded by a specific nine-area grid of each joint surface, following the classification of the International Cartilage Repair Society (OARSI), which was adapted to the rabbit knee by Lindhorst et al. After macroscopic examination. Isolated femoral and tibial samples were feed and decalcified for histological (microscopic evaluation). Macroscopic evaluation of the femur and tibia demonstrated features consistent with cartage catabolism consistent with OA. Treatment with APIC Cell Free considerably improved cartilage appearance, similar to the sham surgery control (FIGS. 12-14). Application of APIC reduced cartilage degradation by 53+/−20% compared to untreated controls (mean±SEM. p=0.0086) (FIGS. 13A and 13B). The concentration of the variant A2M was determined. There was a dose-dependent correlation between higher concentrations of A2M in and decreased OARSI total knee score on the macroscopic evaluation (FIGS. 13A and 13B). There was also a dose-dependent therapeutic benefit to treatment observed in sum OARSI histopathology evaluations of Safarin-O staining ($r^2$=0.73), Structure ($r^2$=0.76), Chondrocyte density ($r^2$=0.50), and Cluster Formation ($r^2$=0.97) (FIGS. 14A-14D). The data suggests that the Autologous Protease inhibitor Concentrate (APIC-Cell Free), which contains 9-10 times the A2M concentration in blood, has a chondroprotective effect on an osteoarthritis rabbit model.

Example 16—Effect of A2M on BCEs

To test the hypothesis that the addition of proinflammatory cytokines or cartilage-degrading metalloproteinases (ADAMTS and MMP) stimulate cartilage degradation that will be inhibited by A2M, a controlled in vitro cartilage degradation assay was performed. Bovine Cartilage Explants (BCE) were treated with or without proinflammatory cytokines (TNF-α or IL-1β) or cartilage-degrading metalloproteinases (ADAMTS-5, ADAMTS-4, MMP-7, or MMP-12) in the presence or absence of purified A2M.

Bovine articular cartilage explants (BCE. 100±4 mg) were isolated from 1-1.5 year-old heifers and were equilibrated 3 days in culture. To degrade cartilage by protease digestions, BCE was incubated 2 days in Serum-free Media (SFM) with or without 500 ng/mL ADAMTS-4 or ADAMTS-5 and 3-5 µg/mL of MMP-3, MMP-7, MMP-12, or MMP-13. MMP-3 was activated with chymotrypsin before application on BCE. For cytokine-induced cartilage catabolism, BCE (200+/−4 mg) was incubated 3 days in SFM with or without 80 ng/ml human TNF-α and 8 ng/mL human 1L-1β. Cartilage degradation was inhibited with the addition of 100 µg/mL of purified human A2M for protease digestion or 5 mg/mL A2M for cytokine-induced degradation.

Cartilage catabolism was measured in culture supernatant by 1) proteoglycan release via the presence of sulfated glycosaminoglycan (sGAG) and 2) the presence of cartilage proteoglycan fragments by Bio-Rad Stainless SDS-PAGE and Aggrecan G3 fragments by Western blotting.

Fibronectin and Aggrecan Complexes (FAC) were formed by combining degraded cartilage matrix proteoglycans from the BCE experiments with Fibronectin and Synovial Fluid and incubating for 4 hours. Newly formed FAC was measured by the FACT ELI SA, with the alteration of using an α-Aggrecan G3 antibody needed to recognize bovine aggrecan.

The $IC_{50}$ needed to inhibit cartilage catabolism by 500 mg/mL proteases was 7 µg/mL A2M for ADAMTS-5 and 3 µg/mL for ADAMTS-4. Addition of 5 mg/mL A2M also inhibited cartilage catabolism induced by TNF-α or IL-1β. Further, A2M blocked production of Aggrecan G3 fragments, which form complexes with fibronectin and are a marker for pain and degrading joints. (FIGS. 7-10).

Example 17—In Vitro Effect of A2M on Wound Healing

To test the hypothesis that the addition of proinflammatory cytokines or cartilage-degrading metalloproteinases (ADAMTS and MMP) slow wound healing that will be inhibited by recombinant A2M, a controlled in vitro wound healing assay is performed. Cells from animal wounds are treated with or without proinflammatory cytokines (TNF-α or IL-1β) or cartilage-degrading metalloproteinases (ADAMTS-5, ADAMTS-4, MMP-7, or MMP-12) in the presence or absence of recombinant A2M compositions. Wound cells are incubated 2 days in Serum-Free Media (SFM) with or without 500 ng/mL ADAMTS-4 or ADAMTS-5 and 3-5 µg/mL of MMP-3, MMP-7, MMP-12, or MMP-13. MMP-3 is activated with chymotrypsin before application on wound cells. For cytokine-induced retardation of wound healing, wound cells are incubated 3 days in SFM with or without 80 ng/ml human TNF-α and 8 ng/mL human 1L-1β. Wound healing is enhanced with the addition of 100 µg/mL of purified human recombinant A2M for protease digestion or 5 mg/mL recombinant A2M for cytokine-induced degradation.

Example 18—Wound Fluid Collection Technique

There are several techniques that were utilized to collect wound fluid. One technique involved aspirating wound fluid from wet wounds utilizing a syringe. Another technique involved use of a filter paper to absorb the wound fluid, followed by extraction of the absorbed wound fluid from the filter paper, such as by washing with a buffer. Another technique involved running a straight edge tongue blade across the wound and collecting the fluid that gathered in front of the straight edge, such as with a filter paper.

For example, human chronic wound fluid is extracted from primary wound fluid dressing by soaking a single dressing overnight in 5 ml phosphate buffered saline pH 4.0-6.0 50 mM sodium acetate adjusted to relevant pH with glacial acetic buffer acid pH 7.0-8.0 0.2M Tris(hydroxymethyl)aminornethane (Tris) corrected to buffer relevant PH using 0.2M hydrochloric acid.

Example 19—Effects of A2M Compositions on Wound Healing in Diabetic Rats

Summary

Healing of chronic wounds such as diabetic ulcers is a significant clinical problem. This study examines the in vivo response to the therapeutic recombinant A2M compositions according to the present invention. The preliminary animal study on a diabetic rat model with impaired wound healing is conducted comparing the recombinant A2M compositions described herein with distilled water. As a result, the time to complete closure of wounds is lower in the A2M treated group. The difference in wound healing since day $9^{th}$ of the treatment is apparent. The A2M treated animals have lower scar tissues and the fur growth is complete. In water-treated animals a scar with impaired fur growth is apparent. The results of this study suggest that dermal use of these A2M compositions have a potential to modulate wound healing and stimulate fur growth.

Methods

The animal model for in vivo testing of the recombinant A2M compositions is a full-thickness wound in the dorsal skin of diabetic rats, Wistar rats weighing 200-250 g are used. Animals are caged in separate cages. Diabetes is induced by administration of streptozotocin (Sigma-Aldrich, UK). Streptozotocin is administered at dose of 55 mg/kg intraperitoneally. Before the administration of streptozotocin, a baseline blood glucose of rats is determined, After 48 hours, the blood glucose is again measured to ensure rats are diabetic. The induction of diabetes is confirmed if the blood glucose level is doubled. Glucose is determined by a Glucometer (Infopia Co.; Korea). Determination of blood glucose continues every 5 days to ensure the subsistence of diabetes. Regarding the entity of streptozotocin-induced diabetes, the animals which lose much weight and become week, and those with uncertain blood glucose levels are excluded from the study. A total of 14 rats are used with equal numbers in control and test groups. The test group has a volume of a solution comprising the recombinant A2M composition applied and the control group is dressed with distilled water. At time=0 days, a full-thickness, circular 15 mm diameter wound is created (e.g., according to Wound Rep. Reg. 2002; 10: 286-294). Rats are anaesthetized by intraperitoneal pentobarbital (55 mg/kg) and the dorsal skin is prepared for surgery using Betadine. The wound is created using surgical scissors. At time=0 days dressings are placed, as prepared, directly on the wounds. The wounds are covered by sterile gases and wrapped carefully. Every 2-3 days following surgery, wounds were redressed with fresh control or test dressings while the rats were under anesthesia. The wounds are flushed with sterile saline to remove debris and to clean the wound area. A digital camera is used to take the pictures of the wound. The pictures are examined for wound heating in terms of wound size and appearance of new fresh epithelium. Once photographed, fresh dressings are placed on the wounds, and the wounds are covered again. Control of bias is achieved by assigning a code to each of the experimental groups. Investigators are blinded to the identity of each of the groups and the test and control have a similar appearance. The code is broken following completion of the final 4-week analysis.

In the test group on the $15^{th}$ day of therapy the wound is completely closed and the new, short fur covers the scar area. On the $22^{nd}$ day of therapy the wound is completely healed and the new, long fur covers the entire scar area, No signs of the previous wound can be seen. In the control group on the $15^{th}$ day of therapy the wound is not closed. On the $22^{nd}$ day of testing the wound is closed but the scar is still sever and completely naked.

Wound areas and perimeters are similar in test and control groups; however, there is a tendency for more rapid closure in the test group, particularly at day 15 where the difference in wound areas and perimeters is most pronounced. The time to complete closure of wounds is lower in A2114 treated animals. In both control and test groups, wound area begins to decrease at day $9^{th}$ and approximately complete wound closure first occurs by day $15^{th}$ (one out of seven rats). By day $22^{nd}$, wounds are essentially closed in both groups but growth of fur in the A2M treated group is especially complete as compared to the water-treated group.

The results of this study suggest that dermal preparation comprising the recombinant A2M compositions according to the present invention has potential to enhance wound healing. In addition to accelerating wound closure, A2M treatment in this study appears to improve the quality of the tissue in the healing wound since the fur grew more efficiently than in the control group. Chronic wounds are not only characterized by untimely healing and the inability to remain closed following healing. Thus, time to closure may not be the only relevant end point or sole basis for efficacy of the treatment. Obtaining the healthier scar tissue in the test group animals treated with the recombinant A2M compositions allows anticipating a lowered recurrence rate.

Example 20—Wound Debridement

Recombinant A2M compositions are applied to necrotic tissues on pigs for an in vivo debridement efficacy study. Recombinant A2M compositions, together with a debrider, are used to each of the wounds generated (about 2 cm in diameter). After 24 hours, significant wound debridement is observed on the wounds treated with the A2M compositions. After 5 days, those with recombinant A2M compositions show clean surfaces without any necrotic tissue and complete healing. Debrider treated wounds also show significant debridement after 48 hours. However, the wounds are not as clean as those treated with recombinant A2M compositions, and did not show complete healing after five days.

What is claimed is:

1. A method of treating a mammalian subject with an inflammatory disease or condition, comprising administering to the subject a pharmaceutical composition comprising
   (a) a pharmaceutically effective amount of a recombinant alpha-2-macroglobulin (A2M) polypeptide comprising a non-natural bait region, wherein the non-natural bait region comprises a sequence with at least 80% identity to SEQ ID NO: 20; and
   (b) a pharmaceutically acceptable carrier.

2. The method of claim 1, wherein the recombinant A2M polypeptide is characterized by an enhanced inhibition of a protease compared to inhibition of the protease by a wild-type A2M protein comprising the sequence of SEQ ID NO: 3.

3. The method of claim 1, wherein protease activity is inhibited at a site the pharmaceutical composition is administered.

4. The method of claim 1, wherein administering comprises injecting.

5. The method of claim 1, wherein the method comprises administering the pharmaceutical composition during a surgical procedure.

6. The method of claim 1, wherein the inflammatory disease or condition is a degenerative disease selected from the group consisting of joint degeneration, bone degeneration, cartilage degeneration, tendon degeneration, ligament degeneration, and spine degeneration.

7. The method of claim 1, wherein the inflammatory disease or condition is selected from the group consisting of an autoimmune disease, arthritis, osteoarthritis, inflammatory arthritis, chondrosis, an enthesopathy, and a tendinopathy.

8. The method of claim 1, wherein the inflammatory disease or condition is osteoarthritis.

9. The method of claim 1, wherein the inflammatory disease or condition is selected from the group consisting of joint inflammation caused by surgery, disc inflammation caused by surgery, joint inflammation caused by a joint replacement, disc inflammation caused by a disc replacement, and a combination thereof.

10. The method of claim 1, wherein the inflammatory disease or condition is an injury selected from the group consisting of a ligament injury, a tendon injury, a bone injury, spine injury, and cartilage injury.

11. The method of claim 1, wherein the subject is a human.

12. The method of claim 1, wherein the non-natural bait region comprises a protease recognition sequence selected from the group consisting of a matrix metalloproteinase (MMP) and A Disintegrin and Metalloproteinase with Thrombospondin Motifs (ADAMTS) recognition sequence.

13. The method of claim 1, wherein the non-natural bait region comprises a consensus sequence for a protease selected from the group consisting of a serine protease, a threonine protease, a cysteine protease, an aspartate protease, a metalloprotease, a glutamic acid protease, and combinations thereof.

14. The method of claim 1, wherein the non-natural bait region comprises a suicide inhibitor, wherein the suicide inhibitor is operable to covalently attach a protease to the recombinant A2M polypeptide.

15. The method of claim 1, wherein the non-natural bait region comprises a sequence with at least 85% identity to SEQ ID NO: 20.

16. The method of claim 1, wherein the non-natural bait region comprises a sequence with at least 90% identity to SEQ ID NO: 20.

17. The method of claim 1, wherein the non-natural bait region comprises SEQ ID NO: 20.

18. The method of claim 1, wherein the non-natural bait region comprises a sequence selected from the group consisting of SEQ ID NOs: 34, 36, and 80.

19. The method of claim 1, wherein the recombinant A2M polypeptide comprises a sequence with at least 80% identity to SEQ ID NO: 4.

20. The method of claim 1, wherein the pharmaceutical composition is a liquid.

* * * * *